United States Patent
Andersson et al.

(10) Patent No.: US 8,859,534 B2
(45) Date of Patent: *Oct. 14, 2014

(54) 2-CARBOXAMIDE-7-PIPERAZINYL-BENZOFURAN DERIVATIVES

(71) Applicant: AstraZeneca AB, Sodertalje (SE)

(72) Inventors: Johan Andersson, Sodertalje (SE); Helena Gyback, Sodertalje (SE); Anh Johansson, Sodertalje (SE); Christian Erik Linde, Sodertalje (SE); Jonas Malmstrom, Sodertalje (SE); Gunnar Nordvall, Sodertalje (SE); Tatjana Weigelt, Sodertalje (SE); Gitte Terp, Sodertalje (SE)

(73) Assignee: Acturum Life Science AB, Solna (SE)

(*) Notice: Subject to any disclaimer, the term of this patent is extended or adjusted under 35 U.S.C. 154(b) by 0 days.

This patent is subject to a terminal disclaimer.

(21) Appl. No.: 13/758,098

(22) Filed: Feb. 4, 2013

(65) Prior Publication Data

US 2013/0296296 A1 Nov. 7, 2013

Related U.S. Application Data

(63) Continuation of application No. 12/824,567, filed on Jun. 28, 2010, now Pat. No. 8,367,676.

(60) Provisional application No. 61/221,657, filed on Jun. 30, 2009.

(51) Int. Cl.

| | | |
|---|---|---|
| *A61K 31/496* | (2006.01) | |
| *A61K 31/5377* | (2006.01) | |
| *C07D 405/12* | (2006.01) | |
| *C07D 405/14* | (2006.01) | |
| *C07D 413/14* | (2006.01) | |
| *C07D 307/84* | (2006.01) | |
| *C07D 407/14* | (2006.01) | |
| *C07D 417/14* | (2006.01) | |
| *C07D 307/85* | (2006.01) | |

(52) U.S. Cl.
CPC .......... *C07D 405/12* (2013.01); *C07D 307/84* (2013.01); *C07D 307/85* (2013.01); *C07D 407/14* (2013.01); *C07D 417/14* (2013.01); *C07D 413/14* (2013.01); *C07D 405/14* (2013.01)
USPC ............ 514/210.18; 514/253.09; 514/253.11; 514/252.18; 514/235.8; 544/121; 544/295; 544/364; 544/373

(58) Field of Classification Search
None
See application file for complete search history.

(56) References Cited

U.S. PATENT DOCUMENTS

| 8,367,676 B2 | 2/2013 | Andersson et al. |
| 2006/0160824 A1 | 7/2006 | Heinrich et al. |
| 2006/0160877 A1 | 7/2006 | Luithle et al. |

FOREIGN PATENT DOCUMENTS

| WO | WO99/05140 | 2/1999 |
| WO | WO 00/43382 | 7/2000 |
| WO | WO 02/102774 | 12/2002 |
| WO | WO 03/104227 | 12/2003 |
| WO | WO 2004/046124 | 6/2004 |
| WO | WO 2005/077885 | 8/2005 |
| WO | WO 2006/062481 | 6/2006 |
| WO | WO 2007/053093 | 5/2007 |
| WO | WO 2007/094718 | 8/2007 |
| WO | WO 2008/037681 | 4/2008 |
| WO | WO 2008/055808 | 5/2008 |

OTHER PUBLICATIONS

Kling et al. Bioorganic & Medicinal Chemistry Letters, vol. 15, pp. 5567-5573 (2005).*
Barnes and Sharp, "A review of central 5-HT receptors and their function", Neuropharmacology, 1999, 38, pp. 1083-1152.
Barros et al, "Anxiolytic-like effects of the selective 5-HT1A receptor antagonist WAY 100635 in non-human primates", Eur. J. Pharmacol. 2003, 482, pp. 197-203.

(Continued)

*Primary Examiner* — Emily Bernhardt
(74) *Attorney, Agent, or Firm* — Baker & Hostetler LLP

(57) ABSTRACT

The present invention relates to compounds of formula (I),

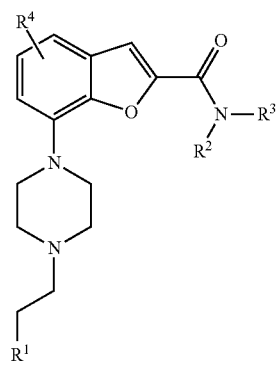

wherein
$R^1$ is heteroaryl or heterocyclyl, optionally substituted;
$R^2$ is $C_{1-4}$alkyl, heterocyclyl, $C_{1-4}$alkylaryl, $C_{1-4}$alkylheteroaryl, carbocyclyl, $C_{1-4}$alkylheterocyclyl, heterocyclylheteroaryl, aryl-heterocyclyl, carbocyclyl-heteroaryl, heterocyclyl-aryl, optionally substituted;
$R^3$ is hydrogen or $C_{1-4}$alkyl, or
$R^2$ and $R^3$ may together with the nitrogen atom, form a saturated ring system containing 4, 5 or 6 ring forming atoms, and optionally substituted;
$R^4$ is hydrogen, halogen, methyl or methoxy; to pharmaceutical composition containing said compounds and to the use of said compounds in therapy, for instance in treating cognitive disorders.
The present invention further relates to new intermediates useful in the preparation thereof.

11 Claims, No Drawings

(56) References Cited

OTHER PUBLICATIONS

Beller et al, "Biologically Active Compounds through Catalysis: Efficient Synthesis of N-(Heteroarylcarbonyl)-N'-(arylalkyl)piperazines", Chem. Eur. J. 2004, 10, pp. 746-757.

Beller and Breidl, "Base-Catalyzed Hydroamination of Aromatic Olefins—An Efficient Route to 1-Aryl-4-(arylethyl)piperazines1)",Tetrahedron 1998, 54, pp. 6359-6368.

Boast et al, "5HT Antagonists Attenuate MK801—Impaired Radial Arm Maze Performance in Rats", Neurobiol Learning and Memory, 1999, 71, pp. 259-271.

Carli et al, "(S)-Way 100135, a 5-HT1A receptor antagonist, prevents the impairment of spatial learning caused by intrahippocampal scopolamine", Eur J Pharmacol, 1995, 283, pp. 133-139.

Cliffe et al, "7-Amino-5,6,7,8-tetrahydroquinolines. Preparation from 5,6-Dihydroquinoline and Nitrogen Nucleophiles", Tetrahedron Lett. 1991, 32, pp. 6789-6792.

Domenech et al, "Characterization of human serotonin 1D and 1B receptors using [ 3H]-GR-125743, a novel radiolabelled serotonin 5HT1D/1B receptor antagonist", Naunyn-Schmiedeberg's Arch Pharmacol 1997, 356, pp. 328-334.

Harder and Ridley, "The 5-HT1A antagonist, WAY 100 635, alleviates cognitive impairments induced by dizocilpine (MK-801) in monkeys", Neuropharmacology, 2000, 39, pp. 547-552.

Hartwig et al, "Ruthenium-Catalyzed Anti-Markovnikov Hydroamination of Vinylarenes", J. Am. Chem. Soc. 2004, 126, pp. 2702-2703.

Heinrich et al., "Synthesis and Structure—Activity Relationship in a Class of Indolebutylpiperazines as Dual 5-HT1A Receptor Agonists and Serotonin Reuptake Inhibitors", J. Med. Chem. 2004, 47, pp. 4684-4692.

Hu et al, "Effects of the 5-HT1B receptor antagonist NAS-181 on extracellular levels of acetylcholine, glutamate and GABA in the frontal cortex and ventral hippocampus of awake rats: A microdialysis study", Eur Neuropsychopharmacol, 2007, 17, pp. 580-586.

Jerning et al, "NAD-299 Antagonises 5-HT-Stimulated and Spiperone-Inhibited [35S ]GTP.gamma.S Binding in Cloned 5 HT1A Receptors",J Recept Signal Transduct Res 2002, 22, pp. 483-495.

Millan et al, "The Serotonin1A Receptor Partial Agonist S15535 [4-(Benzodioxan-5-y;)1-(indan-2-yl)piperazine] Enhances Cholinergic Transmission and Cognitive Function in Rodents: A Combined Neurochemical and Behavioral Anasysis", J. Phamacol Exp Ther, 2004, 311, pp. 190-203.

Moret and Briley, "The possible role of 5-HT1B/D receptors in psychiatric disorders and their potential as a target for therapy", Eur. J. Pharmacol 2000, 404, pp. 1-12.

Steen et al., "Structure-Affinity Relationship Studies on 5-HT1A Receptor Ligands. 2. Heterobicyclic Phenylpiperazines with N4-Aralkyl Substituents", J. Med. Chem. 1994, 37, pp. 2761-2773.

Woodward et al, "Microwave acceleration in DABAL-Me3-mediated amide formation", Tetrahedron Lett. 2008, 49, pp. 5687-5688.

.ANG.hlander-Luttgen et al, "Analysis of the Role of the 5-HT1B Receptor in Spatial and Aversive Learning in the Rat" , Neuropsychopharmacology, 2003, 28, pp. 1642-1655.

STN International RN: 1100176-91-7 with Chemical Structure; Entered STN Feb. 3, 2009.

STN International RN: 1100098-22-3 with Chemical Structure; Entered STN Feb. 3, 2009.

STN International RN: 1100188-86-0 with Chemical Structure; Entered STN Feb. 3, 2009.

STN International RN: 1100088-36-5 with Chemical Structure; Entered STN Feb. 3, 2009.

STN International RN: 1100058-20-5 with Chemical Structure; Entered STN Feb. 3, 2009.

STN International RN: 326618-90-0 with Chemical Structure; Entered STN Mar. 11, 2001.

STN International RN: 326616-04-0 with Chemical Structure; Entered STN Mar. 11, 2001.

\* cited by examiner

2-CARBOXAMIDE-7-PIPERAZINYL-BENZO-FURAN DERIVATIVES

CROSS-REFERENCE TO RELATED APPLICATIONS

This is a continuation of Application 12/824,567 filed Jun. 28, 2010, allowed as U.S. Pat. No. 8,367,676, which claims the benefit of Provisional Application No. 61/221,657, filed Jun. 30, 2009. The entire text of the above-referenced provisional patent application is incorporated by reference into this application.

TECHNICAL FIELD OF THE INVENTION

The present invention relates to new compounds, to pharmaceutical composition containing said compounds, and to the use of said compounds in therapy. The present invention further relates to processes for the preparation of said compounds and to intermediates useful in the preparation thereof.

BACKGROUND

Serotonin (5-hydroxy-tryptamine, 5-HT) receptors play an important role in many physiological functions as well as pathological disorders including but not limited to depression, generalized anxiety, eating disorders, panic disorder, sleep disorders, aggression, dementia and other cognitive dysfunctions. Furthermore, serotonin has been implicated in gastrointestinal disorders, cardiovascular regulation, motor disorders, endocrine disorders, vasospasm and sexual dysfunction. The 5-HT receptors are distributed throughout the body and can be divided into at least 14 different subtypes (Barnes and Sharp, Neuropharmacology, (1999) 38, 1083-1152). The various subtypes are responsible for serotonin's actions in many pathophysiological conditions. The 5-HT1 family of receptors has high affinity for serotonin and consists of five related receptors. This family includes the 5-HT1A, 5-HT1B and 5-HT1D receptor subtypes.

Compounds interacting with the 5-HT1 family are known to have therapeutic potential in the above-mentioned disorders and diseases. In particular, compounds which are 5-HT1A and 5-HT1B antagonists have been shown to improve cognitive function. Moreover, compounds which are 5-HT1A, 5-HT1B, and 5-HT1D antagonists have been shown to be antidepressant and anxiolytic agents. Compounds which are agonists at the 5-HT1B and 5-HT1D receptors, have been used in the treatment of migraine and could also be useful in the treatment of Parkinson's Disease.

Scientific research has revealed a potential therapeutic use for modulators of the 5-HT1A and the 5-HT1B receptors, especially with regard to various CNS disorders. Blocking 5-HT1A receptor function has been shown to enhance cholinergic transmission. Partial 5-HT1A agonists as well as 5-HT1A antagonists have been shown to increase the release of acetylcholine (J. Phamacol. Exp. Ther. 311 (2004), 190-203). 5-HT1A antagonists have also been shown in in vivo cognition models to reverse cognitive deficits induced by the muscarinic antagonist scopolamine (Carli et al, Eur. J. Pharmacol., 283 (1995), 133) or the NMDA antagonist MK-801 (Neurobiol. Learning and Memory, 71 (1999), 259; Neuropharmacology 39 (2000) 547-552). Blocking the 5-HT1B receptor has been shown in microdialysis experiments to increase the levels of acetylcholine in the frontal cortex and hippocampus of awake rats (Hu et al, Eur. Neuropsychopharmacology 17 (2007), 580-586) and have positive effects in cognition models (Åhlander-Luttgen et al, Neuropsychopharmacology (2003) 28, 1642-1655). Therefore, compounds that are partial agonists or antagonists of the 5-HT1A and/or 5-HT1B receptors should be useful in the treatment of cognitive disorders such as Alzheimer's disease.

Scientific research have shown that the use of 5-HT1B antagonists should be useful in the treatment of psychiatric disorders such as depression, anxiety, OCD (obsessive compulsive disorders) and other psychiatric disorders (Eur. J. Pharmacol. (2000), 404, 1-12).

5-HT1A antagonists have shown to be active in models of anxiety in non-human primates (Eur. J. Pharmacol. (2003) 482 197-203). Therefore, compounds that are partial agonists or antagonists of the 5-HT1A and/or 5-HT1B receptors should be useful in the treatment of psychiatric disorders such as depression, anxiety and OCD.

DISCLOSURE OF THE INVENTION

The object of the present invention is to provide new compounds having a dual 5-HT receptor binding effect, namely compounds which bind to the 5-HT1A and 5-HT1B receptors and thus modulate the effects of serotonin and thereby also to increase levels of acetylcholine and/or effects levels of other neurotransmitters such as glutamate, serotonin, noradrenaline and their metabolites.

Compounds of the present invention may also have the advantage that they may be more efficacious than, be less toxic than, have a broader range of activity than, be more potent than, be longer acting than, produce fewer side effects than, be more easily absorbed than, or that they may have other useful pharmacological properties over, compounds known in the prior art.

The present invention relates to compound of formula (I),

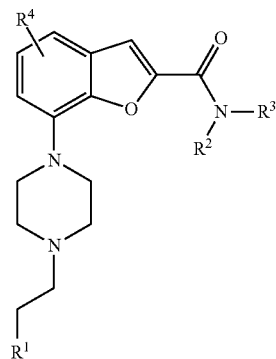

wherein
$R^1$ is heteroaryl or heterocyclyl, wherein said heteroaryl or heterocyclyl is optionally substituted with one or more substituents selected from $C_{1-4}$alkyl, halogen, $CF_3$, CN, $C_{1-4}$alkoxy, $C(O)C_{1-4}$alkyl, $NC_{1-4}$alkyl$C(O)C_{1-4}$alkyl, $NHC(O)C_{1-4}$alkyl, $C(O)HN(C_{1-4}$alkyl) and $C(O)N(C_{1-4}$alkyl)$_2$;
$R^2$ is $C_{1-4}$alkyl, heterocyclyl, $C_{1-4}$alkylaryl, $C_{1-4}$alkylheteroaryl, carbocyclyl, $C_{1-4}$alkylheterocyclyl, heterocyclyl-heteroaryl, aryl-heterocyclyl, carbocyclyl-heteroaryl, heterocyclyl-aryl, wherein in said groups the heterocyclyl, aryl, heteroaryl or carbocyclyl moiety may be optionally substituted with one or more substituents selected from halogen, $C_{1-4}$alkoxy, $C(O)C_{1-4}$alkyl, $C_{0-4}$alkylSO$_2$ $C_{1-4}$alkyl, cyano, hydroxy, and $C_{1-4}$alkyl;

$R^3$ is hydrogen or $C_{1-4}$alkyl, or $R^2$ and $R^3$ may together with the nitrogen atom, form a saturated ring system containing 4, 5 or 6 ring forming atoms selected from carbon or nitrogen and wherein said ring system is optionally substituted with one or more substituent selected from halogen, $C_{1-4}$alkyl and $C_{1-4}$alkoxy, O-heteroaryl;

$R^4$ is hydrogen, halogen, methyl or methoxy;

or a pharmaceutically acceptable salt thereof.

According to one embodiment of the present invention, $R^1$ is heteroaryl.

According to one embodiment of the present invention, said heteroaryl is pyridinyl.

According to one embodiment of the present invention, said heteroaryl is indolinyl.

According to one embodiment of the present invention, $R^2$ and $R^3$ may together with the nitrogen atom form an azetidine.

According to one embodiment of the present invention, $R^1$ is pyridine-2-yl optionally substituted with one or more substituent selected from $C_{1-4}$alkyl, halogen, $CF_3$, CN, $C_{1-4}$alkoxy, $C(O)C_{1-4}$alkyl, $NHC(O)C_{1-4}$alkyl;

$R^2$ is $C_{1-4}$alkyl, heterocyclyl, $C_{1-4}$alkylaryl, $C_{1-4}$alkylheteroaryl, carbocyclyl, $C_{1-4}$alkylheterocyclyl, heterocyclyl-heteroaryl, aryl-heterocyclyl, carbocyclyl-heterocyclyl, heterocyclyl-aryl, wherein said groups the heterocyclyl, aryl, heteroaryl or carbocyclyl moiety may be optionally substituted with one or more substituents selected from halogen, $C_{1-4}$alkoxy, $C(O)C_{1-4}$alkyl, $C_{0-4}$alkyl$SO_2C_{1-4}$alkyl, CN, hydroxy, and $C_{1-4}$alkyl;

$R^3$ is hydrogen or $C_{1-4}$alkyl, or $R^2$ and $R^3$ may together with the nitrogen atom, form a saturated ring system containing 4, 5 or 6 ring forming atoms selected from carbon or nitrogen and wherein said ring system is optionally substituted with one or more substituent selected from halogen, $C_{1-4}$alkyl and $C_{1-4}$alkoxy and O-heteroaryl;

$R^4$ is hydrogen, halogen, or methoxy;

or a pharmaceutically acceptable salt thereof.

According to one embodiment of the present invention, $R^1$ is pyridine-2-yl optionally substituted with one or more substituent selected from $C_{1-4}$alkyl, halogen, $CF_3$, CN, $C_{1-4}$alkoxy, $C(O)C_{1-4}$alkyl and $NHC(O)C_{1-4}$alkyl.

According to one embodiment of the present invention, $R^4$ is hydrogen.

According to one embodiment of the present invention, $R^1$ is pyridine-2-yl;

$R^2$ is $C_{1-4}$alkyl, heterocyclyl, $C_{1-4}$alkylaryl, $C_{1-4}$alkylheteroaryl, carbocyclyl, $C_{1-4}$alkylheterocyclyl, heterocyclyl-heteroaryl, aryl-heterocyclyl, carbocyclyl-heterocyclyl, heterocyclyl-aryl and heterocyclyl-O-heteroaryl, wherein said groups the heterocyclyl, aryl, heteroaryl or carbocyclyl moiety may be optionally substituted with one or more substituents selected from halogen, $C_{1-4}$alkoxy, $C(O)C_{1-4}$alkyl, $C_{0-4}$alkyl$SO_2C_{1-4}$alkyl, cyano, hydroxy, and $C_{1-4}$alkyl;

$R^3$ is hydrogen or $C_{1-4}$alkyl, or $R^2$ and $R^3$ may together with the nitrogen atom, form a saturated ring system containing 4, 5 or 6 ring forming atoms selected from carbon or nitrogen;

$R^4$ is hydrogen, or a pharmaceutically acceptable salt thereof.

According to one embodiment of the present invention, $R^3$ is hydrogen.

According to one embodiment of the present invention, $R^2$ is $C_{1-4}$alkylheteroaryl.

According to one embodiment of the present invention, wherein $R^2$ is $C_{1-4}$alkylheteroaryl said heteroaryl is pyridinyl, pyrimidinyl, imidazolyl, pyrazolyl or benzodioxolyl.

According to one embodiment of the present invention, $R^2$ is $C_{1-4}$alkylaryl.

According to one embodiment of the present invention, wherein $R^2$ is $C_{1-4}$alkylaryl said aryl is phenyl.

According to one embodiment of the present invention, at least one of $R^2$ or $R^3$ is $C_{1-4}$alkyl.

According to one embodiment of the present invention, $R^2$ and $R^3$ are $C_{1-4}$alkyl.

According to one embodiment of the present invention, $R^1$ is pyridine-2-yl;

$R^2$ and $R^3$ are $C_{1-4}$alkyl;

$R^4$ is hydrogen, or a pharmaceutically acceptable salt thereof.

The present invention also relates to the compound N,N-dimethyl-7-(4-(2-(pyridin-2-yl)ethyl)piperazin-1-yl)benzofuran-2-carboxamide, or a pharmaceutically acceptable salt thereof.

The present invention also relates to a compound, which is N,N-dimethyl-7-(4-(2-(pyridin-2-yl)ethyl)piperazin-1-yl)benzofuran-2-carboxamide in substantially crystalline form.

The present invention also relates to a compound, which is N,N-dimethyl-7-(4-(2-(pyridin-2-yl)ethyl)piperazin-1-yl)benzofuran-2-carboxamide characterized by the X-ray powder diffraction (XRDP) °2θ (Cu Kα) values 5.48 and 9.36.

The present invention also relates to a compound, which is 7-(4-(2-(Pyridin-2-yl)ethyl)piperazin-1-yl)-N-(pyridin-2-ylmethyl)benzofuran-2-carboxamide;

N-(4-Morpholinophenyl)-7-(4-(2-(pyridin-2-yl)ethyl)piperazin-1-yl)benzofuran-2-carboxamide;

N-(1-Phenylpiperidin-4-yl)-7-(4-(2-(pyridin-2-yl)ethyl)piperazin-1-yl)benzofuran-2-carboxamide;

N-(4-(Methylsulfonyl)benzyl)-7-(4-(2-(pyridin-2-yl)ethyl)piperazin-1-yl)benzofuran-2-carboxamide;

N-((1-Methyl-1H-imidazol-4-yl)methyl)-7-(4-(2-(pyridin-2-yl)ethyl)piperazin-1-yl)benzofuran-2-carboxamide;

N-(1-Acetylpiperidin-4-yl)-7-(4-(2-(pyridin-2-yl)ethyl)piperazin-1-yl)benzofuran-2-carboxamide;

N-(1-(Pyridin-2-yl)ethyl)-7-(4-(2-(pyridin-2-yl)ethyl)piperazin-1-yl)benzofuran-2-carboxamide;

N-(1-(3-Chloropyridin-2-yl)piperidin-4-yl)-7-(4-(2-(pyridin-2-yl)ethyl)piperazin-1-yl)benzofuran-2-carboxamide;

N-(4-Cyanobenzyl)-7-(4-(2-(pyridin-2-yl)ethyl)piperazin-1-yl)benzofuran-2-carboxamide;

N-(Benzo[d][1,3]dioxol-5-ylmethyl)-7-(4-(2-(pyridin-2-yl)ethyl)piperazin-1-yl)benzofuran-2-carboxamide;

N-Methyl-7-(4-(2-(pyridin-2-yl)ethyl)piperazin-1-yl)benzofuran-2-carboxamide;

N-Cyclopropyl-7-(4-(2-(pyridin-2-yl)ethyl)piperazin-1-yl)benzofuran-2-carboxamide;

N-(3,3-Difluorocyclobutyl)-7-(4-(2-(pyridin-2-yl)ethyl)piperazin-1-yl)benzofuran-2-carboxamide;

Azetidin-1-yl(7-(4-(2-(pyridin-2-yl)ethyl)piperazin-1-yl)benzofuran-2-yl)methanone;

(7-(4-(2-(Pyridin-2-yl)ethyl)piperazin-1-yl)benzofuran-2-yl)(pyrrolidin-1-yl)methanone;

N-(4-(Methylsulfonylmethyl)benzyl)-7-(4-(2-(pyridin-2-yl)ethyl)piperazin-1-yl)benzofuran-2-carboxamide;

N-(3-Methoxyphenethyl)-7-(4-(2-(pyridin-2-yl)ethyl)piperazin-1-yl)benzofuran-2-carboxamide;

N-Methyl-N-(3-(methylsulfonyl)benzyl)-7-(4-(2-(pyridin-2-yl)ethyl)piperazin-1-yl)benzofuran-2-carboxamide;

N-((6-Cyanopyridin-3-yl)methyl)-7-(4-(2-(pyridin-2-yl)ethyl)piperazin-1-yl)benzofuran-2-carboxamide;

N-Methyl-7-(4-(2-(pyridin-2-yl)ethyl)piperazin-1-yl)-N-(pyridin-3-ylmethyl)benzofuran-2-carboxamide;

N-(3-Cyanobenzyl)-7-(4-(2-(pyridin-2-yl)ethyl)piperazin-1-yl)benzofuran-2-carboxamide;
(7-(4-(2-(Pyridin-2-yl)ethyl)piperazin-1-yl)benzofuran-2-yl)(4-(thiazol-2-yl)piperazin-1-yl)methanone;
N-(1-(3-Methoxypyridin-2-yl)piperidin-4-yl)-7-(4-(2-(pyridin-2-yl)ethyl)piperazin-1-yl)benzofuran-2-carboxamide;
N-Methyl-7-(4-(2-(pyridin-2-yl)ethyl)piperazin-1-yl)-N-(pyridin-2-ylmethyl)benzofuran-2-carboxamide;
N-(3-Methoxybenzyl)-7-(4-(2-(pyridin-2-yl)ethyl)piperazin-1-yl)benzofuran-2-carboxamide;
N-(1-(Pyridin-2-yl)cyclopropyl)-7-(4-(2-(pyridin-2-yl)ethyl)piperazin-1-yl)benzofuran-2-carboxamide;
N-(4-Methoxybenzyl)-7-(4-(2-(pyridin-2-yl)ethyl)piperazin-1-yl)benzofuran-2-carboxamide;
N-(2-(4-Methylpyrimidin-2-yl)ethyl)-7-(4-(2-(pyridin-2-yl)ethyl)piperazin-1-yl)benzofuran-2-carboxamide;
N-(2-(1-Methyl-1H-imidazol-4-yl)ethyl)-7-(4-(2-(pyridin-2-yl)ethyl)piperazin-1-yl)benzofuran-2-carboxamide;
7-(4-(2-(Pyridin-2-yl)ethyl)piperazin-1-yl)-N-((tetrahydro-2H-pyran-4-yl)methyl)benzofuran-2-carboxamide;
N-(1-(1-Methyl-1H-pyrazol-5-yl)ethyl)-7-(4-(2-(pyridin-2-yl)ethyl)piperazin-1-yl)benzofuran-2-carboxamide;
N-(1-(6-Methylpyridin-3-yl)ethyl)-7-(4-(2-(pyridin-2-yl)ethyl)piperazin-1-yl)benzofuran-2-carboxamide;
N-((2-Methylpyrimidin-5-yl)methyl)-7-(4-(2-(pyridin-2-yl)ethyl)piperazin-1-yl)benzofuran-2-carboxamide;
7-(4-(2-(Pyridin-2-yl)ethyl)piperazin-1-yl)-N-(pyridin-3-ylmethyl)benzofuran-2-carboxamide;
(7-(4-(2-(Pyridin-2-yl)ethyl)piperazin-1-yl)benzofuran-2-yl)(3-(pyridin-3-yloxy)azetidin-1-yl)methanone;
N-(3-Hydroxybenzyl)-7-(4-(2-(pyridin-2-yl)ethyl)piperazin-1-yl)benzofuran-2-carboxamide;
7-(4-(2-(4-Methoxypyridin-2-yl)ethyl)piperazin-1-yl)-N,N-dimethylbenzofuran-2-carboxamide;
N,N-Dimethyl-7-(4-(2-(5-methylpyridin-2-yl)ethyl)piperazin-1-yl)benzofuran-2-carboxamide;
7-(4-(2-(4-Cyanopyridin-2-yl)ethyl)piperazin-1-yl)-N,N-dimethylbenzofuran-2-carboxamide;
N,N-Dimethyl-7-(4-(2-(6-(trifluoromethyl)pyridin-2-yl)ethyl)piperazin-1-yl)benzofuran-2-carboxamide;
7-(4-(2-(5-Acetylpyridin-2-yl)ethyl)piperazin-1-yl)-N,N-dimethylbenzofuran-2-carboxamide;
7-(4-(2-(5-Acetamidopyridin-2-yl)ethyl)piperazin-1-yl)-N,N-dimethylbenzofuran-2-carboxamide;
Azetidin-1-yl(7-(4-(2-(6-methoxypyridin-2-yl)ethyl)piperazin-1-yl)benzofuran-2-yl)methanone;
7-(4-(2-(6-Methoxypyridin-2-yl)ethyl)piperazin-1-yl)-N,N-dimethylbenzofuran-2-carboxamide;
7-(4-(2-(5-Fluoropyridin-2-yl)ethyl)piperazin-1-yl)-N,N-dimethylbenzofuran-2-carboxamide;
7-(4-(2-(3-Methoxy-2-pyridyl)ethyl)piperazin-1-yl)-N,N-dimethylbenzofuran-2-carboxamide;
1-(5-(2-(4-(2-(Azetidine-1-carbonyl)benzofuran-7-yl)piperazin-1-yl)ethyl)indolin-1-yl)ethanone;
5-Fluoro-N,N-dimethyl-7-(4-(2-(pyridin-2-yl)ethyl)piperazin-1-yl)benzofuran-2-carboxamide;
7-(4-(2-(1-Acetylindolin-5-yl)ethyl)piperazin-1-yl)-5-fluoro-N,N-dimethylbenzofuran-2-carboxamide;
5-Methoxy-N,N-dimethyl-7-(4-(2-(pyridin-2-yl)ethyl)piperazin-1-yl)benzofuran-2-carboxamide and
4-Bromo-N,N-dimethyl-7-(4-(2-(pyridin-2-yl)ethyl)piperazin-1-yl)benzofuran-2-carboxamide;
or a pharmaceutically acceptable salt thereof.

The present invention also relates to a compound, which is 7-(4-(2-(1-Acetylindolin-5-yl)ethyl)piperazin-1-yl)-N,N-dimethylbenzofuran-2-carboxamide, or a pharmaceutically acceptable salt thereof.

For the avoidance of doubt the present invention relates to any one of compounds falling within the scope of formula (I) as defined above.

For the avoidance of doubt it is to be understood that where in this specification a group is qualified by "hereinbefore defined", "defined hereinbefore" or "defined above" the said group encompasses the first occurring and broadest definition as well as each and all of the other definitions for that group.

As used herein, "alkoxy", refers to radicals of the general formula —O—R wherein R is selected from both branched and straight chain saturated aliphatic hydrocarbon radicals having from 1 to 12 carbon atoms or if a specified number of carbon atoms is provided then that specific number would be intended. For example "$C_{1-4}$ alkoxy" denotes alkoxy having 1, 2, 3 or 4 carbon atoms. Examples of alkoxy include, but are not limited to, methoxy, ethoxy, propoxy, isopropoxy, butoxy, t-butoxy and isobutoxy.

The term "halo" or "halogen" refers to fluoro, chloro, bromo and iodo.

Where optional substituents are chosen from "one or more" groups it is to be understood that this definition includes all substituents being chosen from one of the specified groups or the substituents being chosen from two or more of the specified groups.

As used herein, the term "heterocyclyl" or "heterocyclic" or "heterocycle" refers to a saturated, unsaturated or partially saturated, monocyclic, bicyclic or tricyclic ring (unless otherwise stated) containing 3 to 20 atoms of which 1, 2, 3, 4 or 5 ring atoms are chosen from nitrogen, sulphur or oxygen, and where unless stated to the contrary a ring nitrogen or sulphur atom is optionally oxidised to form the N-oxide or S-oxide(s) or a ring nitrogen is optionally quarternized; wherein a ring —NH is optionally substituted with acetyl, formyl or methyl; and a ring is optionally substituted with one or more halo. It is understood that when the total number of S and O atoms in the heterocyclyl exceeds 1, then these heteroatoms are not adjacent to one another. If the said heterocyclyl group is bicyclic then at least one of the rings may optionally be a heteroaromatic or aromatic ring provided that at least one of the rings is non-heteroaromatic. If the said heterocyclyl group is monocyclic then it must not be aromatic. Examples of heterocyclyls include, but are not limited to, piperidinyl, N-acetylpiperidinyl, N-methylpiperidinyl, homopiperazinyl, piperazinyl, pyrrolidinyl, azetidinyl, morpholinyl, indolinyl, tetrahydropyranyl (i.e. tetrahydro-2H-pyranyl), dihydro-2H-pyranyl, tetrahydrofuranyl, benzo[1,3]dioxolyl, 4-dioxanyl and 1,3-dioxanyl. According to one embodiment of the present invention the term "heterocyclyl" are piperidinyl, piperazinyl, pyrrolidinyl, azetidinyl, morpholinyl and tetrahydropyranyl (i.e. tetrahydro-2H-pyranyl). As used herein, "heteroaryl" refers to an aromatic heterocycle containing 5 to 20 atoms of which 1, 2, 3, 4 or 5 ring atoms are chosen from nitrogen, sulphur or oxygen. Heteroaryl groups include monocyclic and biycyclic systems. Examples of heteroaryl groups include without limitation, pyridyl (i.e., pyridinyl), pyrimidinyl, pyrazinyl, pyridazinyl, triazinyl, furyl (i.e. furanyl), quinolyl, isoquinolyl, thienyl, imidazolyl, thiazolyl, indolyl, pyrryl, oxazolyl, benzothienyl, benzothiazolyl, isoxazolyl, pyrazolyl, triazolyl, tetrazolyl, indazolyl, 1,2,4-thiadiazolyl, isothiazolyl, benzothienyl, benzofuryl (i.e. benzofuranyl), benzimidazolyl, benzoxazolyl, aza-benzoxazolyl, indolinyl (i.e. 2,3-dihydro-1H-indolyl), imidazothiazolyl, benzodioxolyl and the like. According to one embodiment of the present invention the term "heteroaryl" are pyridyl (i.e., pyridinyl), pyrimidinyl, imidazolyl, thiazolyl, pyrazolyl, triazolyl, benzofuryl (i.e. benzofuranyl), indolinyl (i.e. 2,3-dihydro-1H-indolyl) and benzodioxolyl.

A "carbocyclyl" is a saturated or partially unsaturated mono or bicyclic carbon ring that contains 3-12 atoms. In one aspect of the invention, "carbocyclyl" is a monocyclic ring containing 3 to 6 atoms. Examples of, but not limited to, the term "carbocyclyl" are cyclopropyl, cyclobutyl, 1-oxocyclopentyl, cyclopentyl, cyclopentenyl, cyclohexyl, cyclohexenyl, and bicyclo[2.2.1]heptane. According to one embodiment of the present invention the term "carbocyclyl" are cyclopropyl and cyclobutyl.

An "aryl" is a aromatic mono or bicyclic ring containing 5-12 atoms. In one aspect of the invention, "aryl" is a monocyclic ring containing 5 to 6 carbon atoms. In another aspect of the invention, "aryl" is a bicyclic ring containing 10 atoms. In such bicyclic rings one of the rings is aromatic, while the other ring may be aromatic or partially unsaturated. Examples of the tem "aryl" are phenyl, naphtyl, tetralinyl and indenyl, a suitable "aryl" is phenyl.

The terms "$C_{1-4}$alkylheteroaryl", "$C_{1-4}$alkylaryl" and "$C_{1-4}$alkylheterocyclyl" include both straight and branched chain alkyl groups of between one and four carbon atoms and said alkyl groups link to the heteroaryl, aryl or heterocycle, respectively. Non-limiting examples therefore include benzyl, phenethyl, phenylethyl, cyclopropylmethyl, cyclohexylethyl, pyridin-2-ylmethyl, pyridin-2-ylethyl, 4-tetrahydropyranylmethyl, 2-pyrazinylethyl, 1-imidazolylethyl, 2-(pyridin-2-yl)ethyl, pyridin-3-ylmethyl, 2-(pyrimidin-2-yl)ethyl, pyrimidin-5-ylmethyl, (1-methyl-pyrazol-4-yl)ethyl, (1-methyl-imidazol-4-yl)methyl, 2-(1-methyl-imidazol-4-yl)ethyl, 1,3-benzodioxol-5-ylmethyl and 1-thiophen-2-ylethyl.

It will be appreciated that throughout the specification, the number and nature of substituents on rings in the compounds of the invention will be selected so as to avoid sterically undesirable combinations.

For the avoidance of doubt the present invention relates to any one of the specific compounds mentioned above.

As used herein, the phrase "protecting group" means temporary substituents which protect a potentially reactive functional group from undesired chemical transformations. Examples of such protecting groups include esters of carboxylic acids, silyl ethers of alcohols, and acetals and ketals of aldehydes and ketones respectively. The field of protecting group chemistry has been reviewed (Wuts, P. G. M.; Greene, T. W. *Greene's Protective Groups in Organic Synthesis*, 4$^{th}$ ed.; Wiley-Interscience: New York, 2006).

The present invention relates to the compounds of formula (I) as hereinbefore defined as well as to pharmaceutical acceptable salts thereof. Salts for use in pharmaceutical compositions will be pharmaceutically acceptable salts, but other salts may be useful in the production of the compounds of formula (I).

A suitable pharmaceutically acceptable salt of the compounds of the invention is, for example, an acid-addition salt, for example a salt with an inorganic or organic acid. Other pharmaceutically acceptable salts and methods of preparing these salts may be found in, for example, Remington's Pharmaceutical Sciences (18th Edition, Mack Publishing Co.) The compounds of the present invention may also exist as solvates, including hydrates, cocrystals or mixtures thereof. Thus, the pharmaceutically acceptable salts of the compounds of the present invention also include the solvates and hydrates of the pharmaceutically acceptable salts thereof.

The compounds of the invention may exhibit tautomerism. All tautomeric forms and mixtures thereof are included within the scope of the invention.

The compounds of the invention may also contain one or more asymmetric carbon atoms and may therefore exhibit optical and/or diastereoisomerism. Diastereoisomers may be separated using conventional techniques, e.g. chromatography or fractional crystallisation. The various stereoisomers may be isolated by separation of a racemic or other mixture of the compounds using conventional, e.g. fractional crystallization or HPLC, techniques. Alternatively the desired optical isomers may be made by reaction of the appropriate optically active starting materials under conditions which will not cause racemisation or epimerisation, or by derivatisation, for example with a homochiral acid followed by separation of the diastereomeric esters by conventional means (e.g. HPLC, chromatography over silica). All stereoisomers are included within the scope of the invention.

The present invention further includes isotopically-labeled compounds of the invention. An "isotopically" or "radiolabeled" compound is a compound of the invention where one or more atoms are replaced or substituted with an atom having an atomic mass or mass number different from the atomic mass or mass number typically found in nature (i.e., naturally occurring). Suitable stable or radioactive nuclides that may be incorporated in compounds of the present invention include but are not limited to $^{2}$H (also written as D for deuterium), $^{3}$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. The radionuclide that is incorporated in the instant radio-labeled compounds will depend on the specific application of that radio-labeled compound. For example, for in vitro receptor labeling and competition assays, compounds that incorporate $^{3}$H, $^{14}$C, $^{82}$Br, $^{125}$I, $^{131}$I, $^{35}$S, or will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is understood that a "radio-labeled compound" is a compound that has incorporated at least one radionuclide. In some embodiments the radionuclide is selected from the group consisting of $^{3}$H, $^{14}$C, $^{125}$I, $^{35}$S and $^{82}$Br.

Methods of Preparation

Preparation of End Products

All the variables $R^1$ to $R^4$ are as defined for the compound of the formula (I) above unless mentioned otherwise.

The compound of formula (I) may be prepared in three different ways as outlined in Scheme 1:

a) The amide of formula (I) may be synthesized, as described in Scheme (I), by reacting a carboxylate of formula (II), wherein M is lithium or sodium, with a primary or secondary amine in the presence of a coupling reagent, such as TSTU, CDI, DCC, HBTU, HATU, TBTU or HOBt, with a base, such as triethylamine, diisopropylethylamine or DMAP, in an inert solvent, such as DMA, DMF or THF, at room temperature for a time of 1 h to 24 h.

b) Alternatively, a mixed anhydride may be prepared by treating a carboxylate of formula (II) with for example pivaloyl chloride. The formed mixed anhydride may then be treated with a primary or secondary amine to yield the compound of formula (I).

c) Alternatively, the carboxylate of formula (II) may be treated with a chlorinating reagent, such as cyanuric chloride, oxalyl chloride or thionyl chloride, to give the acid chloride in situ, in an inert solvent or mixtures of solvents, such as dichloromethane or DMF, at ambient temperature. The in situ formed acid chloride is then treated with a primary or secondary amine in a one-pot procedure at ambient temperature to give a compound of formula (I).

Scheme 1

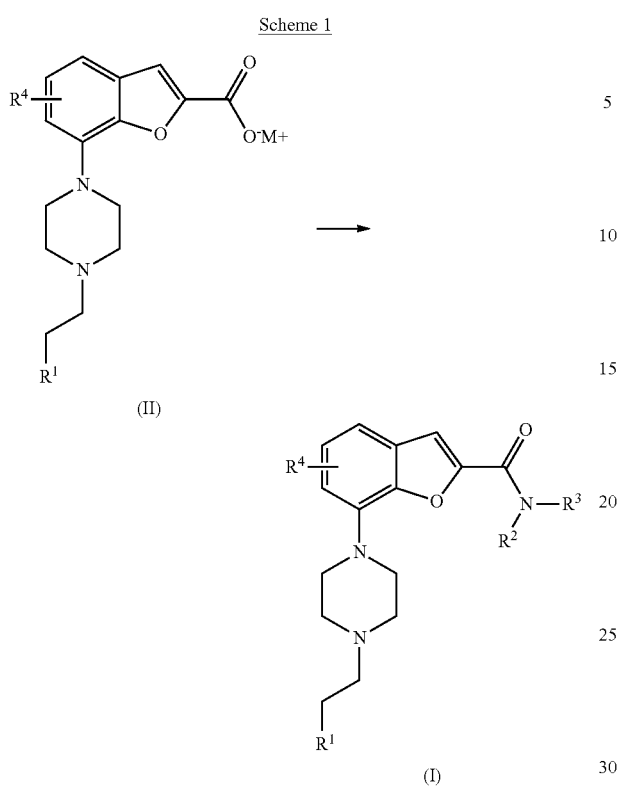

Alternatively, the compound of formula (I) may also be prepared in three different ways as outlined in Scheme 2:

d) By reacting the intermediate of formula (III) with an alkylating agent of formula (IV), where X is a leaving group such as bromide, chloride, tosylate or mesylate, together with a base such as triethylamine in an inert solvent such as acetonitrile at elevated temperature, typically at 85° C.

e) By reacting the intermediate of formula (III) with a substituted vinyl compound of formula (V), which is a known compound or may be readily prepared by one skilled in the art, in the presence of an acid, such as acetic acid, in a suitable solvent such as water, methanol, ethanol or propanol, at elevated temperature, suitably at 60-120° C. (Cliffe et al.; Tetrahedron Lett. 1991, 32, 6789).

f) By reacting the intermediate of formula (II) with an appropriate aldehyde of formula (VI) and sodium cyanoborohydride or sodium triacetoxyborohydride in a suitable solvent, such as methanol, with the optional addition of acetic acid, at room temperature or with heating up to 50° C. to obtain the compound of formula (I).

Scheme 2

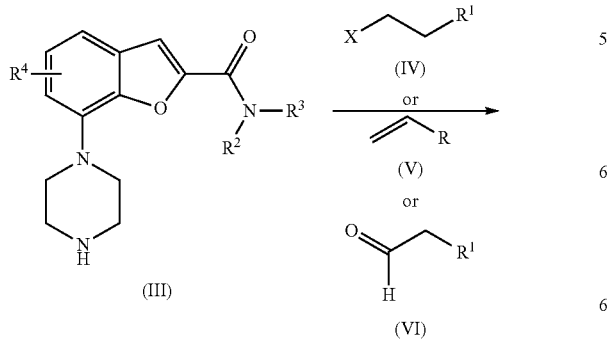

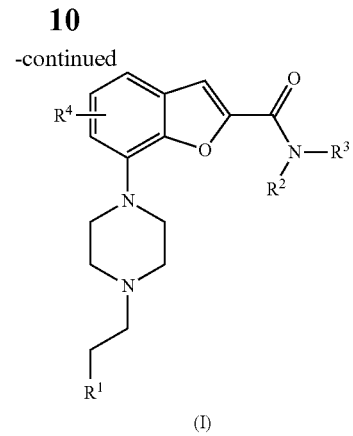

Alternatively, the compound of formula (I) may also be prepared as outlined in Scheme 3:

g) The compound of formula (I) may be synthesized via a Buchwald-Hartwig palladium catalysed amination reaction as outlined in Scheme 3. The reaction is started from a bromide of formula (VII), said bromide is reacted with a substituted piperazine moiety of formula (VIII) in an inert solvent, such as xylene, toluene or dioxane, at elevated temperature (95-110° C.) in the presence of a palladium catalyst, such as $Pd_2(dba)_3$, and a ligand, such as X-phos or BINAP, together with a base, such as potassium phosphate, cesium carbonate or sodium tert-butoxide.

Scheme 3

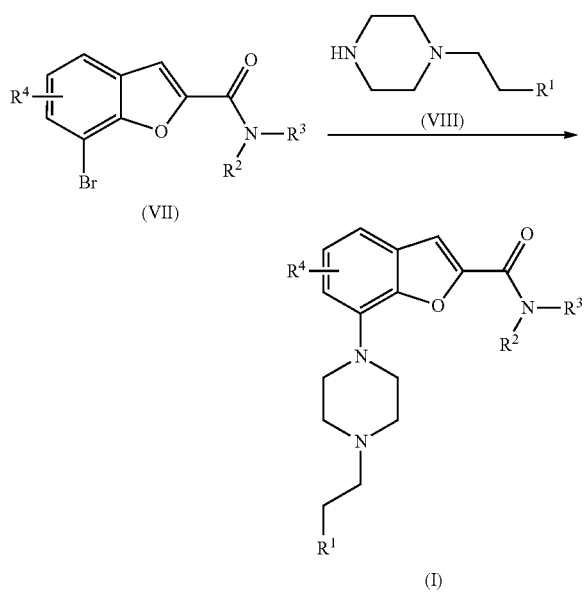

Preparation of Intermediates

The starting materials described in the Schemes are either commercially available or prepared by standard methods from known materials.

All the variables $R^1$ to $R^4$ are as defined for the compound of formula (I) above unless mentioned otherwise.

The benzofuran carboxylate of formula (II), wherein M is lithium or sodium, may be synthesised as outlined in Scheme 4. Starting from the compound of formula (IX) by treating with ethyl chloroacetate or ethyl bromoacetate and a base, such as potassium carbonate, at elevated temperature, suitably 120° C., yields the compound of formula (X). Then the intermediate of formula (XI) may be synthesized via a Buchwald-Hartwig palladium catalysed amination reaction as described for compound (I) in Scheme 3. The ester of formula (XI) may then be hydrolysed by treating it with a base, such as lithium hydroxide or sodium hydroxide, in a THF/water mixture at elevated temperature (60-100° C.) with conventional heating or in a microwave oven to obtain the carboxylate of formula (II).

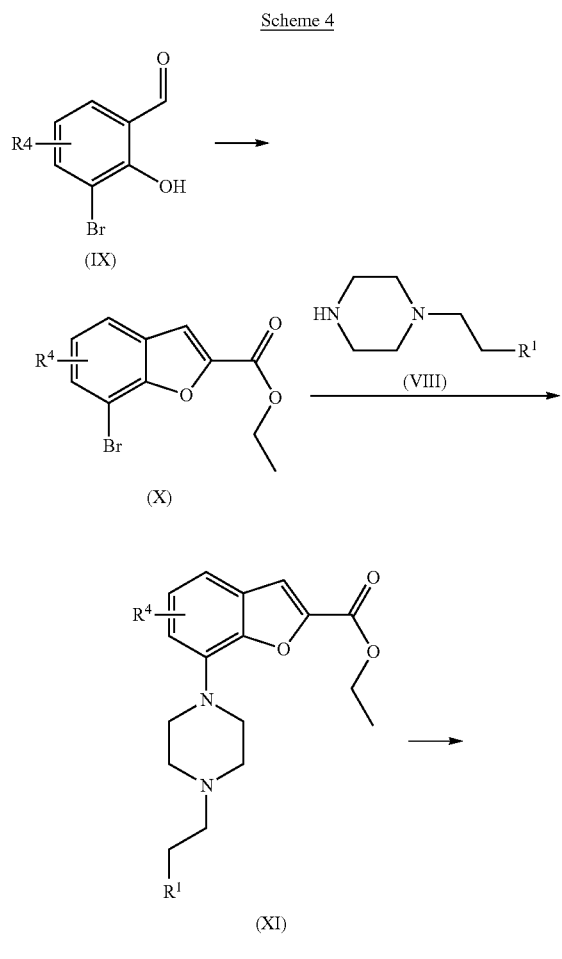

Scheme 4

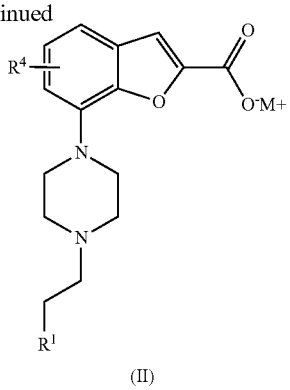

(II)

a) The intermediate bromide of formula (VII) and the intermediate of formula (III) may be prepared as outlined in Scheme 5 starting from the ester of formula (X). The compound of formula (X) may be hydrolysed by treating with a base, such as lithium hydroxide or sodium hydroxide in a THF/water mixture at elevated temperature (60-100° C.) with conventional heating or in a microwave oven to yield the carboxylate of formula (XII). The amide of formula (VII) may then be synthesized as described for compound of formula (I) in Scheme 1.

b) Alternatively, the amide of formula (VII) may be formed by treating the ester of formula (X) with an amine in the presence of DABAL-Me$_3$ in an inert solvent such as THF at elevated temperature, typically 130° C., in a microwave oven (Woodward et al.; Tetrahedron Lett. 2008, 49, 5687). The amide of formula (VII) may also be formed by treating the ester of formula (X) with an amine in the presence of catalytic amount of NaCN in a solvent such as methanol or ethanol between room temperature and 50° C. (Hoegberg et al.; J. Org. Chem. 1987, 52(10), 2033).

The protected (Pg=protecting group) intermediate of formula (XIV) may then be synthesized via a Buchwald-Hartwig palladium catalysed amination reaction as described above for compound of formula (I) in Scheme 3. The protected derivative of formula (XIV) may then readily be deprotected by one skilled in the art to give a compound of formula (III).

Scheme 5

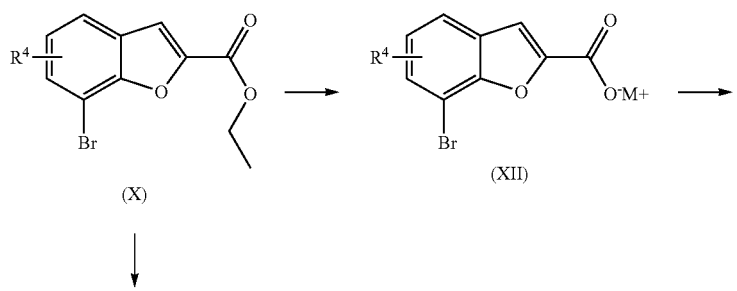

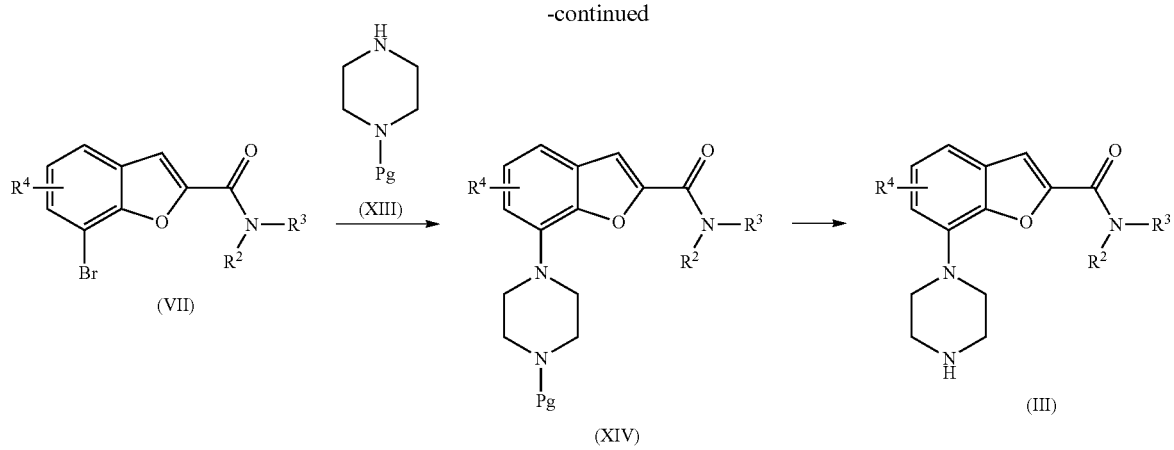

c) Alternatively, the bromide of formula (VII) may be prepared as outlined in Scheme 6, starting from a compound of formula (IX) and treating with a chloride or bromide of formula (XV), which is commercially available or readily prepared by one skilled in the art, in the presence of a base, such as potassium carbonate, in a suitable solvent such as DMA or DMF at elevated temperature, suitably at the refluxing temperature of the solvent under an inert atmosphere.

d)

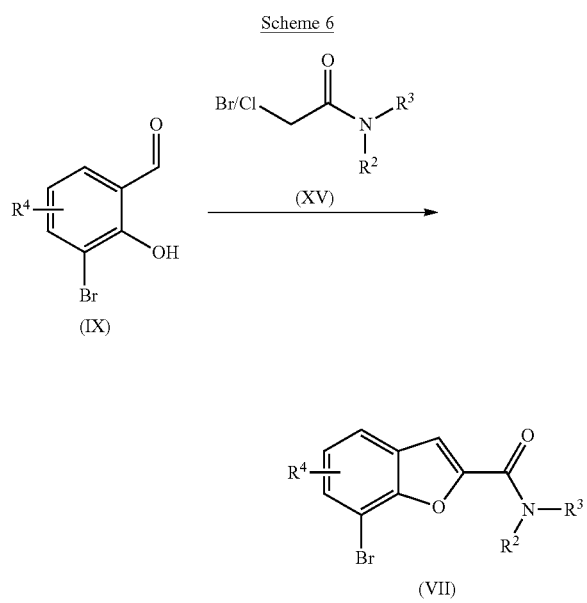

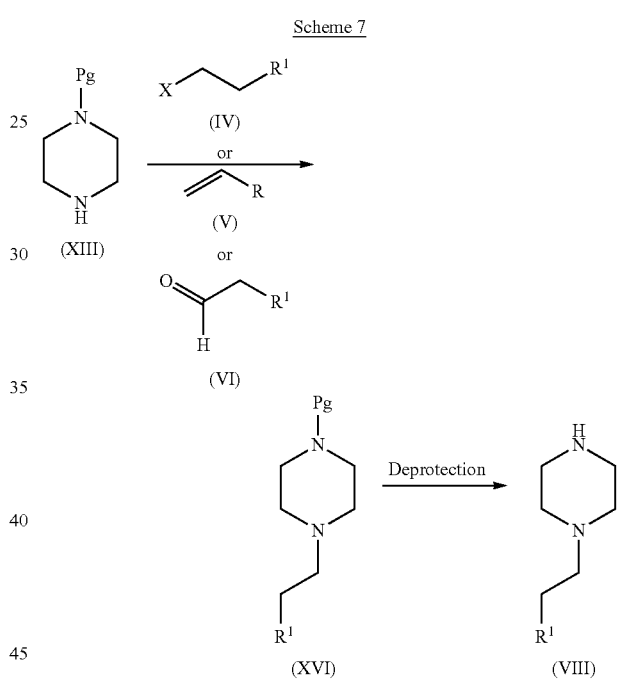

Preparation of Piperazine Substituents

The piperazine moiety of formula (VIII) may be prepared as outlined in Scheme 7. The protected piperazine of formula (XVI) (Pg=protecting group) may be prepared starting from the mono-protected piperazine of formula (XIII), which is either a known compound or can be readily prepared by one skilled in the art, in three different ways as described above for compound of formula (I) in Scheme 2.

An overall route of preparation of the compounds of formula (I) may be as described in Scheme 8.

The benzofuran carboxamide of formula (VII) may be synthesized by treating the compound of formula (IX) with a chloride or bromide of formula (XV) in the presence of a base, such as potassium carbonate, in a suitable solvent such as DMA or DMF, preferably DMA, under an inert atmosphere. The reaction mixture is heated to between about 100° C. at the reflux temperature of the solvent until the reaction is completed. The intermediate of formula (VIII) may be prepared starting from the piperazine of formula (XVII), which is either a free base or the corresponding hydrochloric salt. Excess of piperazine of formula (XVII) (e.g. 4 mole equivalents) dissolved in a suitable solvent such as water is treated with a vinyl compound of formula (V) at elevated temperature, (e.g. at about 60-70° C.) until the reaction is completed. The final compound of formula (I) may then be synthesized via a Buchwald-Hartwig palladium catalysed amination reaction. The bromide of formula (VII) is reacted with a substituted piperazine of formula (VIII) in a suitable solvent, such as toluene, xylene or dioxane, preferably xylene, in the presence of a palladium catalyst, such as Pd$_2$(dba)$_3$, and a ligand, such as X-phos or BINAP, preferably BINAP, together with a base, such as cesium carbonate, potassium phosphate or sodium tert-butoxide, preferably potassium phosphate, under an inert atmosphere. The reaction mixture is heated at between about 95° C. and the reflux temperature of the solvent, (e.g. at about 115-120° C.), until the reaction is completed.

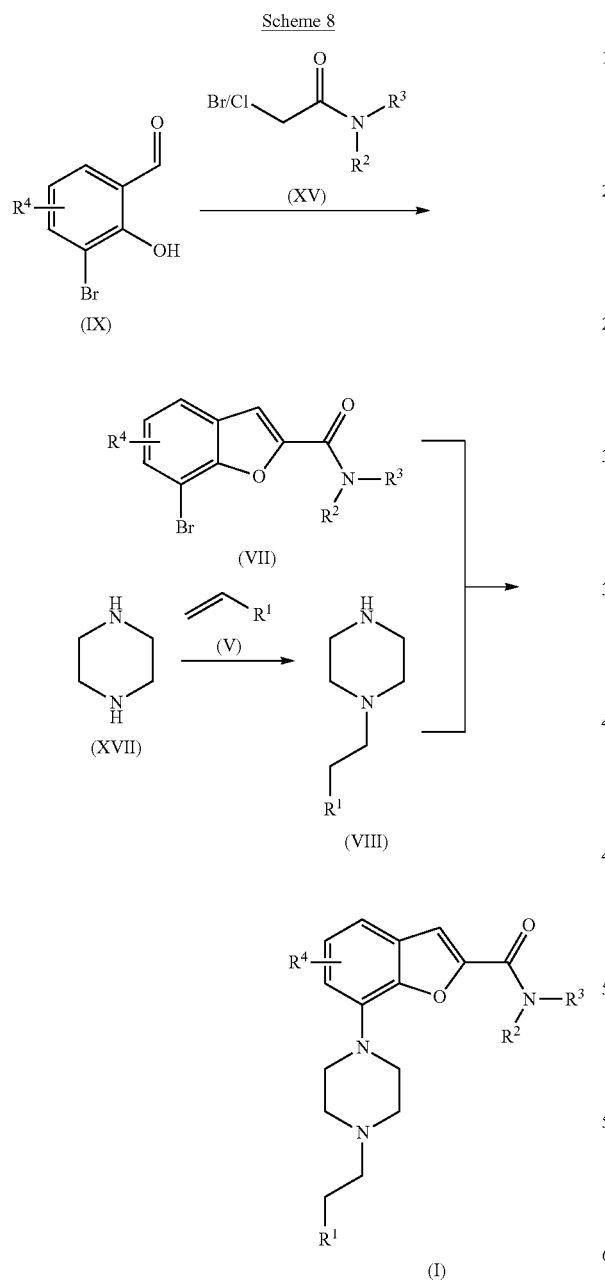

Intermediates

The present invention further relates to new intermediates and the use of these intermediates in the preparation of the compounds of formula (I) as defined hereinbefore.

In one aspect of the invention the new intermediate is a compound of formula (VII)

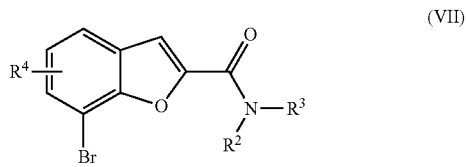

wherein R$^2$ is C$_{1-4}$alkyl, heterocyclyl, C$_{1-4}$alkylaryl, C$_{1-4}$alkylheteroaryl, carbocyclyl, C$_{1-4}$alkylheterocyclyl, heterocyclyl-heteroaryl, aryl-heterocyclyl, carbocyclyl-heteroaryl, heterocyclyl-aryl, wherein said groups the heterocyclyl, aryl, heteroaryl or carbocyclyl moiety may be optionally substituted with one or more substituents selected from halogen, C$_{1-4}$alkoxy, C(O)C$_{1-4}$alkyl, C$_{0-4}$alkylSO$_2$C$_{1-4}$alkyl, cyano, hydroxy, and C$_{1-4}$alkyl;

R$^3$ is hydrogen or C$_{1-4}$alkyl, or

R$^2$ and R$^3$ may together with the nitrogen atom, form a saturated ring system containing 4, 5 or 6 ring forming atoms selected from carbon or nitrogen and wherein said ring system is optionally substituted with one or more substituent selected from halogen, C$_{1-4}$alkyl and C$_{1-4}$alkoxy, O-heteroaryl;

R$^4$ is hydrogen, halogen, methyl or methoxy.

In one embodiment of this aspect there are provided compounds of formula (VII) wherein R$^2$ is hydrogen or C$_{1-4}$alkyl; R$^3$ is C$_{1-4}$alkyl and R$^4$ is hydrogen.

Another embodiment of this aspect there are provided compounds, said compounds being: 7-Bromo-N,N-dimethyl-benzofuran-2-carboxamide

WORKING EXAMPLES

The invention is further described by the below non-limiting examples.

Example 1

7-(4-(2-(Pyridin-2-yl)ethyl)piperazin-1-yl)-N-(pyridin-2-ylmethyl)benzofuran-2-carboxamide

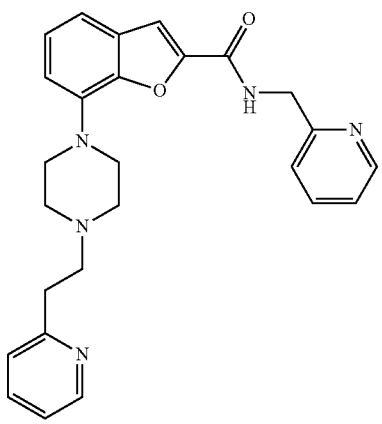 [SMILES: O=C(NCc1ccccn1)c1cc2cccc(N3CCN(CCc4ccccn4)CC3)c2o1]

Lithium 7-(4-(2-(pyridin-2-yl)ethyl)piperazin-1-yl)benzofuran-2-carboxylate (0.060 g, 0.17 mmol) was dissolved in dry DMF (1.7 mL), and then TSTU (0.064 g, 0.21 mmol) was added followed by triethylamine (0.059 mL, 0.43 mmol). The reaction was stirred for 15 min then 2-picolylamine (0.019 mL, 0.19 mmol) was added. The reaction was stirred at room temperature under argon over night. The crude product was purified by preparative LC. The fractions were combined and the acetonitrile was evaporated. DCM was added and the layers separated. The aq phase was extracted with DCM (3×). The combined organic phases were dried (Na₂SO₄), filtered and evaporated to give 37 mg (49%) of the title compound.

¹H NMR (500 MHz, chloroform-d) δ ppm 8.55-8.61 (m, 2 H), 8.03 (br. s., 1 H), 7.68-7.75 (m, 1 H), 7.61-7.67 (m, 1 H), 7.48 (s, 1 H), 7.36 (d, 1 H), 7.23-7.30 (m, 3 H), 7.21 (t, 1 H), 7.13-7.18 (m, 1 H), 6.87-6.93 (m, 1 H), 4.80 (d, 2 H), 3.45 (br. s., 4 H), 3.11 (br. s., 2 H), 2.81-3.00 (m, 6 H). MS (ES+) m/z 442.3 (M+H)⁺.

The lithium 7-(4-(2-(pyridin-2-yl)ethyl)piperazin-1-yl) benzofuran-2-carboxylate used as a starting material was prepared as follows:

Example 1a

Ethyl 7-(4-(2-(pyridin-2-yl)ethyl)piperazin-1-yl) benzofuran-2-carboxylate

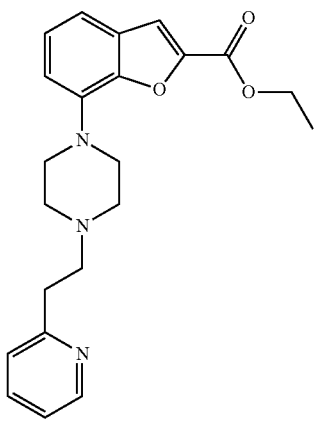 [SMILES: CCOC(=O)c1cc2cccc(N3CCN(CCc4ccccn4)CC3)c2o1]

Ethyl 7-bromobenzofuran-2-carboxylate (0.900 g, 3.34 mmol) and 1-(2-(pyridin-2-yl)ethyl)piperazine (0.672 g, 3.51 mmol) were mixed in dry degassed dioxane (13 mL). To this mixture cesium carbonate (1.417 g, 4.35 mmol), 2-dicyclohexylphosphino-2',4',6'-triisopropylbiphenyl (0.159 g, 0.33 mmol) and tris(dibenzylideneacetone)dipalladium(0) (0.153 g, 0.17 mmol) were added under argon and the reaction was heated at 95° C. over night. Water and DCM were added and the layers were separated. The aq phase was extracted with DCM (3×). The combined organic phases were washed with water, dried (MgSO₄), filtered and evaporated. The crude product was purified by flash chromatography. (SiO₂; DCM/MeOH 95/5) to give 0.507 g (40%) of the title compound.

¹H NMR (500 MHz, chloroform-d) δ ppm 8.53-8.59 (m, 1 H), 7.59-7.66 (m, 1 H), 7.50 (s, 1 H), 7.18-7.26 (m, 3 H), 7.12-7.18 (m, 1 H), 6.88 (dt, 1 H), 4.43 (q, 2 H), 3.46 (br. s., 4 H), 3.08 (br. s., 2 H), 2.72-3.00 (m, 6 H), 1.42 (t, 3 H). MS (ES+) m/z 380.2 (M+H)⁺.

Example 1b

Lithium 7-(4-(2-(pyridin-2-yl)ethyl)piperazin-1-yl) benzofuran-2-carboxylate

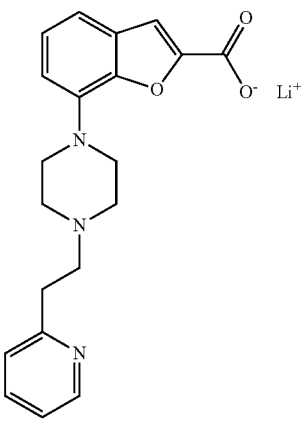 [SMILES: O=C([O-])c1cc2cccc(N3CCN(CCc4ccccn4)CC3)c2o1 ; [Li+]]

Lithium hydroxide monohydrate (102 mg, 2.42 mmol) was added to a solution of ethyl 7-(4-(2-(pyridin-2-yl)ethyl)piperazin-1-yl)benzofuran-2-carboxylate (460 mg, 1.21 mmol) in tetrahydrofuran (9.5 mL) and water (1.1 mL) and the reaction was heated at 90° C. for 30 min in a microwave oven. After cooling to room temperature the solvents were evaporated and the product was dried in vacuum over P₂O₅. The crude product was taken to the next step assuming quantitative yield. MS (ES+) m/z 352.2 (M+H)⁺.

In the examples 2-17 and 39-43 an extra equivalent of triethylamine was added when the amine starting material used in the reactions was in the form of a hydrochloride salt.

Example 2

N-(4-Morpholinophenyl)-7-(4-(2-(pyridin-2-yl) ethyl)piperazin-1-yl)benzofuran-2-carboxamide

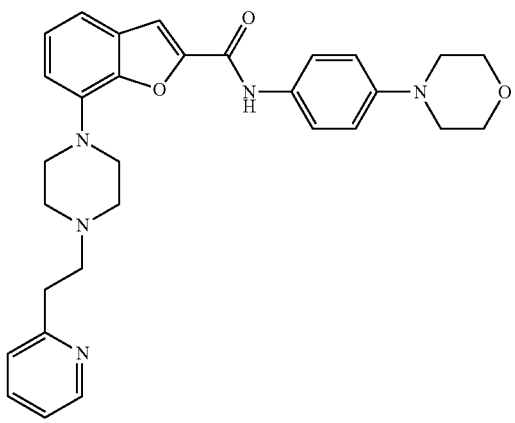 [SMILES: O=C(Nc1ccc(N2CCOCC2)cc1)c1cc2cccc(N3CCN(CCc4ccccn4)CC3)c2o1]

The compound was prepared according to the procedure disclosed in Example 1 starting from lithium 7-(4-(2-(pyridin-2-yl)ethyl)piperazin-1-yl)benzofuran-2-carboxylate (60 mg, 0.16 mmol) and 4-morpholinoaniline (37 mg, 0.20 mmol). Yield: 38 mg (44%).

¹H NMR (500 MHz, chloroform-d) δ ppm 8.57 (dt, 1 H), 8.13 (br. s., 1 H), 7.57-7.67 (m, 3 H), 7.56 (s, 1 H), 7.29-7.35 (m, 1 H), 7.21-7.27 (m, 3 H), 7.13-7.19 (m, 1 H), 6.91-6.99 (m, 3 H), 3.84-3.94 (m, 4 H), 3.41 (br. s., 3 H), 3.14-3.22 (m, 4 H), 3.09 (br. s., 2 H), 2.81-2.99 (m, 6 H). MS (ES+) m/z 512.3 (M+H)⁺.

Example 3

N-(1-Phenylpiperidin-4-yl)-7-(4-(2-(pyridin-2-yl)ethyl)piperazin-1-yl)benzofuran-2-carboxamide

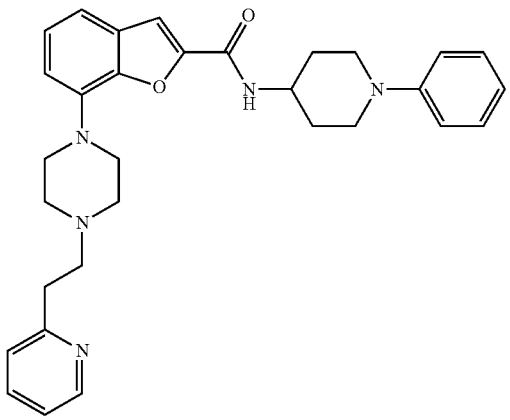 [SMILES: O=C(NC1CCN(c2ccccc2)CC1)c1cc2cccc(N3CCN(CCc4ccccn4)CC3)c2o1]

The compound was prepared according to the procedure disclosed in Example 1 starting from lithium 7-(4-(2-(pyridin-2-yl)ethyl)piperazin-1-yl)benzofuran-2-carboxylate (70 mg, 0.18 mmol) and 1-phenylpiperidin-4-amine (39 mg, 0.22 mmol). Yield: 34 mg (34%).

¹H NMR (500 MHz, chloroform-d) δ ppm 8.55-8.58 (m, 1 H), 7.64 (ddd, 1 H), 7.48 (s, 1 H), 7.27-7.32 (m, 6 H), 7.20-7.26 (m, 2 H), 7.13-7.18 (m, 1 H), 6.99 (dd, 2 H), 6.90-6.95 (m, 1 H), 6.88 (t, 1 H), 6.44 (br. s., 1 H), 4.16-4.26 (m, 1 H), 3.67-3.74 (m, 2 H), 3.38 (br. s., 4 H), 3.07 (br. s., 2 H), 2.94-3.02 (m, 2 H), 2.78-2.94 (m, 6 H), 2.14-2.23 (m, 2 H), 1.68-1.83 (m, 2 H). MS (ES+) m/z 510.4 (M+H)⁺.

Example 4

N-(4-(Methylsulfonyl)benzyl)-7-(4-(2-(pyridin-2-yl)ethyl)piperazin-1-yl)benzofuran-2-carboxamide

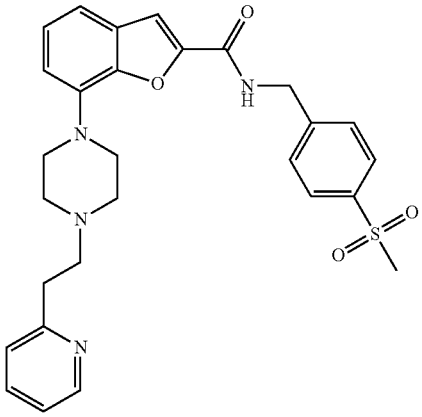 [SMILES: CS(=O)(=O)c1ccc(CNC(=O)c2cc3cccc(N4CCN(CCc5ccccn5)CC4)c3o2)cc1]

The compound was prepared according to the procedure disclosed in Example 1 starting from lithium 7-(4-(2-(pyridin-2-yl)ethyl)piperazin-1-yl)benzofuran-2-carboxylate (60 mg, 0.16 mmol) and 4-methylsulphonylbenzylamine hydrochloride (42 mg, 0.19 mmol).

Yield: 38 mg (43%).

¹H NMR (500 MHz, chloroform-d) δ ppm 8.55 (dt, 1 H), 7.94 (d, 2 H), 7.56-7.69 (m, 3 H), 7.53 (s, 1 H), 7.30 (br. s., 1 H), 7.20-7.25 (m, 2 H), 7.12-7.19 (m, 1 H), 6.95 (br. s., 2 H), 4.80 (d, 2 H), 3.38 (br. s., 4 H), 3.00-3.15 (m, 5 H), 2.72-2.97 (m, 6 H). MS (ES+) m/z 519.3 (M+H)⁺.

Example 5

N-((1-Methyl-1H-imidazol-4-yl)methyl)-7-(4-(2-(pyridin-2-yl)ethyl)piperazin-1-yl)benzofuran-2-carboxamide

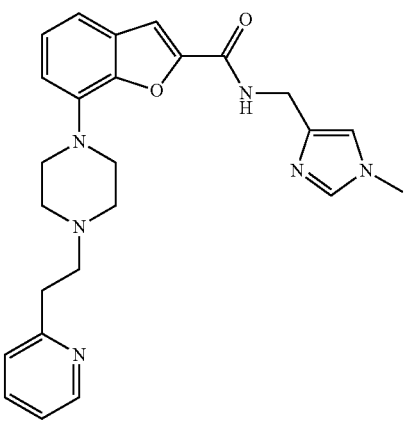 [SMILES: Cn1cnc(CNC(=O)c2cc3cccc(N4CCN(CCc5ccccn5)CC4)c3o2)c1]

The compound was prepared according to the procedure disclosed in Example 1 starting from lithium 7-(4-(2-(pyridin-2-yl)ethyl)piperazin-1-yl)benzofuran-2-carboxylate (70 mg, 0.18 mmol) and (1-methyl-1H-imidazol-4-yl)methylamine (24 mg, 0.22 mmol). Yield: 42 mg (48%).

¹H NMR (500 MHz, chloroform-d) δ ppm 8.56 (d, 1 H), 7.63 (t, 1 H), 7.45 (s, 1 H), 7.40 (s, 1 H), 7.23-7.26 (m, 2 H), 7.11-7.22 (m, 3 H), 6.93 (s, 1 H), 6.88 (d, 1 H), 4.58 (d, 2 H), 3.68 (s, 3 H), 3.41 (br. s., 4 H), 3.12 (br. s., 2 H), 2.78-3.02 (m, 6 H). MS (ES+) m/z 445.3 (M+H)⁺.

Example 6

N-(1-Acetylpiperidin-4-yl)-7-(4-(2-(pyridin-2-yl)ethyl)piperazin-1-yl)benzofuran-2-carboxamide

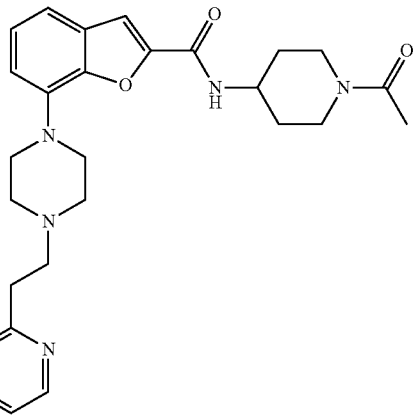

The compound was prepared according to the procedure disclosed in Example 1 starting from lithium 7-(4-(2-(pyridin-2-yl)ethyl)piperazin-1-yl)benzofuran-2-carboxylate (60 mg, 0.16 mmol) and 1-(4-amino-piperidin-1-yl)-ethanone (27 mg, 0.19 mmol). Yield: 39 mg (47%).

$^1$H NMR (500 MHz, chloroform-d) δ ppm 8.53-8.59 (m, 1 H), 7.63 (tt, 1 H), 7.44-7.49 (m, 1 H), 7.19-7.33 (m, 3 H), 7.12-7.18 (m, 1 H), 6.93 (d, 1 H), 6.32-6.41 (m, 1 H), 4.64 (d, 1 H), 4.18-4.30 (m, 1 H), 3.87 (d, 1 H), 3.37 (br. s., 4 H), 3.25 (t, 1 H), 3.08 (br. s., 2 H), 2.88-2.98 (m, 2 H), 2.74-2.88 (m, 5 H), 2.12-2.23 (m, 4 H), 2.09 (d, 1 H), 1.42-1.56 (m, 2H). MS (ES+) m/z 476.1 (M+H)$^+$.

Example 7

N-(1-(Pyridin-2-yl)ethyl)-7-(4-(2-(pyridin-2-yl)ethyl)piperazin-1-yl)benzofuran-2-carboxamide

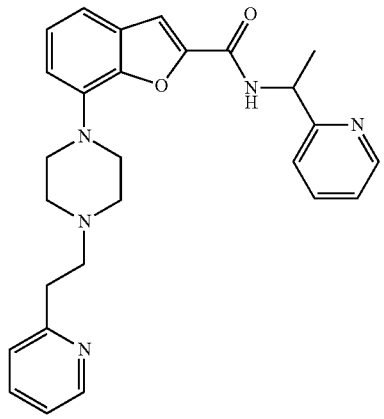 [SMILES: CC(NC(=O)c1cc2cccc(N3CCN(CCc4ccccn4)CC3)c2o1)c1ccccn1]

The compound was prepared according to the procedure disclosed in Example 1 starting from lithium 7-(4-(2-(pyridin-2-yl)ethyl)piperazin-1-yl)benzofuran-2-carboxylate (60 mg, 0.16 mmol) and 1-(pyridin-2-yl)ethanamine (23 mg, 0.19 mmol). Yield: 20 mg (25%).

$^1$H NMR (400 MHz, chloroform-d) δ ppm 8.56-8.60 (m, 2H), 8.38 (d, 1 H), 7.71 (td, 1 H), 7.64 (td, 1 H), 7.45 (s, 1 H), 7.31 (dt, 1 H), 7.14-7.28 (m, 5 H), 6.88 (dt, 1 H), 5.31 (quin, 1 H), 3.39-3.53 (m, 4 H), 3.09-3.16 (m, 2 H), 2.87-3.00 (m, 6 H), 1.62 (d, 3 H). MS (ES+) m/z 456.3 (M+H)$^+$.

Example 8

N-(1-(3-Chloropyridin-2-yl)piperidin-4-yl)-7-(4-(2-(pyridin-2-yl)ethyl)piperazin-1-yl)benzofuran-2-carboxamide

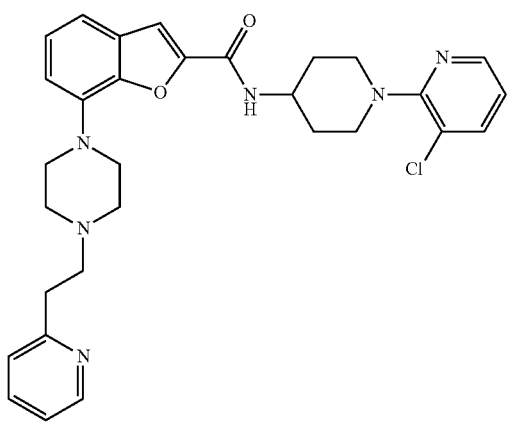

The compound was prepared according to the procedure disclosed in Example 1 starting from lithium 7-(4-(2-(pyridin-2-yl)ethyl)piperazin-1-yl)benzofuran-2-carboxylate (80 mg, 0.21 mmol) and 1-(3-chloropyridin-2-yl)piperidin-4-amine (57 mg, 0.27 mmol). Yield: 50 mg (40%).

$^1$H NMR (400 MHz, acetonitrile-d$_3$) δ ppm 8.48 (ddd, 1 H), 8.19 (dd, 1 H), 7.62-7.71 (m, 2H), 7.37 (s, 1 H), 7.23-7.30 (m, 2 H), 7.20 (t, 1 H), 7.16 (ddd, 1 H), 7.08 (d, 1 H), 6.88-6.94 (m, 2 H), 4.05-4.18 (m, 1 H), 3.76-3.85 (m, 2 H), 3.27-3.35 (m, 4 H), 2.91-3.01 (m, 4 H), 2.77-2.83 (m, 2 H), 2.70-2.77 (m, 4 H), 1.99-2.07 (m, 2 H), 1.79-1.91 (m, 2 H). MS (ES+) m/z 545.3 (M+H)$^+$.

Example 9

N-(4-Cyanobenzyl)-7-(4-(2-(pyridin-2-yl)ethyl)piperazin-1-yl)benzofuran-2-carboxamide

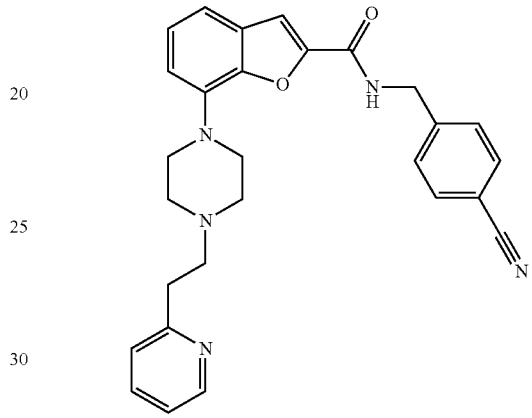

The compound was prepared according to the procedure disclosed in Example 1 starting from lithium 7-(4-(2-(pyridin-2-yl)ethyl)piperazin-1-yl)benzofuran-2-carboxylate (80 mg, 0.21 mmol) and 4-(aminomethyl)benzonitrile (30 mg, 0.22 mmol). Yield: 66 mg (63%).

$^1$H NMR (400 MHz, acetonitrile-d$_3$) δ ppm 8.48 (ddd, 1H), 7.85 (t, 1 H), 7.67-7.72 (m, 2 H), 7.65 (td, 1 H), 7.50-7.56 (m, 2 H), 7.41 (s, 1 H), 7.24-7.29 (m, 2 H), 7.20 (t, 1 H), 7.15 (ddd, 1 H), 6.90 (dd, 1 H), 4.64 (d, 2 H), 3.30-3.32 (m, 4 H), 2.94-2.98 (m, 2 H), 2.76-2.79 (m, 2 H), 2.70-2.72 (m, 4 H). MS (ES+) m/z 467 (M+H)$^+$.

Example 10

N-(Benzo[d][1,3]dioxol-5-ylmethyl)-7-(4-(2-(pyridin-2-yl)ethyl)piperazin-1-yl)benzofuran-2-carboxamide

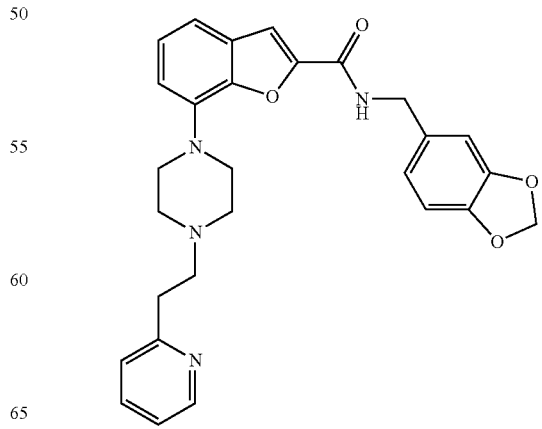

The compound was prepared according to the procedure disclosed in Example 1 starting from lithium 7-(4-(2-(pyridin-2-yl)ethyl)piperazin-1-yl)benzofuran-2-carboxylate (80 mg, 0.21 mmol) and benzo[d][1,3]dioxol-5-ylmethaneamine (41 mg, 0.27 mmol). Yield: 78 mg (72%).

$^1$H NMR (400 MHz, acetonitrile-d$_3$) δ ppm 8.45-8.50 (m, 1 H), 7.67-7.74 (m, 1 H), 7.65 (td, 1 H), 7.38 (s, 1 H), 7.23-7.30 (m, 2 H), 7.20 (d, 1 H), 7.12-7.18 (m, 1 H), 6.83-6.92 (m, 3 H), 6.77-6.82 (m, 1 H), 5.93 (s, 2 H), 4.48 (d, 2 H), 3.25-3.36 (m, 4 H), 2.97 (t, 2 H), 2.78 (t, 2 H), 2.67-2.75 (m, 4 H). MS (ES+) m/z 486 (M+H)$^+$.

Example 11

N,N-Dimethyl-7-(4-(2-(pyridin-2-yl)ethyl)piperazin-1-yl)benzofuran-2-carboxamide

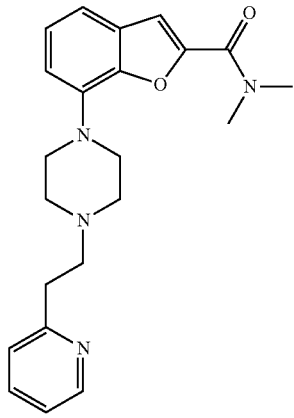 [SMILES: CN(C)C(=O)c1cc2cccc(N3CCN(CCc4ccccn4)CC3)c2o1]

The compound was prepared according to the procedure disclosed in Example 1 starting from lithium 7-(4-(2-(pyridin-2-yl)ethyl)piperazin-1-yl)benzofuran-2-carboxylate (80 mg, 0.21 mmol) and dimethylamine hydrochloride (91 mg, 1.1 mmol). Yield: 55 mg (65%).

$^1$ H NMR (500 MHz, acetonitrile-d$_3$, 55° C.) δ ppm 8.47-8.50 (m, 1 H), 7.65-7.69 (m, 1 H), 7.28 (dt, 1 H), 7.24-7.27 (m, 2 H), 7.16-7.22 (m, 2 H), 6.88 (dt, 1 H), 3.34 (br. s., 4 H), 3.29 (s, 3 H), 2.98-3.08 (m, 5 H), 2.68-2.98 (m, 6 H). MS (ES+) m/z 378.8 (M+H)$^+$.

An alternative method to prepare the title compound of Example 11 is as follows: To a solution of 1-[2-(2-pyridyl)ethyl]piperazine (23.2 g, 121 mmol in xylene solution) was added potassium phosphate (60.6 g, 280 mmol), Pd$_2$ (dba)$_3$ (6.78 g, 7.4 mmol) and BINAP (6.98 g, 11.2 mmol). The suspension was heated to 90-100° C. and then 7-bromo-N,N-dimethyl-benzofuran-2-carboxamide (25.0 g, 93.2 mmol in xylene solution) was added over a period of 30-45 min at 90-100° C. The reaction mixture was then heated at 115-120° C. for 12 to 16 h. The reaction mixture was cooled to 40-50° C. Ethyl acetate (100 mL) was added and the mixture cooled to 25-30° C. The mixture was filtered through celite and the celite washed with ethyl acetate (50 mL). Water (200 mL) was added to the filtrate and the pH adjusted to 2.0 to 2.5 with an aqueous solution of hydrochloric acid (30.0% v/v) at 20-25° C. The solution was stirred for 15-20 min and then filtered through celite and the celite washed with water (50 mL). N,N-Dimethyl acetamide (12.5 mL) was added and the resulting solution stirred for 10-20 min. The aqueous layer was separated and washed with ethyl acetate (2×200 mL). To the aqueous layer, ethyl acetate (300 mL) was added and adjusted to pH 8.5-9.0 with an aqueous solution of potassium carbonate (10.0% w/w) at 20-25° C. The organic layer was separated and the aqueous layer was extracted with ethyl acetate (300 mL). The combined organic layers were washed with an aqueous solution of potassium carbonate (5.0% w/w) followed by water (125 mL). The organic layer was concentrated in vacuo at 40-45° C. until residual volume reached 75 mL. To the suspension was added t-butyl methyl ether (250 mL) over a period of 15-20 min at 40-45° C. The solvent was concentrated in vacuo at 40-45° C. until residual volume reached 100 mL. The suspension was cooled to 20-25° C. and stirred for 1-2 h and then the product was collected by filtration. Yield: 54% w/w.

The product (5.0 g, 13.2 mmol) was recrystallized from 2-propanol (25 mL) by heating to 70-75° C. to get a clear dissolution. Then the solution was allowed to cool to 20-25° C. for crystallization. The suspension was then cooled to 10-15° C. and stirred for 2-4 h. The product was collected by filtration. Yield: 80% w/w. $^1$ H NMR (400 MHz, chloroform-d) δ 8.47 (1H, d); 7.54 (1H, dt), 7.25 (1H, s), 7.17-7.05 (4H, m), 6.76 (1H, d), 3.34-3.30 (7H, m), 3.08 (3H, br s), 3.01-2.97 (2H, m), 2.82-2.78 (2H, m), 2.72 (4H, t).

The solid product was analysed by X-ray powder diffraction (XRPD) showing that it is crystalline.

The crystallinity were analysed using the XRPD instrumentation as described below. The following diffractions, with measured angles given as °2θ (Cu Kα) are shown.

The significant measured angles given as °2θ (Cu Kα) are: 5.48, 9.36, 10.54, 18.32, 19.85 and 21.93.

Even more significant measured angles given as °2θ (Cu Kα) are: 5.48 and 9.36.

X-Ray Powder Diffraction (XRPD) patterns were collected on a PANalytical X'Pert PRO MPD theta-theta system using Cu Kα-radiation. Thin flat samples were prepared on flat silicon zero background plates. The plates were mounted in sample holders and rotated in a horizontal position during measurement. Diffraction patterns were collected between 2°2θ (theta) and 40°2θ (theta) in a continuous scan mode. The skilled person of X-ray powder diffraction will realize that the relative intensity of peaks may be affected by, for example, grains above approximately 30 micrometer in size and non-unitary aspect ratios, which may affect analysis of samples. Furthermore, it should be understood that intensities might fluctuate depending on experimental conditions and sample preparation such as preferred orientation of the particles in the sample. The use of automatic or fixed divergence slits will also influence the relative intensity calculations. A person skilled in the art may handle such effects when comparing diffraction patterns.

It will be appreciated that the skilled person in the art will also realize that the position of reflections may be affected by the precise height at which the sample sits in the diffractometer, temperature and the zero calibration of the diffractometer. The surface planarity of the sample may also have a small effect. The exact value for the position of a reflection may vary slightly between samples, e.g. due to differences in crystallinity of the material. The use of automatic peak finding programs or manual, subjective, peak determination may also slightly affect the reported position of a reflection. It is obvious for the skilled person that differences in instrument performance may influence peak resolution. Hence the diffraction pattern data presented are not to be taken as absolute values.

Generally, a measurement error of a diffraction angle in an X-ray powder diffractogram is about 5% or less, in particular within the range plus 0.5°2θ to minus 0.5°2θ when using Cu Kα-radiation, and such degree of a measurement error should be taken into account when considering the X-ray powder diffraction peaks.

The 7-bromo-N,N-dimethyl-benzofuran-2-carboxamide used as a starting material in the alternative method was prepared as follows:

Example 11a

7-Bromo-N,N-dimethyl-benzofuran-2-carboxamide

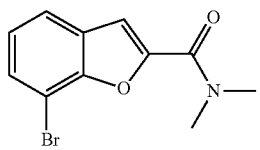

Potassium carbonate (86.8 g, 622 mmol) and 2-chloroacetamide (40.5 g, 323 mmol) were added to a solution of 3-bromo-2-hydroxy-benzaldehyde (50.5 g, 249 mmol) in N,N-dimethyl acetamide (250 mL). The mixture was heated at 125-130° C. for a period of 20-25 h under a nitrogen atmosphere. The reaction mixture was cooled to 10-20° C. Water (1 L) was added for a period of 30-45 minutes at 10-20° C. The reaction solution was heated to 25-28° C. and extracted with xylene twice (2×400 mL). The combined organic layers were washed with an aqueous solution of potassium carbonate (5.0% w/w). The organic layer was separated and filtered through celite and washed with xylene (100.0 mL). The solvent was concentrated in vacuo until the residual volume became 150 mL. More xylene (150 mL) was added at 80-85° C. and then cooled to 20-25° C. This solution was used in the next stage without isolation of the product.

7-bromo-N,N-dimethyl-benzofuran-2-carboxamide was also prepared as follows: A mixture of 3-bromo-2-hydroxybenzaldehyde (5 g, 24.87 mmol), 2-chloro-N,N-dimethylacetamide (3.33 ml, 32.34 mmol) and potassium carbonate (6.88 g, 49.75 mmol) in DMF (60 ml) was heated at reflux for 1 h. The solids were filtered off and the filtrate was concentrated. The residue was taken up in ethyl acetate and washed with sat. NaCl(aq). The layers were separated and the aqueous layer was extracted with ethyl acetate (2×50 mL). The combined organic layer was dried with sodium sulfate, filtered and concentrated to give the title compound (6.63 g, 99%) as a crude product which was used as such in subsequent reaction.

$^1$H NMR (400 MHz, acetonitrile-$d_3$) δ ppm 7.69 (dd, 1 H) 7.60 (dd, 1 H) 7.33 (s, 1 H) 7.23 (t, 1 H) 3.28 (br. s., 3 H) 3.06 (br. s., 3 H). MS (ES+) m/z 270.0 (M+H)$^+$.

The 1-[2-(2-pyridyl)ethyl]piperazine used as a starting material in the alternative method was prepared as follows:

Example 11b

1-[2-(2-Pyridyl)ethyl]piperazine

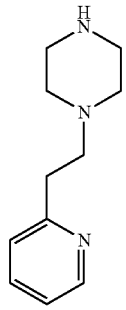 [SMILES: c1ccc(CCN2CCNCC2)nc1]

A solution of piperazine:2HCl:H$_2$O (241 g, 1332 mmol) in water (245 mL) was heated at 60-70° C. Vinyl pyridine (38.0 g, 333 mmol) was slowly added during of 45-60 min at 60-70° C. Heating was continued for 45-60 min at 60-70° C. The reaction mixture was cooled to 20-25° C. The pH was slowly adjusted to 8.0-8.5 with a solution of aqueous sodium hydroxide (40.0% w/w) during 45-60 min at 20-30° C. The reaction mixture was washed with toluene (2×175 mL). The aqueous layer was slowly adjusted to pH 12.0-12.5 with a solution of aqueous NaOH (40.0% w/w) during 45-60 min at 20-30° C. and again washed with toluene (175 mL). The aqueous layer was extracted with n-butanol (2×210 mL). n-Butanol was removed under reduced pressure until the residual volume reached 100 mL. n-Butanol was swapped completely with xylene (2×210 mL) until the residual volume reached 100 mL. Xylene (35 mL) was added at 75-85° C. and then cooled to 20-25° C. The reaction solution was maintained for 1.0 h at 20-25° C. and then filtered through celite and the celite washed with xylene (35 mL). The combined xylene solution was used in the next step without isolation of the product.

Example 12

N-Methyl-7-(4-(2-(pyridin-2-yl)ethyl)piperazin-1-yl) benzofuran-2-carboxamide

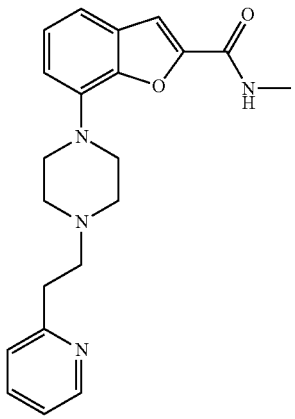 [SMILES: CNC(=O)c1cc2cccc(N3CCN(CCc4ccccn4)CC3)c2o1]

The compound was prepared according to the procedure disclosed in Example 1 starting from lithium 7-(4-(2-(pyridin-2-yl)ethyl)piperazin-1-yl)benzofuran-2-carboxylate (80 mg, 0.21 mmol) and methylamine hydrochloride (90 mg, 1.3 mmol). Yield: 50 mg (62%).

$^1$H NMR (400 MHz, acetonitrile-$d_3$) δ ppm 8.47-8.51 (m, 1 H), 7.66 (td, 1 H), 7.33 (s, 1 H), 7.27-7.30 (m, 1 H), 7.23-7.26 (m, 1 H), 7.14-7.22 (m, 3 H), 6.89 (dd, 1 H), 3.33 (br. s., 4H), 2.97-3.04 (m, 2 H), 2.90 (d, 3 H), 2.70-2.88 (m, 6 H). MS (ES+) m/z 365.2 (M+H)$^+$.

Example 13

N-Cyclopropyl-7-(4-(2-(pyridin-2-yl)ethyl)piperazin-1-yl)benzofuran-2-carboxamide

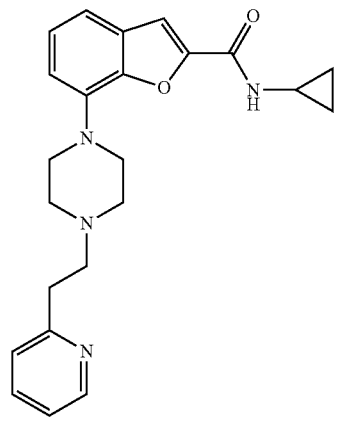 [SMILES: O=C(NC1CC1)c1cc2cccc(N3CCN(CCc4ccccn4)CC3)c2o1]

The compound was prepared according to the procedure disclosed in Example 1 starting from lithium 7-(4-(2-(pyridin-2-yl)ethyl)piperazin-1-yl)benzofuran-2-carboxylate (80 mg, 0.21 mmol) and cyclopropylamine (64 mg, 1.1 mmol). Yield: 50 mg (57%).

$^1$H NMR (500 MHz, acetonitrile-d$_3$) δ ppm 8.49 (dt, 1H), 7.66 (td, 1 H), 7.34 (s, 1 H), 7.26-7.30 (m, 1 H), 7.22-7.25 (m, 1 H), 7.14-7.21 (m, 3 H), 6.89 (dd, 1 H), 3.27-3.32 (m, 4 H), 2.96-3.00 (m, 2 H), 2.77-2.85 (m, 3 H), 2.70-2.74 (m, 4 H), 0.76-0.81 (m, 2 H), 0.64-0.69 (m, 2 H). MS (ES+) m/z 391.2 (M+H)$^+$.

Example 14

N-(3,3-Difluorocyclobutyl)-7-(4-(2-(pyridin-2-yl)ethyl)piperazin-1-yl)benzofuran-2-carboxamide

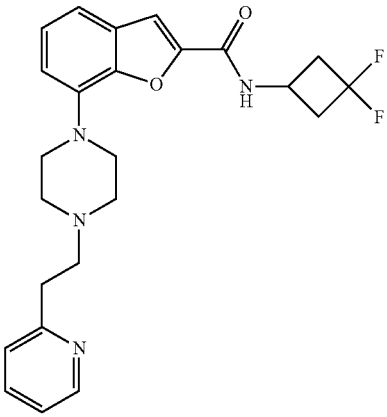 [SMILES: O=C(NC1CC(F)(F)C1)c1cc2cccc(N3CCN(CCc4ccccn4)CC3)c2o1]

The compound was prepared according to the procedure disclosed in Example 1 starting from lithium 7-(4-(2-(pyridin-2-yl)ethyl)piperazin-1-yl)benzofuran-2-carboxylate (80 mg, 0.21 mmol) and 3,3-difluorocyclobutanamine hydrochloride (48 mg, 0.34 mmol). Yield: 63 mg (64%).

$^1$H NMR (500 MHz, acetonitrile-d$_3$) δ ppm 8.47-8.51 (m, 1 H), 7.66 (td, 1 H), 7.46 (d, 1 H), 7.39 (s, 1 H), 7.28 (dt, 1 H), 7.24-7.27 (m, 1 H), 7.20 (t, 1 H), 7.14-7.18 (m, 1 H), 6.89-6.92 (m, 1 H), 4.33-4.43 (m, 1 H), 3.29-3.34 (m, 4 H), 2.94-3.04 (m, 4 H), 2.78-2.90 (m, 4 H), 2.72-2.76 (m, 4 H). MS (ES+) m/z 441.3 (M+H)$^+$.

Example 15

Azetidin-1-yl(7-(4-(2-(pyridin-2-yl)ethyl)piperazin-1-yl)benzofuran-2-yl)methanone

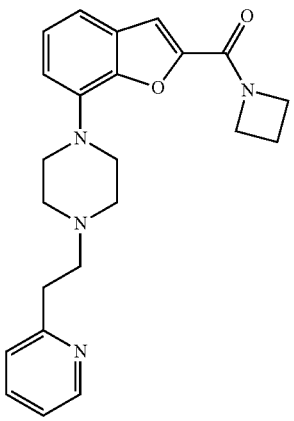 [SMILES: O=C(c1cc2cccc(N3CCN(CCc4ccccn4)CC3)c2o1)N1CCC1]

The compound was prepared according to the procedure disclosed in Example 1 starting from lithium 7-(4-(2-(pyridin-2-yl)ethyl)piperazin-1-yl)benzofuran-2-carboxylate (80 mg, 0.21 mmol) and azetidine hydrochloride (84 mg, 0.90 mmol). Yield: 41 mg (47%).

$^1$H NMR (400 MHz, acetonitrile-d$_3$) δ ppm 8.48 (ddd, 1 H), 7.65 (td, 1 H), 7.31 (s, 1 H), 7.26-7.29 (m, 1 H), 7.23-7.26 (m, 1 H), 7.14-7.21 (m, 2 H), 6.87 (dd, 1 H), 4.63 (t, 2 H), 4.12 (t, 2 H), 3.25-3.31 (m, 4 H), 2.94-2.99 (m, 2 H), 2.76-2.81 (m, 2 H), 2.68-2.73 (m, 4 H), 2.34-2.44 (m, 2 H). MS (ES+) m/z 391.0 (M+H)$^+$.

Example 16

(7-(4-(2-(Pyridin-2-yl)ethyl)piperazin-1-yl)benzofuran-2-yl)(pyrrolidin-1-yl)methanone

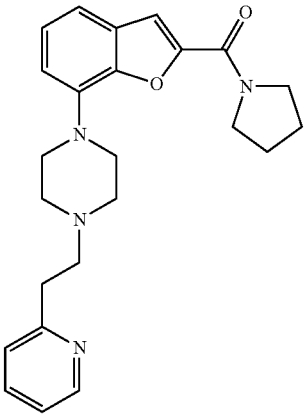 [SMILES: O=C(c1cc2cccc(N3CCN(CCc4ccccn4)CC3)c2o1)N1CCCC1]

The compound was prepared according to the procedure disclosed in Example 1 starting from lithium 7-(4-(2-(pyridin-2-yl)ethyl)piperazin-1-yl)benzofuran-2-carboxylate (90 mg, 0.24 mmol) and pyrrolidine (54 mg, 0.76 mmol). Yield: 68 mg (66%).

$^1$H NMR (500 MHz, acetonitrile-d$_3$) δ ppm 8.47-8.50 (m, 1H), 7.65 (td, 1 H), 7.33 (s, 1 H), 7.28 (dt, 1 H), 7.23-7.26 (m, 1 H), 7.19 (t, 1 H), 7.16 (ddd, 1 H), 6.87 (dd, 1 H), 3.91 (t, 2 H), 3.57 (t, 2 H), 3.28-3.33 (m, 4 H), 2.95-3.00 (m, 2 H), 2.77-2.81 (m, 2 H), 2.69-2.73 (m, 4 H), 1.97-2.04 (m, 2 H), 1.86-1.93 (m, 2 H). MS (ES+) m/z 405.3 (M+H)$^+$.

Examples 17-37

Lithium 7-(4-(2-(pyridin-2-yl)ethyl)piperazin-1-yl)benzofuran-2-carboxylate (0.040 g, 0.11 mmol)×24 (0.960 g) was suspended in dry DMF (19.2 mL), TSTU (1.01 g) was added followed by triethylamine (0.94 mL). The reaction was stirred for 15 min before the reaction solution was divided and added to 24 different amines (each amine was pre-dissolved in 200 μL of dry DMF, and to the hydrochlorides extra triethylamine was added in respective well). The plate was shaken at room temperature over night. The residues were filtered into a 48 well microtiterplate and the filter wells washed with 250 μL of dry DMF. The plate was then purified by preparative HPLC. 21 of the products of these reactions are described in examples 17-37.

Example 17

N-(4-(Methylsulfonylmethyl)benzyl)-7-(4-(2-(pyridin-2-yl)ethyl)piperazin-1-yl)benzofuran-2-carboxamide

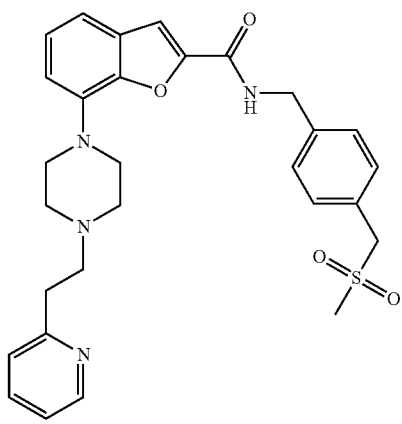 [SMILES: CS(=O)(=O)Cc1ccc(CNC(=O)c2cc3cccc(N4CCN(CCc5ccccn5)CC4)c3o2)cc1]

Yield: 43%

¹H NMR (500 MHz, acetonitrile-d₃) δ ppm 8.47-8.49 (m, 1 H), 7.77 (t, 1 H), 7.65 (td, 1 H), 7.37-7.44 (m, 5 H), 7.24-7.29 (m, 2 H), 7.20 (t, 1 H), 7.15 (ddd, 1 H), 6.90 (dd, 1 H), 4.61 (d, 2 H), 4.30 (s, 2 H), 3.29-3.34 (m, 4 H), 2.97 (t, 2H), 2.76-2.81 (m, 5H), 2.70-2.74 (m, 4H). MS (ES+) m/z 533.3 (M+H)⁺

Example 18

N-(3-Methoxyphenethyl)-7-(4-(2-(pyridin-2-yl)ethyl)piperazin-1-yl)benzofuran-2-carboxamide

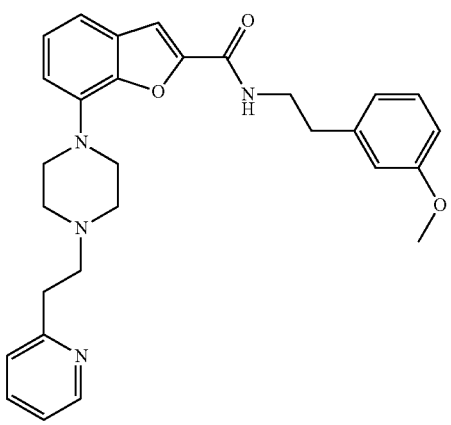 [SMILES: COc1cccc(CCNC(=O)c2cc3cccc(N4CCN(CCc5ccccn5)CC4)c3o2)c1]

Yield: 49%

¹H NMR (500 MHz, acetonitrile-d₃) δ ppm 8.49 (ddd, 1 H), 7.66 (td, 1 H), 7.33 (s, 1 H), 7.28-7.31 (m, 1 H), 7.21-7.25 (m, 2 H), 7.15-7.21 (m, 3 H), 6.88 (dd, 1 H), 6.83-6.87 (m, 2 H), 6.78-6.81 (m, 1 H), 3.75 (s, 3 H), 3.63 (q, 2 H), 3.25-3.30 (m, 4 H). MS (ES+) 485.4 m/z (M+H)⁺

Example 19

N-Methyl-N-(3-(methylsulfonyl)benzyl)-7-(4-(2-(pyridin-2-yl)ethyl)piperazin-1-yl)benzofuran-2-carboxamide

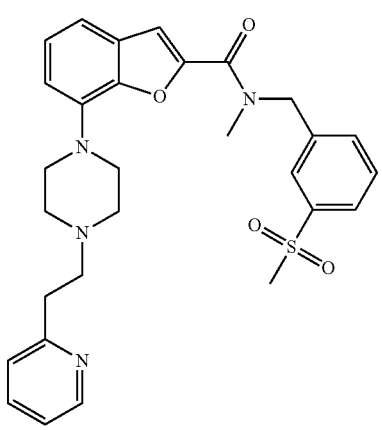 [SMILES: CN(Cc1cccc(S(C)(=O)=O)c1)C(=O)c1cc2cccc(N3CCN(CCc4ccccn4)CC3)c2o1]

Yield: 26%

¹H NMR (600 MHz, acetonitrile-d₃ 55° C.) δ ppm 8.49 (d, 1 H), 7.87-7.90 (m, 2 H), 7.71 (d, 1 H), 7.63-7.67 (m, 2 H), 7.36 (s, 1 H), 7.27 (d, 1 H), 7.22-7.25 (m, 1 H), 7.19 (t, 1 H), 7.15 (dd, 1 H), 6.87 (d, 1 H), 4.95 (br. s., 2 H), 3.21 (br. s., 7 H), 3.06 (s, 3 H), 2.91-2.96 (m, 2 H), 2.70-2.78 (m, 2 H), 2.53 (br. s., 4 H). MS (ES+) m/z 533.3 (M+H)⁺

Example 20

N-((6-Cyanopyridin-3-yl)methyl)-7-(4-(2-(pyridin-2-yl)ethyl)piperazin-1-yl)benzofuran-2-carboxamide

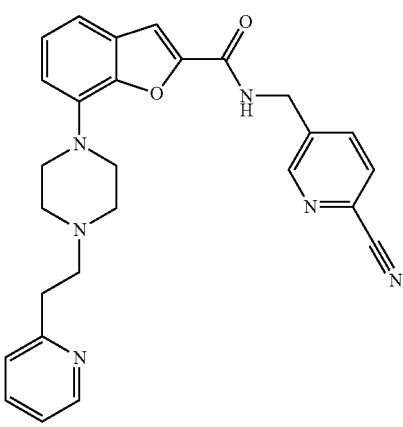 [SMILES: N#Cc1ccc(CNC(=O)c2cc3cccc(N4CCN(CCc5ccccn5)CC4)c3o2)cn1]

Yield: 40%

¹H NMR (500 MHz, acetonitrile-d₃) δ ppm 8.72 (d, 1 H), 8.48 (ddd, 1 H), 7.93 (dd, 1 H), 7.84 (t, 1 H), 7.78 (dd, 1 H), 7.65 (td, 1 H), 7.41 (s, 1 H), 7.24-7.29 (m, 2 H), 7.21 (t, 1 H), 7.16 (ddd, 1 H), 6.91 (dd, 1 H), 4.66 (d, 2 H), 3.30-3.34 (m, 4

H), 2.95-2.99 (m, 2 H), 2.77-2.81 (m, 2 H), 2.70-2.74 (m, 4 H). MS (ES+) m/z 467.3 (M+H)+

Example 21

N-Methyl-7-(4-(2-(pyridin-2-yl)ethyl)piperazin-1-yl)-N-(pyridin-3-ylmethyl)benzofuran-2-carboxamide

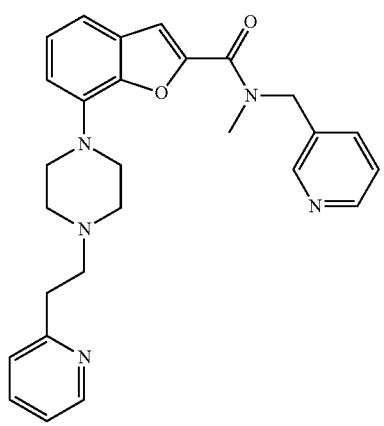 [SMILES: CN(Cc1cccnc1)C(=O)c1cc2cccc(N3CCN(CCc4ccccn4)CC3)c2o1]

Yield: 49%
$^{1}$H NMR (600 MHz, acetonitrile-$d_3$ 55° C.) δ ppm 8.59 (s, 1H), 8.53 (d, 1 H), 8.49 (d, 1 H), 7.74 (d, 1 H), 7.65 (td, 1 H), 7.33-7.37 (m, 2 H), 7.23-7.28 (m, 2 H), 7.19 (t, 1 H), 7.13-7.17 (m, 1 H), 6.87 (d, 1 H), 4.84 (br. s., 2H), 3.09-3.32 (m, 7 H), 2.95 (t, 2 H), 2.72-2.80 (m, 2 H), 2.56 (br. s., 4 H). MS (ES+) m/z 456.3 (M+H)+

Example 22

N-(3-Cyanobenzyl)-7-(4-(2-(pyridin-2-yl)ethyl)piperazin-1-yl)benzofuran-2-carboxamide

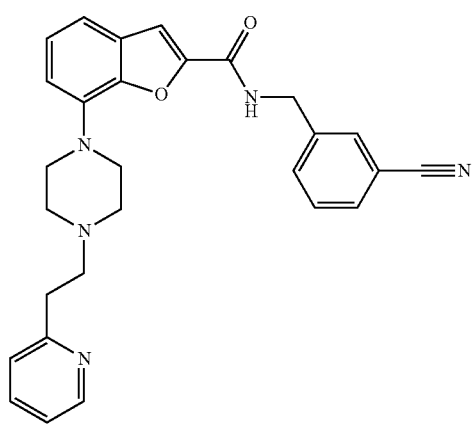 [SMILES: N#Cc1cccc(CNC(=O)c2cc3cccc(N4CCN(CCc5ccccn5)CC4)c3o2)c1]

Yield: 30%
$^{1}$H NMR (500 MHz, acetonitrile-$d_3$) δ ppm 8.47-8.49 (m, 1 H), 7.80 (t, 1 H), 7.72-7.74 (m, 1 H), 7.61-7.70 (m, 3 H), 7.51 (t, 1 H), 7.41 (s, 1 H), 7.24-7.29 (m, 2 H), 7.21 (t, 1 H), 7.15 (ddd, 1 H), 6.91 (dd, 1 H), 4.61 (d, 2 H), 3.30-3.34 (m, 4 H), 2.95-2.99 (m, 2 H), 2.79 (t, 2H), 2.70-2.74 (m, 4 H). MS (ES+) m/z 466.3 (M+H)+

Example 23

(7-(4-(2-(Pyridin-2-yl)ethyl)piperazin-1-yl)benzofuran-2-yl)(4-(thiazol-2-yl)piperazin-1-yl)methanone

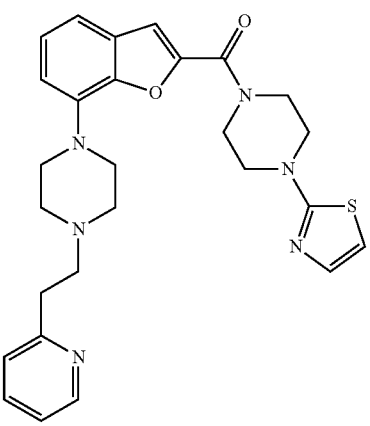 [SMILES: O=C(c1cc2cccc(N3CCN(CCc4ccccn4)CC3)c2o1)N1CCN(c2nccs2)CC1]

Yield: 42%
$^{1}$H NMR (500 MHz, acetonitrile-$d_3$) δ ppm 8.46-8.51 (m, 1H), 7.65 (td, 1H), 7.29 (s, 1H), 7.26-7.29 (m, 1 H), 7.24-7.26 (m, 1 H), 7.18-7.23 (m, 2 H), 7.15 (ddd, 1 H), 6.89 (dd, 1H), 6.73 (d, 1 H), 3.92 (br. s., 4 H), 3.56-3.60 (m, 4 H), 3.28-3.33 (m, 4 H), 2.95-3.00 (m, 2H), 2.78-2.82 (m, 2 H), 2.70-2.74 (m, 4 H). MS (ES+) m/z 503.3 (M+H)+

Example 24

N-(1-(3-Methoxypyridin-2-yl)piperidin-4-yl)-7-(4-(2-(pyridin-2-yl)ethyl)piperazin-1-yl)benzofuran-2-carboxamide

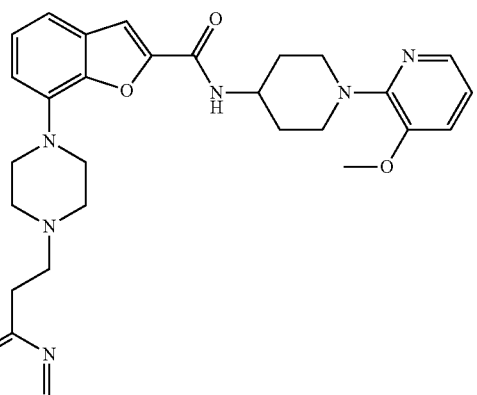

Yield: 20%
$^{1}$H NMR (500 MHz, acetonitrile-$d_3$) δ ppm 8.49 (ddd, 1H), 7.79 (dd, 1 H), 7.65 (td, 1 H), 7.36 (s, 1 H), 7.26-7.29 (m, 1 H), 7.23-7.26 (m, 1 H), 7.20 (t, 1 H), 7.14-7.18 (m, 2 H), 7.03 (d, 1 H), 6.90 (dd, 1 H), 6.85 (dd, 1 H), 4.04-4.13 (m, 1 H), 3.94-4.00 (m, 2 H), 3.83 (s, 3 H), 3.29-3.33 (m, 4 H), 2.95-

3.00 (m, 2 H), 2.86-2.93 (m, 2 H), 2.77-2.82 (m, 2 H), 2.71-2.74 (m, 4 H), 1.96-2.02 (m, 2 H), 1.74-1.83 (m, 2H). MS (ES+) m/z 541.4 (M+H)+

Example 25

N-Methyl-7-(4-(2-(pyridin-2-yl)ethyl)piperazin-1-yl)-N-(pyridin-2-ylmethyl)benzofuran-2-carboxamide

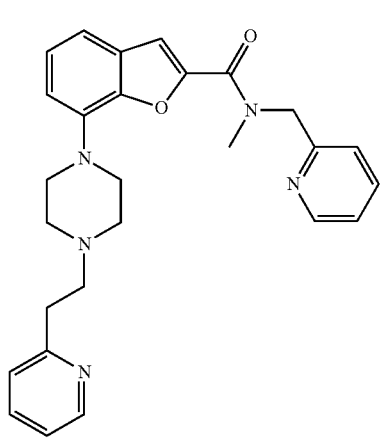 [SMILES: CN(Cc1ccccn1)C(=O)c1cc2cccc(N3CCN(CCc4ccccn4)CC3)c2o1]

Yield: 33%

$^{1}$H NMR (600 MHz, acetonitrile-$d_3$ 55° C.) δ ppm 8.57 (d, 1 H), 8.50 (d, 1 H), 7.73-7.79 (m, 1H), 7.65 (td, 1 H), 7.36 (d, 1 H), 7.33 (s, 1 H), 7.25-7.29 (m, 2 H), 7.14-7.24 (m, 3 H), 6.85 (d, 1 H), 4.94 (br. s., 2 H), 3.22 (br. s., 7 H), 2.95 (t, 2 H), 2.72-2.80 (m, 2 H), 2.56 (br. s., 4H). MS (ES+) m/z 456.3 (M+H)+

Example 26

N-(3-Methoxybenzyl)-7-(4-(2-(pyridin-2-yl)ethyl)piperazin-1-yl)benzofuran-2-carboxamide

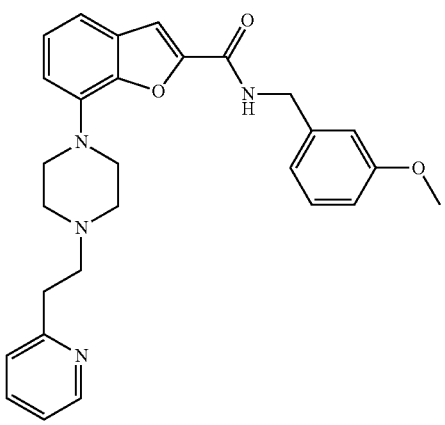 [SMILES: COc1cccc(CNC(=O)c2cc3cccc(N4CCN(CCc5ccccn5)CC4)c3o2)c1]

Yield: 38%

$^{1}$H NMR (500 MHz, acetonitrile-$d_3$) δ ppm 8.48 (ddd, 1H), 7.70 (t, 1 H), 7.65 (td, 1 H), 7.39 (s, 1 H), 7.24-7.29 (m, 3 H), 7.20 (t, 1 H), 7.15 (ddd, 1 H), 6.93-6.97 (m, 2 H), 6.90 (dd, 1H), 6.83 (dd, 1 H), 4.56 (d, 2 H), 3.77 (s, 3 H), 3.29-3.34 (m, 4 H), 2.95-2.99 (m, 2 H), 2.76-2.81 (m, 2 H), 2.70-2.74 (m, 4 H). MS (ES+) m/z 471.3 (M+H)+

Example 27

N-(1-(Pyridin-2-yl)cyclopropyl)-7-(4-(2-(pyridin-2-yl)ethyl)piperazin-1-yl)benzofuran-2-carboxamide

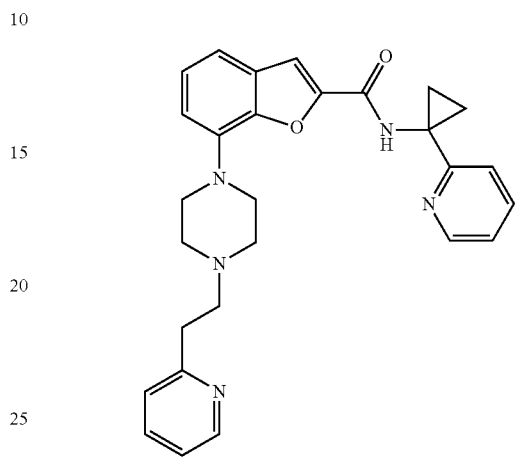

Yield: 59%

$^{1}$H NMR (500 MHz, acetonitrile-$d_3$) δ ppm 8.48 (ddd, 1 H), 8.45 (ddd, 1 H), 7.97 (br. s., 1 H), 7.61-7.67 (m, 2 H), 7.44 (dt, 1 H), 7.43 (s, 1 H), 7.26-7.29 (m, 2 H), 7.22 (t, 1 H), 7.15 (ddd, 1 H), 7.12 (ddd, 1 H), 6.92 (dd, 1 H), 3.32-3.36 (m, 4 H), 2.95-3.00 (m, 2 H), 2.77-2.81 (m, 2 H), 2.71-2.75 (m, 4 H), 1.63-1.66 (m, 2 H), 1.37-1.40 (m, 2 H). MS (ES+) m/z 468.3 (M+H)+

Example 28

N-(4-Methoxybenzyl)-7-(4-(2-(pyridin-2-yl)ethyl)piperazin-1-yl)benzofuran-2-carboxamide

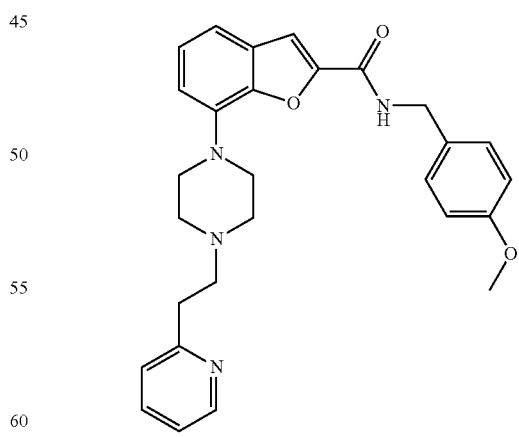

Yield: 47%

$^{1}$H NMR (500 MHz, acetonitrile-$d_3$) δ ppm 8.48 (ddd, 1 H), 7.63-7.69 (m, 2 H), 7.37 (s, 1 H), 7.29-7.32 (m, 2 H), 7.26-7.29 (m, 1 H), 7.23-7.26 (m, 1 H), 7.20 (t, 1 H), 7.15 (ddd, 1 H), 6.88-6.92 (m, 3 H), 4.51 (d, 2 H), 3.77 (s, 3 H), 3.29-3.33

(m, 4 H), 2.95-2.99 (m, 2 H), 2.77-2.81 (m, 2 H), 2.70-2.73 (m, 4 H). MS (ES+) m/z 471.3 (M+H)+

Example 29

N-(2-(4-Methylpyrimidin-2-yl)ethyl)-7-(4-(2-(pyridin-2-yl)ethyl)piperazin-1-yl)benzofuran-2-carboxamide

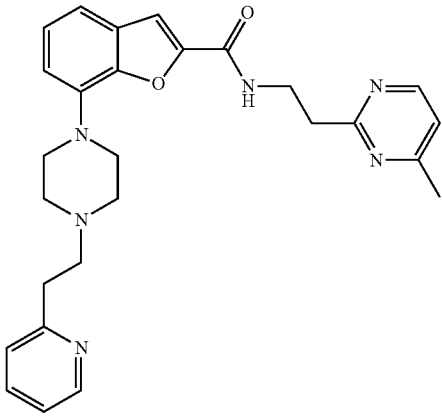 [SMILES: Cc1ccnc(CCNC(=O)c2cc3cccc(N4CCN(CCc5ccccn5)CC4)c3o2)n1]

Yield: 16%
$^1$H NMR (500 MHz, acetonitrile-d$_3$) δ ppm 8.54 (d, 1 H), 8.50 (ddd, 1 H), 7.66 (td, 1 H), 7.56 (t, 1 H), 7.33 (s, 1 H), 7.27-7.30 (m, 1 H), 7.22-7.25 (m, 1 H), 7.13-7.21 (m, 3 H), 6.89 (dd, 1 H), 3.83 (q, 2 H), 3.27-3.31 (m, 4 H), 3.15 (t, 2 H), 2.96-3.01 (m, 2 H), 2.79-2.83 (m, 2 H), 2.69-2.73 (m, 4 H), 2.46 (s, 3 H). MS (ES+) m/z 471.3 (M+H)+

Example 30

N-(2-(1-Methyl-1H-imidazol-4-yl)ethyl)-7-(4-(2-(pyridin-2-yl)ethyl)piperazin-1-yl)benzofuran-2-carboxamide

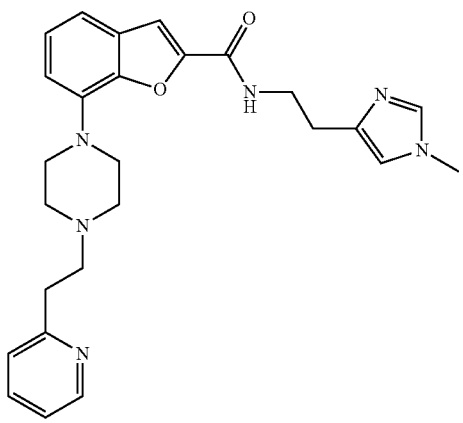 [SMILES: Cn1cnc(CCNC(=O)c2cc3cccc(N4CCN(CCc5ccccn5)CC4)c3o2)c1]

Yield: 29%
$^1$H NMR (500 MHz, acetonitrile-d$_3$) δ ppm 8.49 (ddd, 1 H), 8.09 (br. s., 1 H), 7.66 (td, 1 H), 7.40 (s, 1 H), 7.34 (s, 1 H), 7.28-7.31 (m, 1 H), 7.23-7.25 (m, 1 H), 7.20 (t, 1 H), 7.16 (ddd, 1 H), 6.90 (dd, 1 H), 6.81 (s, 1 H), 3.63 (s, 3 H), 3.60 (q, 2 H), 3.32-3.37 (m, 4 H), 2.97-3.02 (m, 2 H), 2.80-2.85 (m, 2 H), 2.73-2.79 (m, 6 H). MS (ES+) m/z 459.4 (M+H)+

Example 31

7-(4-(2-(Pyridin-2-yl)ethyl)piperazin-1-yl)-N-((tetrahydro-2H-pyran-4-yl)methyl)benzofuran-2-carboxamide

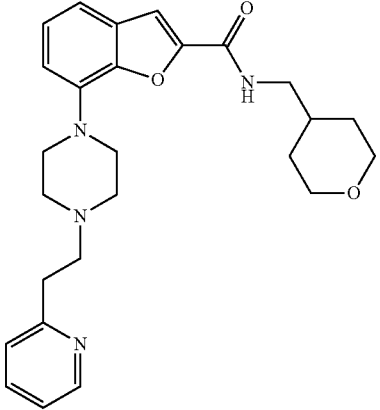 [SMILES: O=C(NCC1CCOCC1)c1cc2cccc(N3CCN(CCc4ccccn4)CC3)c2o1]

Yield: 51%
$^1$H NMR (500 MHz, acetonitrile-d$_3$) δ ppm 8.49 (ddd, 1 H), 7.66 (td, 1 H), 7.34 (s, 1 H), 7.28 (d, 2 H), 7.23-7.25 (m, 1 H), 7.19 (t, 1 H), 7.16 (ddd 1 H), 6.89 (dd, 1 H), 3.87-3.92 (m, 2 H), 3.30-3.36 (m, 6 H), 3.28 (t, 2 H), 2.96-3.00 (m, 2 H), 2.78-2.82 (m, 2 H), 2.72-2.75 (m, 4 H), 1.82-1.91 (m, 1 H), 1.61-1.67 (m, 2 H), 1.23-1.33 (m, 2 H). MS (ES+) m/z 449.4 (M+H)+

Example 32

N-(1-(1-Methyl-1H-pyrazol-5-yl)ethyl)-7-(4-(2-(pyridin-2-yl)ethyl)piperazin-1-yl)benzofuran-2-carboxamide

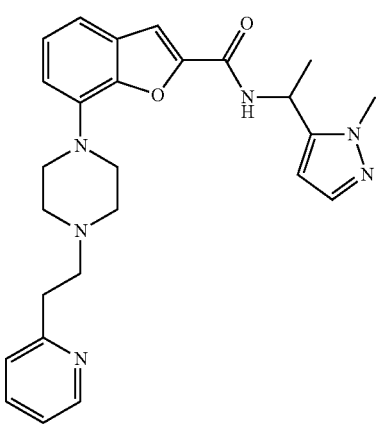 [SMILES: CC(NC(=O)c1cc2cccc(N3CCN(CCc4ccccn4)CC3)c2o1)c1ccnn1C]

Yield: 51%
$^1$H NMR (500 MHz, acetonitrile-d$_3$) δ ppm 8.48 (ddd, 1 H), 7.65 (td, 1 H), 7.39 (s, 1 H), 7.38 (br. s., 1 H), 7.33 (d, 1 H), 7.27 (d, 1 H), 7.23-7.26 (m, 1 H), 7.20 (t, 1 H), 7.16 (ddd, 1 H), 6.90 (dd, 1 H), 6.30-6.31 (m, 1 H), 5.40-5.47 (m, 1 H), 3.81 (s, 3 H), 3.27-3.32 (m, 4 H), 2.94-3.00 (m, 2 H), 2.76-2.81 (m, 2 H), 2.68-2.73 (m, 4 H), 1.61 (d, 3 H). MS (ES+) m/z 459.4 (M+H)+

Example 33

N-(1-(6-Methylpyridin-3-yl)ethyl)-7-(4-(2-(pyridin-2-yl)ethyl)piperazin-1-yl)benzofuran-2-carboxamide

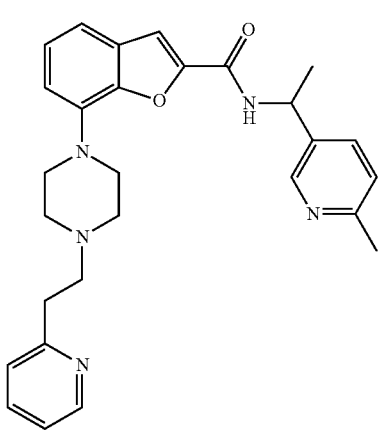 [SMILES: Cc1ccc(C(C)NC(=O)c2cc3cccc(N4CCN(CCc5ccccn5)CC4)c3o2)cn1]

Yield: 43%
1H NMR (500 MHz, acetonitrile-d3) δ ppm 8.51 (d, 1 H), 8.48 (ddd, 1 H), 7.63-7.69 (m, 2 H), 7.46 (d, 1 H), 7.37 (s, 1 H), 7.26-7.29 (m, 1 H), 7.23-7.26 (m, 1 H), 7.14-7.22 (m, 3 H), 6.90 (dd, 1 H), 5.22 (quin, 1 H), 3.29-3.34 (m, 4 H), 2.95-3.00 (m, 2 H), 2.77-2.82 (m, 2 H), 2.70-2.75 (m, 4 H), 2.47 (s, 3 H), 1.60 (d, 3 H). MS (ES+) m/z 470.4 (M+H)+

Example 34

N-((2-Methylpyrimidin-5-yl)methyl)-7-(4-(2-(pyridin-2-yl)ethyl)piperazin-1-yl)benzofuran-2-carboxamide

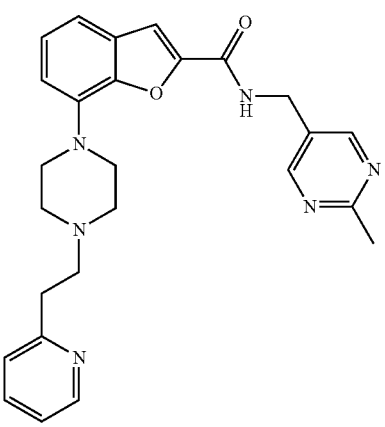 [SMILES: Cc1ncc(CNC(=O)c2cc3cccc(N4CCN(CCc5ccccn5)CC4)c3o2)cn1]

Yield: 21%
1H NMR (500 MHz, acetonitrile-d3) δ ppm 8.66 (s, 2 H), 8.48 (ddd, 1 H), 7.76 (t, 1 H), 7.65 (td, 1 H), 7.39 (s, 1 H), 7.26-7.29 (m, 1 H), 7.23-7.26 (m, 1 H), 7.20 (t, 1 H), 7.16 (ddd, 1 H), 6.90 (dd, 1 H), 4.53 (d, 2 H), 3.29-3.34 (m, 4 H), 2.95-3.00 (m, 2 H), 2.77-2.81 (m, 2 H), 2.70-2.74 (m, 4 H), 2.62 (s, 3 H). MS (ES+) m/z 457.3 (M+H)+

Example 35

7-(4-(2-(Pyridin-2-yl)ethyl)piperazin-1-yl)-N-(pyridin-3-ylmethyl)benzofuran-2-carboxamide

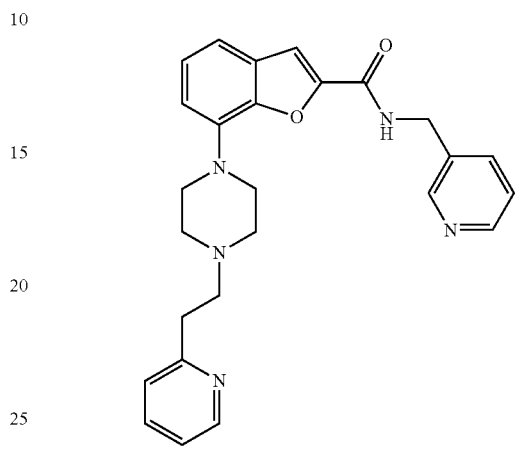

Yield: 46%
1H NMR (500 MHz, acetonitrile-d3) 8.56 (ddd, 1 H), 8.49 (ddd, 1 H), 8.02 (br. s., 1 H), 7.74 (td, 1 H), 7.65 (td, 1 H), 7.40 (s, 1 H), 7.36-7.39 (m, 1 H), 7.24-7.30 (m, 3 H), 7.21 (t, 1 H), 7.16 (ddd, 1 H), 6.91 (dd, 1 H), 4.69 (d, 2 H), 3.32-3.36 (m, 4 H), 2.96-3.01 (m, 2 H), 2.79-2.83 (m, 2 H), 2.73-2.77 (m, 4 H). MS (ES+) m/z 442.3 (M+H)+

Example 36

(7-(4-(2-(Pyridin-2-yl)ethyl)piperazin-1-yl)benzofuran-2-yl)(3-(pyridin-3-yloxy)azetidin-1-yl)methanone

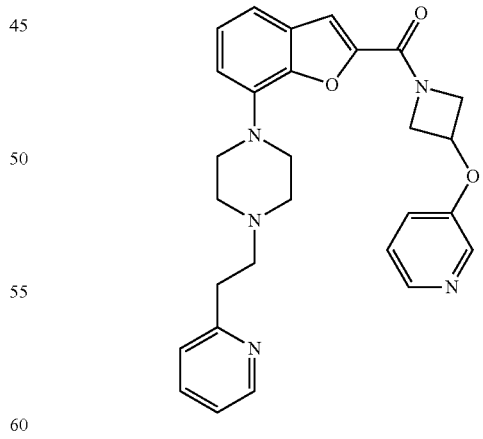

Yield: 36%
1H NMR (500 MHz, acetonitrile-d3) δ ppm 8.50 (ddd, 1 H), 8.26 (d, 1 H), 8.23 (dd, 1 H), 7.67 (td, 1 H), 7.38 (s, 1 H), 7.32-7.35 (m, 1 H), 7.28-7.30 (m, 1 H), 7.24-7.27 (m, 1 H), 7.18-7.24 (m, 2 H), 7.17 (ddd, 1 H), 6.88 (dd, 1 H), 5.16-5.21 (m, 1 H), 5.05-5.11 (m, 1 H), 4.54-4.64 (m, 2 H), 4.12-4.18

(m, 1 H), 3.20-3.31 (m, 4 H), 2.93-2.99 (m, 2 H), 2.74-2.79 (m, 2 H), 2.63 (d, 4 H). MS (ES+) m/z 484.3 (M+H)⁺

Example 37

N-(3-Hydroxybenzyl)-7-(4-(2-(pyridin-2-yl)ethyl)piperazin-1-yl)benzofuran-2-carboxamide

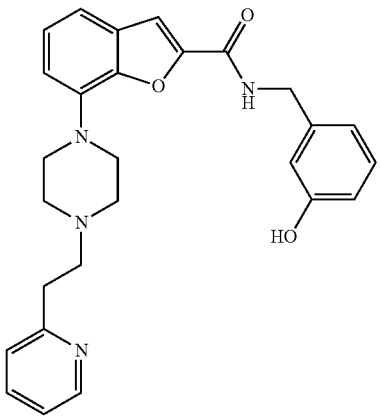 [SMILES: O=C(NCc1cccc(O)c1)c1cc2cccc(N3CCN(CCc4ccccn4)CC3)c2o1]

Yield: 10%
¹H NMR (500 MHz, acetonitrile-d₃) δ ppm 8.47-8.50 (m, 1 H), 7.63-7.70 (m, 2 H), 7.39 (s, 1 H), 7.24-7.29 (m, 2 H), 7.14-7.22 (m, 3 H), 6.90 (dd, 1 H), 6.85-6.87 (m, 1 H), 6.81-6.83 (m, 1 H), 6.70 (dd, 1 H), 4.52 (d, 2 H), 3.29-3.34 (m, 4 H), 2.95-3.00 (m, 2 H), 2.76-2.82 (m, 2 H), 2.70-2.74 (m, 4 H). OH not visible. MS (ES+) m/z 457.3 (M+H)⁺

Example 38

7-(4-(2-(1-Acetylindolin-5-yl)ethyl)piperazin-1-yl)-N,N-dimethylbenzofuran-2-carboxamide

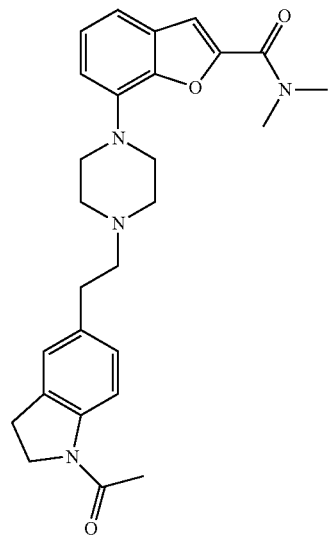 [SMILES: CC(=O)N1CCc2cc(CCN3CCN(c4cccc5cc(C(=O)N(C)C)oc45)CC3)ccc21]

The compound was prepared according to the procedure disclosed in Example 1 starting from lithium 7-(4-(2-(1-acetylindolin-5-yl)ethyl)piperazin-1-yl)benzofuran-2-carboxylate (80 mg, 0.21 mmol) and diamine hydrochloride (74 mg, 0.91 mmol). Yield: 52 mg (62%). ¹H NMR (500 MHz, acetonitrile-d₃) δ ppm 8.00 (d, 1 H), 7.23-7.25 (m, 2 H), 7.20 (t, 1 H), 7.11 (br. s., 1 H), 7.01-7.05 (m, 1 H), 6.86-6.89 (m, 1 H), 4.06 (t, 2 H), 3.23-3.36 (m, 7 H), 3.14 (t, 2 H), 3.07 (br. s., 3 H), 2.74-2.79 (m, 2 H), 2.67-2.72 (m, 4 H), 2.59-2.64 (m, 2 H), 2.13 (s, 3 H). MS (ES+) m/z 461.3 (M+H)⁺.

The lithium 7-(4-(2-(1-acetylindolin-5-yl)ethyl)piperazin-1-yl)benzofuran-2-carboxylate used as a starting material was prepared as follows:

Example 38a 1-(5-(2-Bromoethyl)indolin-1-yl)ethanone/1-(5-(2-Chloroethyl)indolin-1-yl)ethanone

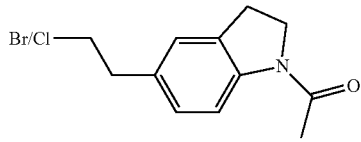

The compound mixture was synthesised from 1-acetylindoline (500 mg, 3.10 mmol) using the method from U.S. Pat. No. 5,705,515 to give the 1-actyl-5-(bromoacetyl)indoline which was further transformed to the product mixture by the method described in WO2005066165. Yield: 520 mg (in a ratio of ~4:1 Br:Cl).

Example 38b tert-Butyl 4-(2-(1-acetylindolin-5-yl)ethyl)piperazine-1-carboxylate

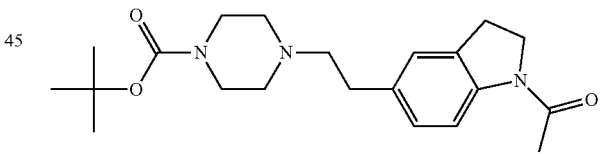

To a solution of piperazine-1-carboxylic acid tert-butyl ester (0.750 g, 4.03 mmol) in dry acetonitrile (20 mL) grounded potassium carbonate (0.486 mL, 8.05 mmol) was added followed by the product mixture from Example 38a (1.134 g) and the reaction was heated at 70° C. under argon over night. The acetonitrile was evaporated and DCM and water was added. The layers were separated and the aq phase was extracted with DCM (3×). The combined organic phases were dried (Na₂SO₄), filtered and evaporated. The crude mixture was purified by flash chromatography (heptane/EtOAc 75/25 to 0/100) to give 0.823 g (55%) of the title compound.

¹H NMR (400 MHz, acetonitrile-d₃) δ ppm 7.97 (d, 1 H), 7.07 (s, 1 H), 6.99 (d, 1 H), 4.04 (t, 2 H), 3.30-3.38 (m, 4 H), 3.12 (t, 2 H), 2.66-2.73 (m, 2 H), 2.48-2.55 (m, 2 H), 2.35-2.42 (m, 4 H), 2.12 (s, 3 H), 1.41 (s, 9 H). MS (ES+) m/z 374.3 (M+H)⁺.

Example 38c 1-(5-(2-(piperazin-1-yl)ethyl)indolin-1-yl)ethanone

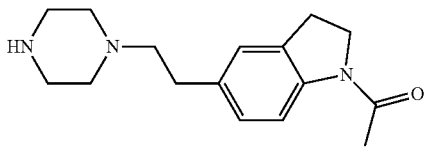 [SMILES: CC(=O)N1CCc2cc(CCN3CCNCC3)ccc21]

Trifluoroacetic acid (4.08 mL, 53.08 mmol) was added to a solution of tert-butyl 4-(2-(1-acetylindolin-5-yl)ethyl)piperazine-1-carboxylate (0.793 g, 2.12 mmol) in dry DCM and the reaction was stirred at room temperature for 60 min. The mixture was evaporated and the crude mixture was made basic with 10% NaOH aq. The aq phase was extracted with DCM (3×), dried ($Na_2SO_4$), filtered and evaporated to give 0.590 g of the product. This product was taken to the next step assuming quantitative yield without further purification. MS (ES+) m/z 274.2 (M+H)$^+$.

Example 38d

Ethyl 7-(4-(2-(1-acetylindolin-5-yl)ethyl)piperazin-1-yl)benzofuran-2-carboxylate

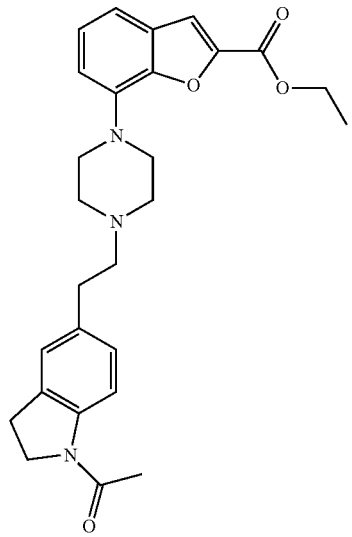 [SMILES: CCOC(=O)c1cc2cccc(N3CCN(CCc4ccc5c(c4)CCN5C(C)=O)CC3)c2o1]

Cesium carbonate (0.724 g, 2.22 mmol), 2-dicyclohexylphosphino-2',4',6'-triisopropylbiphenyl (0.081 g, 0.17 mmol) and tris(dibenzylideneacetone)dipalladium(0) (0.078 g, 0.09 mmol) were added under argon to a mixture of ethyl 7-bromobenzofuran-2-carboxylate (0.460 g, 1.71 mmol) and 1-(5-(2-(piperazin-1-yl)ethyl)indolin-1-yl)ethanone (0.491 g, 1.79 mmol) (example 38c) in dry degassed dioxane (8 mL) and the reaction was heated at 95° C. over night. After cooling to room temperature, water and DCM were added and the layers separated. The aq phase was extracted with DCM (3×). The combined organic phases were washed with water, dried ($MgSO_4$), filtered and evaporated. The crude product was purified by flash chromatography (DCM/MeOH 95/5) to give 0.485 g (61%) of the product.

$^1$H NMR (400 MHz, acetonitrile-$d_3$) δ ppm 7.99 (d, 1 H), 7.53 (s, 1 H), 7.27-7.30 (m, 1 H), 7.22 (t, 1 H), 7.11 (s, 1 H), 7.03 (d, 1 H), 6.93 (dd, 1 H), 4.37 (q, 2 H), 4.05 (t, 2 H), 3.28-3.36 (m, 4 H), 3.14 (t, 2 H), 2.74-2.80 (m, 2 H), 2.67-2.74 (m, 4 H), 2.59-2.65 (m, 2 H), 2.12 (s, 3 H), 1.37 (t, 3 H). MS (ES+) m/z 462.3 (M+H)$^+$.

Example 38e

Lithium 7-(4-(2-(1-acetylindolin-5-yl)ethyl)piperazin-1-yl)benzofuran-2-carboxylate

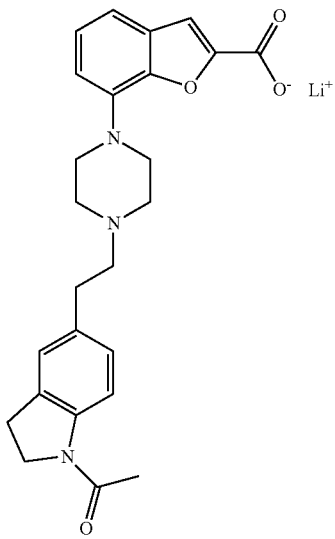 [SMILES: CC(=O)N1CCc2cc(CCN3CCN(c4cccc5cc(C(=O)[O-])oc45)CC3)ccc21 ; [Li+]]

Lithium hydroxide monohydrate (0.087 g, 2.08 mmol) was added to a solution of ethyl 7-(4-(2-(1-acetylindolin-5-yl)ethyl)piperazin-1-yl)benzofuran-2-carboxylate (0.481 g, 1.04 mmol) in tetrahydrofuran (9 mL) and water (1 mL) and the reaction was heated at 100° C. for 35 min in a microwave oven. The solvents were evaporated and the material was dried in vacuum over $P_2O_5$ to give 0.454 g of the crude product. The crude material was used in the next step assuming quantitative yield without further purification. MS (ES+) m/z 434.2 (M+H)$^+$.

Example 39

7-(4-(2-(4-Methoxypyridin-2-yl)ethyl)piperazin-1-yl)-N,N-dimethylbenzofuran-2-carboxamide

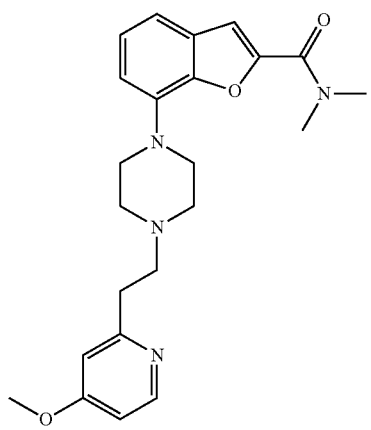

A solution of 4-methoxy-2-vinylpyridine (0.14 g, 1.04 mmol) in methanol (1 mL) was added to N,N-dimethyl-7-(piperazin-1-yl)benzofuran-2-carboxamide (0.095 g, 0.35 mmol) followed by acetic acid (0.020 mL, 0.35 mmol). The reaction was heated at 60° C. overnight. Dichloromethane and aqueous NaHCO₃ solution were added and the layers separated. The aqueous phase was extracted with dichloromethane (3×). The combined organic phases were washed with NaHCO₃ (aq) and water, dried (Na₂SO₄), filtered and evaporated. The crude product was purified by flash chromatography (SiO₂; DCM/MeOH 95/5). Yield: 0.94 g (66%).

¹H NMR (500 MHz, acetonitrile-d₃) δ ppm 8.29 (d, 1 H), 7.22-7.25 (m, 2 H), 7.19 (t, 1 H), 6.86 (dd, 1 H), 6.85 (d, 1 H), 6.73 (dd, 1 H), 3.82 (s, 3 H), 3.22-3.36 (m, 7 H), 3.06 (br. s., 3 H), 2.88-2.93 (m, 2 H), 2.75-2.79 (m, 2 H), 2.67-2.72 (m, 4 H). MS (ES+) m/z 409 (M+H)⁺.

The 4-methoxy-2-vinylpyridine used as a starting material was prepared as follows:

Example 39a

4-Methoxy-2-vinylpyridine

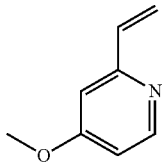

To degassed dioxane (12 mL) were added 2-chloro-4-methoxypyridine (0.12 mL, 1.05 mmol), vinylboronic acid MIDA ester (0.23 g, 1.26 mmol), 2-dicyclohexylphosphino-2',6'-dimethoxy-1,1'-biphenyl (0.043 g, 0.11 mmol) and palladium(II) acetate (0.012 g, 0.05 mmol) under argon and the reaction stirred for 15 min at rt then potassium phosphate (1.34 g, 6.31 mmol) dissolved in degassed water (2.5 mL) was added and the reaction heated at 90° C. overnight. 1M NaOH (aq) was added and the residue extracted with dichloromethane (3×). The combined organic phases were dried (MgSO₄), filtered and evaporated carefully to avoid losing the volatile product. The crude was taken to the next step without further purification. MS (ES+) m/z 136 (M+H)⁺.

The N,N-dimethyl-7-(piperazin-1-yl)benzofuran-2-carboxamide used as a starting material was prepared as follows:

Example 39b 7-(4-Benzyl-piperazin-1-yl)-benzofuran-2-carboxylic acid ethyl ester

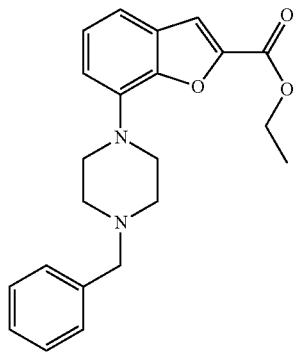 [SMILES: CCOC(=O)c1cc2cccc(N3CCN(Cc4ccccc4)CC3)c2o1]

The compound was prepared according to the procedure disclosed in Example 1a starting from benzylpiperazine (16.1 mL, 92.6 mmol) and 7-bromo-benzofuran-2-carboxylic acid ethyl ester (16.6 g, 61.7 mmol). The product was purified by flash chromatography (SiO₂; hexane/EtOAc, gradient 0-50%). Yield: 14 g (63%).

¹H NMR (400 MHz, chloroform-d) δ ppm 7.47 (s, 1 H), 7.16-7.39 (m, 7 H), 6.83-6.86 (m, 1 H), 4.40 (q, 2 H), 3.61 (s, 2 H), 3.38-3.42 (m, 4 H), 2.70-2.74 (m, 4 H), 1.40 (t, 3 H).

Example 39c 7-(4-Benzylpiperazin-1-yl)-N,N-dimethylbenzofuran-2-carboxamide

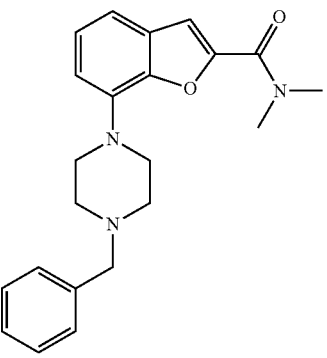 [SMILES: CN(C)C(=O)c1cc2cccc(N3CCN(Cc4ccccc4)CC3)c2o1]

7-(4-Benzyl-piperazin-1-yl)-benzofuran-2-carboxylic acid ethyl ester (1.0 g, 2.74 mmol) and DABAL-Me₃ (0.56 g, 2.20 mmol) were mixed in tetrahydrofuran (5 mL). Dimethylamine (2M in THF) (2.2 mL, 4.39 mmol) was added and the mixture was heated by microwave irradiation to 120° C. for 15 min. Brine was added and the mixture was extracted with dichloromethane, dried over Na₂SO₄, filtered and the solvent removed by rotary evaporation. The product was purified by flash chromatography (SiO₂; DCM/MeOH; gradient 0-2%) giving 7-(4-benzylpiperazin-1-yl)-N,N-dimethylbenzofuran-2-carboxamide (0.70 g, 1.93 mmol) in 70% yield.

¹H NMR (500 MHz, acetonitrile-d₃) δ ppm 7.32-7.39 (m, 4 H), 7.25-7.30 (m, 1 H), 7.22-7.25 (m, 2 H), 7.19 (t, 1 H), 6.86 (d, 1 H), 3.57 (s, 2 H), 3.22-3.36 (m, 7 H), 3.05 (br. s., 3 H), 2.60-2.66 (m, 4 H). MS (ES+) m/z 364 (M+H)⁺.

Example 39d

N,N-dimethyl-7-(piperazin-1-yl)benzofuran-2-carboxamide

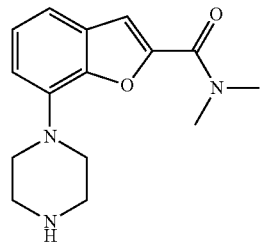 [SMILES: CN(C)C(=O)c1cc2cccc(N3CCNCC3)c2o1]

The reaction mixture of 7-(4-benzylpiperazin-1-yl)-N,N-dimethylbenzofuran-2-carboxamide (0.70 g, 1.93 mmol) and acetic acid (0.44 mL, 7.70 mmol) in methanol (30 mL) was debenzylated in a H-cube for 3 h at 50° C. using Catcart 30 Pd/C cartridge. Triethylamine (1.1 mL, 7.9 mmol) was added

Example 40

N,N-dimethyl-7-(4-(2-(5-methylpyridin-2-yl)ethyl)piperazin-1-yl)benzofuran-2-carboxamide

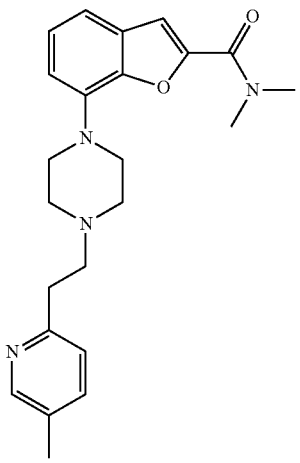 [SMILES: Cc1ccc(CCN2CCN(c3cccc4cc(C(=O)N(C)C)oc34)CC2)nc1]

The compound was prepared according to the procedure disclosed in Example 39 starting from of 5-methyl-2-vinylpyridine (0.11 g, 0.88 mmol) and N,N-dimethyl-7-(piperazin-1-yl)benzofuran-2-carboxamide (0.080 g, 0.29 mmol) (Example 39d). Yield: 0.030 g (26%).

$^1$H NMR (500 MHz, acetonitrile-$d_3$) δ ppm 8.23-8.25 (m, 1 H), 7.38 (dd, 1 H), 7.14-7.16 (m, 2 H), 7.10 (t, 1 H), 7.07 (d, 1 H), 6.78 (dd, 1 H), 3.17-3.26 (m, 7 H), 2.97 (br. s., 3 H), 2.81-2.86 (m, 2 H), 2.65-2.70 (m, 2 H), 2.58-2.64 (m, 4 H), 2.19 (s, 3 H). MS (ES+) m/z 393 (M+H)$^+$.

The 5-methyl-2-vinylpyridine used as a starting material was prepared as follows:

Example 40a

5-Methyl-2-vinylpyridine

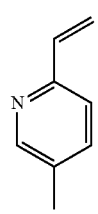

The compound was prepared according to the procedure disclosed in Example 39a starting from 2-chloro-5-methylpyridine (0.11 mL, 1.0 mmol). The crude was taken to the next step without further purification. Quantitative yield assumed. MS (ES+) m/z 120 (M+H)$^+$.

Example 41

7-(4-(2-(4-Cyanopyridin-2-yl)ethyl)piperazin-1-yl)-N,N-dimethylbenzofuran-2-carboxamide

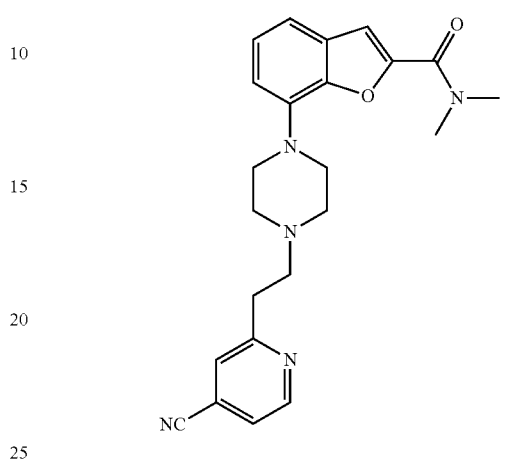

The compound was prepared according to the procedure disclosed in Example 39 starting from of 2-vinylisonicotinonitrile (0.076 g, 0.59 mmol), N,N-dimethyl-7-(piperazin-1-yl)benzofuran-2-carboxamide (0.080 g, 0.29 mmol) (Example 39d), and acetic acid (0.013 mL, 0.23 mmol). Ethanol was used as solvent and the reaction heated at 90° C. for two days. The crude product was purified by preparative HPLC to give the title compound. Yield: 0.061 g (52%).

$^1$H NMR (500 MHz, acetonitrile-$d_3$) δ ppm 8.69 (dd, 1 H), 7.61 (s, 1 H), 7.47 (dd, 1 H), 7.22-7.26 (m, 2 H), 7.19 (t, 1 H), 6.86 (dd, 1 H), 3.21-3.37 (m, 7 H), 2.99-3.13 (m, 5 H), 2.80 (t, 2 H), 2.65-2.72 (m, 4 H). MS (ES+) m/z 404 (M+H)$^+$.

The 2-vinylisonicotinonitrile used as a starting material was prepared as follows:

Example 41a

2-Vinylisonicotinonitrile

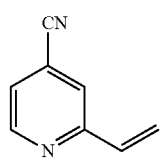

The compound was prepared according to the procedure disclosed in Example 39a starting from 2-bromoisonicotinonitrile (0.35 g, 1.91 mmol). The product was purified by flash chromatography (SiO$_2$; EtOAc). Yield: 0.26 g (quant.).

$^1$H NMR (500 MHz, chloroform-d) δ ppm 8.75 (dd, 1 H), 7.53-7.58 (m, 1 H), 7.39 (dd, 1 H), 6.83 (dd, 1 H), 6.33 (dd, 1 H), 5.65 (dd, 1 H). MS (ES+) m/z 131 (M+H)$^+$.

--- and the solvent was removed in vacuo. The crude material was purified by flash chromatography (SiO$_2$; DCM/MeOH; gradient 0-10%) to give 0.47 g (1.70 mmol) of product in 88% yield.

$^1$H NMR (400 MHz, acetonitrile-$d_3$) δ ppm 7.22-7.26 (m, 2 H), 7.19 (t, 1 H), 6.87 (dd, 1 H), 3.30 (br. s., 3 H), 3.19-3.25 (m, 4 H), 3.07 (br. s., 3 H), 2.95-3.01 (m, 4 H). MS (ES+) m/z 274 (M+H)$^+$.

Example 42

N,N-dimethyl-7-(4-(2-(6-(trifluoromethyl)pyridin-2-yl)ethyl)piperazin-1-yl)benzofuran-2-carboxamide

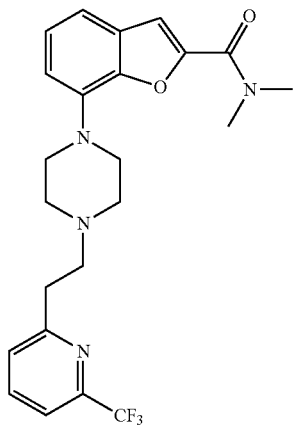 [SMILES: CN(C)C(=O)c1cc2cccc(N3CCN(CCc4cccc(C(F)(F)F)n4)CC3)c2o1]

N,N-dimethyl-7-(piperazin-1-yl)benzofuran-2-carboxamide (0.09 g, 0.33 mmol) (Example 39d) was dissolved in ethanol (0.95 mL), and acetic acid (0.015 mL, 0.26 mmol) was added, followed by 2-(trifluoromethyl)-6-vinylpyridine (0.10 g, 0.58 mmol) (volatile) dissolved in ethanol (1.40 mL). The mixture was heated at 73° C. for 14 h in the microwave and then heated for another 48 h at 86° C. in an oilbath, and finally it was heated in the microwave for 15 min at 100° C. More 2-(trifluoromethyl)-6-vinylpyridine (0.10 g, 0.58 mmol) and ethanol (0.95 mL) were added and the mixture was heated in a oil bath for 7 days at 86° C. The product was purified by flash chromatography (SiO$_2$; DCM/MeOH; gradient 0-7%) and then by preparative HPLC to give the title compound. Yield: 0.075 g (51%).

$^1$H NMR (500 MHz, acetonitrile-d$_3$) δ ppm 7.90 (t, 1 H), 7.61 (d, 1 H), 7.56 (d, 1 H), 7.22-7.26 (m, 2 H), 7.16-7.21 (m, 1 H), 6.86 (d, 1 H), 3.25-3.34 (m, 7 H), 3.06 (t, 5 H), 2.78-2.84 (m, 2 H), 2.68-2.73 (m, 4 H). MS (ES+) m/z 447 (M+H)$^+$.

The 2-(trifluoromethyl)-6-vinylpyridine used as a starting material was prepared as follows:

Example 42a 2-(Trifluoromethyl)-6-vinylpyridine

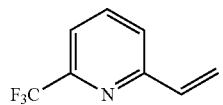

The compound was prepared according to the procedure disclosed in Example 39a starting from 2-bromo-6-(trifluoromethyl)pyridine (0.60 g, 2.65 mmol). The product was purified by flash chromatography (SiO$_2$; heptane:ethylacetate, gradient 0-4%). Yield: 0.12 g (26%).

MS (ES+) m/z 174 (M+H)$^+$.

Example 43

7-(4-(2-(5-Acetylpyridin-2-yl)ethyl)piperazin-1-yl)-N,N-dimethylbenzofuran-2-carboxamide

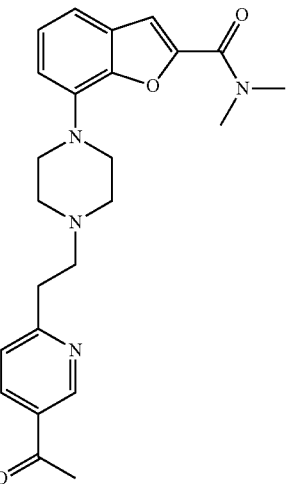

A reaction mixture of N,N-dimethyl-7-(piperazin-1-yl)benzofuran-2-carboxamide (0.078 g, 0.29 mmol) (Example 39d), 1-(6-vinylpyridin-3-yl)ethanone (0.15 g, 1.00 mmol) and acetic acid (0.016 mL, 0.29 mmol) in n-propanol (1.5 mL) and water (0.10 mL) was heated at 69° C. for 2 days. The product was purified by preparative HPLC to give the title compound.

Yield: 0.046 g (38%). $^1$H NMR (500 MHz, acetonitrile-d$_3$) δ ppm 9.05 (d, 1 H), 8.16 (dd, 1 H), 7.41 (d, 1 H), 7.22-7.26 (m, 2 H), 7.16-7.22 (m, 1 H), 6.83-6.89 (m, 1 H), 3.25-3.33 (m, 7 H), 3.05 (t, 5 H), 2.79-2.85 (m, 2 H), 2.68-2.73 (m, 4 H), 2.58 (s, 3 H). MS (ES+) m/z 421 (M+H)$^+$.

The 1-(6-vinylpyridin-3-yl)ethanone used as a starting material was prepared as follows:

Example 43a 1-(6-Vinylpyridin-3-yl)ethanone

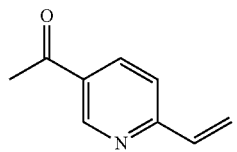

The reaction mixture of 1-(6-bromopyridin-3-yl)ethanone (0.68 g, 3.41 mmol), 2,4,6-trivinyl-1,3,5,2,4,6-trioxatriborinane:pyridine (1:1) (0.57 g, 2.39 mmol), potassium carbonate (0.85 g, 6.14 mmol), and Pd(Ph$_3$P)$_4$ (0.16 g, 0.14 mmol) in acetonitrile (10 mL) was degassed with argon for 5 minutes. Then it was heated in the microwave for 30 min at 115° C. The organic phase was removed using a pipette, dried (MgSO$_4$), filtered and concentrated and purified by flash chromatography (SiO$_2$; heptane/EtOAc, gradient 20-80%). Yield: 0.36 g (72%).

¹H NMR (500 MHz, chloroform-d) δ ppm 9.12 (d, 1 H), 8.20 (dd, 1 H), 7.44 (d, 1 H), 6.88 (dd, 1 H), 6.37 (d, 1 H), 5.65 (d, 1 H), 2.64 (s, 3 H). MS (ES+) m/z 148 (M+H)⁺.

Example 44

7-(4-(2-(5-Acetamidopyridin-2-yl)ethyl)piperazin-1-yl)-N,N-dimethylbenzofuran-2-carboxamide

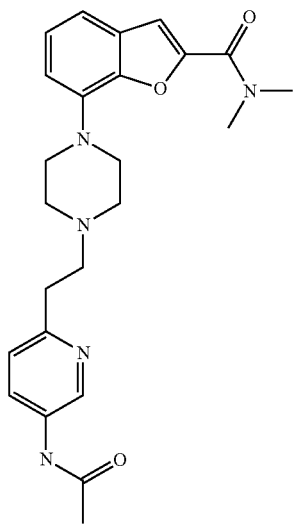 [SMILES: CC(=O)Nc1ccc(CCN2CCN(c3cccc4cc(C(=O)N(C)C)oc34)CC2)nc1]

The compound was prepared according to the procedure disclosed in Example 43 starting from N,N-dimethyl-7-(piperazin-1-yl)benzofuran-2-carboxamide (0.075 g, 0.27 mmol) (Example 39d) and N-(6-vinylpyridin-3-yl)acetamide (0.16 g, 0.96 mmol). The product was purified by preparative HPLC to give the title compound. Yield: 0.055 g (46%).

¹H NMR (500 MHz, acetonitrile-d₃) δ ppm 8.56 (d, 1 H), 8.33 (br. s., 1 H), 7.91 (dd, 1 H), 7.16-7.26 (m, 4 H), 6.84-6.89 (m, 1 H), 3.25-3.33 (m, 5 H), 3.06 (br. s., 2 H), 2.90-2.95 (m, 2 H), 2.72-2.78 (m, 2 H), 2.66-2.71 (m, 4 H), 2.14 (s, 3 H), 2.05-2.07 (m, 3 H). MS (ES+) m/z 436 (M+H)⁺.

The N-(6-vinylpyridin-3-yl)acetamide used as a starting material was prepared as follows:

Example 44a

N-(6-Vinylpyridin-3-yl)acetamide

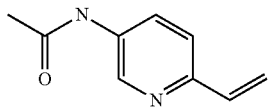

The compound was prepared according to the procedure disclosed in Example 43a starting from N-(6-bromopyridin-3-yl)acetamide (0.71 g, 3.28 mmol). The product was purified by flash chromatography (SiO₂; heptane/EtOAc; gradient 20-90%). Yield: 0.24 g (45%).

¹H NMR (500 MHz, chloroform-d) δ ppm 8.60 (d, 1 H), 8.44 (br. s., 1 H), 8.01 (dd, 1 H), 7.35 (d, 1 H), 6.77 (dd, 1 H), 6.10 (dd, 1 H), 5.36 (dd, 1 H), 2.08 (s, 3 H). MS (ES+) m/z 163 (M+H)⁺.

Example 45

Azetidin-1-yl(7-(4-(2-(6-methoxypyridin-2-yl)ethyl)piperazin-1-yl)benzofuran-2-yl)methanone

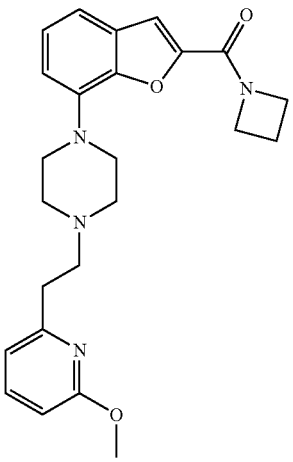 [SMILES: COc1cccc(CCN2CCN(c3cccc4cc(C(=O)N5CCC5)oc34)CC2)n1]

Azetidin-1-yl(7-(piperazin-1-yl)benzofuran-2-yl)methanone (0.070 g, 0.25 mmol) was dissolved in methanol (1 mL). 2-Methoxy-6-vinylpyridine (0.066 g, 0.49 mmol) and acetic acid (0.014 mL, 0.25 mmol) were added. The mixture was heated by microwave irradiation to 120° C. for 10 h. The product was purified by preparative HPLC to give the title compound.

Yield: 0.044 g (43%).

¹H NMR (500 MHz, acetonitrile-d₃) δ ppm 7.51-7.57 (m, 1 H), 7.30 (s, 1 H), 7.22-7.25 (m, 1 H), 7.19 (t, 1 H), 6.86 (dd, 1 H), 6.84 (d, 1 H), 6.58 (d, 1 H), 4.62 (t, 2 H), 4.11 (t, 2 H), 3.88 (s, 3 H), 3.23-3.31 (m, 4 H), 2.85-2.90 (m, 2 H), 2.76-2.82 (m, 2 H), 2.66-2.72 (m, 4 H), 2.38 (t, 2 H). MS (ES+) m/z 221 (M+H)⁺.

The 2-methoxy-6-vinylpyridine used as a starting material was prepared as follows:

Example 45a

2-Methoxy-6-vinylpyridine

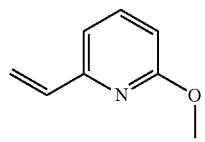

The compound was prepared according to the procedure disclosed in Example 39a starting from 2-chloro-6-methoxypyridine (0.41 mL, 3.48 mmol). The product was purified by flash chromatography (SiO₂; DCM/MeOH; gradient 0-1%). Yield 0.37 g (79%).

¹H NMR (500 MHz, chloroform-d) δ ppm 7.48-7.57 (m, 1 H), 6.83 (d, 1 H), 6.72 (dd, 1 H), 6.63 (d, 1 H), 6.30 (dd, 1 H), 5.42 (dd, 1 H), 3.97 (s, 3 H). MS (ES+) m/z 136 (M+H)⁺.

The azetidin-1-yl(7-(piperazin-1-yl)benzofuran-2-yl)methanone used as a starting material was prepared as follows:

Example 45b

Azetidin-1-yl(7-(4-benzylpiperazin-1-yl)benzofuran-2-yl)methanone

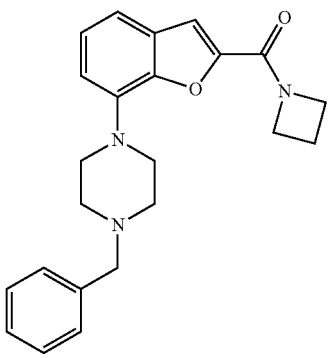 [SMILES: O=C(c1cc2cccc(N3CCN(Cc4ccccc4)CC3)c2o1)N1CCC1]

The compound was prepared according to the procedure disclosed in Example 39c starting from ethyl 7-(4-benzylpiperazin-1-yl)benzofuran-2-carboxylate (1.0 g, 2.74 mmol) (Example 39b) and azetidine (0.20 mL, 3.02 mmol). Yield: 0.52 g (51%).

$^1$H NMR (500 MHz, chloroform-d) δ ppm 7.33-7.45 (m, 5 H), 7.28-7.33 (m, 1 H), 7.24-7.27 (m, 1 H), 7.19 (t, 1 H), 6.84 (d, 1 H), 4.67 (t, 2 H), 4.26 (t, 2 H), 3.62 (br. s., 2 H), 3.37 (br. s., 4 H), 2.70 (br. s., 4 H), 2.45 (quin, 2 H). MS (ES+) m/z 376 (M+H)$^+$.

Example 45c

Azetidin-1-yl(7-(piperazin-1-yl)benzofuran-2-yl)methanone

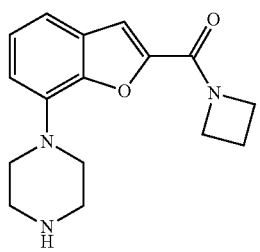 [SMILES: O=C(c1cc2cccc(N3CCNCC3)c2o1)N1CCC1]

The compound was prepared according to the procedure disclosed in Example 39d starting from azetidin-1-yl(7-(4-benzylpiperazin-1-yl)benzofuran-2-yl)methanone (0.52 g, 1.38 mmol) and acetic acid (0.63 mL, 11.1 mmol). A solution of ammonia (3 mL, 7N in MeOH) was added to the mixture after the reaction was complete. The solvent was removed by rotary evaporation. The crude product was purified by flash chromatography (SiO$_2$; gradient 0-10% ammonia (7N in MeOH) in DCM). Yield: 0.36 g (91%).

$^1$H NMR (500 MHz, methyl alcohol-d$_4$) δ ppm 7.43 (s, 1 H), 7.31 (d, 1 H), 7.23 (t, 1 H), 6.95 (d, 1 H), 4.74 (t, 2 H), 4.24 (t, 2 H), 3.32-3.35 (m, 4 H), 3.10-3.14 (m, 4 H), 2.48 (dt, 2 H). MS (ES+) m/z 286 (M+H)$^+$.

Example 46

7-(4-(2-(6-Methoxypyridin-2-yl)ethyl)piperazin-1-yl)-N,N-dimethylbenzofuran-2-carboxamide

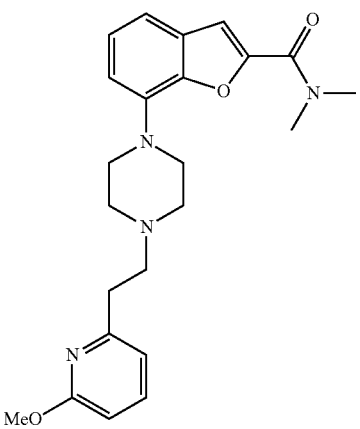 [SMILES: COc1cccc(CCN2CCN(c3cccc4cc(C(=O)N(C)C)oc34)CC2)n1]

A reaction mixture of N,N-dimethyl-7-(piperazin-1-yl)benzofuran-2-carboxamide (0.090 g, 0.33 mmol) (Example 39d), 2-(6-methoxypyridin-2-yl)ethyl 4-methylbenzenesulfonate (0.10 g, 0.33 mmol) and potassium carbonate (0.046 g, 0.33 mmol) in dry acetonitrile (10 mL) was heated at 80° C. for over night. After cooling, the mixture was filtered and the solvent removed in vacuo. The product was purified by preparative HPLC to give the title compound. Yield: 0.048 g (36%).

$^1$H NMR (500 MHz, acetonitrile-d$_3$) δ ppm 7.55 (dd, 1 H), 7.22-7.26 (m, 2 H), 7.19 (t, 1 H), 6.87 (dd, 1 H), 6.84 (d, 1 H), 6.58 (d, 1 H), 3.88 (s, 3 H), 3.23-3.36 (m, 7 H), 3.06 (br. s., 3 H), 2.85-2.91 (m, 2 H), 2.77-2.82 (m, 2 H), 2.67-2.73 (m, 4 H). MS (ES+) m/z 409 (M+H)$^+$.

The 2-(6-methoxypyridin-2-yl)ethyl 4-methylbenzenesulfonate used as a starting material was prepared as follows:

Example 46a

Diethyl 2-(6-methoxypyridin-2-yl)malonate

A slurry of 2-bromo-6-methoxypyridine (1.8 g, 9.57 mmol), copper(I) iodide (0.16 g, 0.86 mmol), 2-picolinic acid (0.21 g, 1.72 mmol), cesium carbonate (4.7 g, 14.4 mmol) and diethyl malonate (4.4 mL, 28.7 mmol) in dioxane (15 mL) was heated at 95° C. for 4 days. After cooling to room temperature, ethyl acetate and saturated aqueous NH$_4$Cl were added. The organic phase was separated and the aqueous phase extracted with ethyl acetate. The combined organic phases were dried over Na$_2$SO$_4$ and concentrated. The product was purified twice by flash chromatography (SiO$_2$; heptane/ethyl acetate, gradient 0-80% and second chromatography using heptane/ethyl acetate gradient 0-20%) giving the product. Yield: 1.1 g (43%).

$^1$H NMR (400 MHz, chloroform-d) δ ppm 7.60 (dd, 1 H), 7.01 (d, 1 H), 6.68-6.73 (m, 1 H), 4.86 (s, 1 H), 4.22-4.31 (m, 4 H), 3.91 (s, 3 H), 1.29 (t, 6 H). MS (ES+) m/z 268 (M+H)$^+$.

Example 46b

Ethyl 2-(6-methoxypyridin-2-yl)acetate

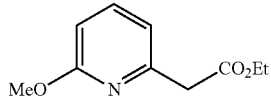 [SMILES: CCOC(=O)Cc1cccc(OC)n1]

A solution of diethyl 2-(6-methoxypyridin-2-yl)malonate (1.0 g, 3.74 mmol) and hydrochloric acid (1 M) (20 mL, 20.0 mmol) in ethanol (10 mL) was heated at 65° C. overnight. The solvent was removed under reduced pressure. The residue was dissolved in ethanol (15 mL) and hydrochloric acid (conc.) (0.5 mL, 6.00 mmol) was added. The reaction mixture was heated at 65° C. for 4 h. The solvent was removed under reduced pressure. Ethyl acetate and saturated NaHCO$_3$ aqueous solution were added. The organic layer was separated and the aqueous layer was extracted with ethyl acetate. The combined organic layers were dried (Na$_2$SO$_4$) and concentrated to give the product. Yield: 0.69 g (94%).

$^1$H NMR (500 MHz, chloroform-d) δ ppm 7.54 (t, 1 H), 6.85 (d, 1 H), 6.64 (d, 1 H), 4.20 (q, 2 H), 3.92 (s, 3 H), 3.75 (s, 2 H), 1.28 (t, 3 H). MS (ES+) m/z 196 (M+H)$^+$.

Example 46c 2-(6-Methoxypyridin-2-yl)ethanol

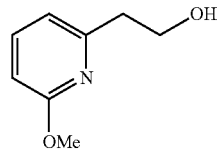 [SMILES: COc1cccc(CCO)n1]

Sodium borohydride (1.3 g, 34.8 mmol) was added to a solution of ethyl 2-(6-methoxypyridin-2-yl)acetate (0.68 g, 3.48 mmol) in ethanol (20 mL). The resulting solution was stirred at room temperature over night. The solvent was removed in vacuo. Ethyl acetate and saturated NaHCO$_3$ solution were added. The organic layer was separated and the aqueous layer was extracted with ethyl acetate. The combined organic layers were dried (Na$_2$SO$_4$) and concentrated to give the product. Yield: 0.23 g (44%).

$^1$H NMR (400 MHz, chloroform-d) δ ppm 7.53-7.60 (m, 1 H), 6.76 (d, 1 H), 6.66 (d, 1 H), 3.98-4.04 (m, 2 H), 3.94 (s, 3 H), 2.99 (t, 2 H). MS (ES+) m/z 154 (M+H)$^+$.

Example 46d 2-(6-Methoxypyridin-2-yl)ethyl 4-methylbenzenesulfonate

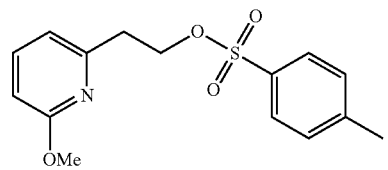 [SMILES: COc1cccc(CCOS(=O)(=O)c2ccc(C)cc2)n1]

A solution of 2-(6-methoxypyridin-2-yl)ethanol (0.23 g, 1.50 mmol), 4-dimethylaminopyridine (0.028 g, 0.23 mmol), triethylamine (0.63 mL, 4.50 mmol) and p-toluenesulfonyl chloride (0.34 g, 1.80 mmol) in dry dichloromethane (5 mL) was stirred at rt over night. The solvent was removed in vacuo. Ethyl acetate and water were added. The organic phase was separated and the aqueous phase was extracted with ethyl acetate. The combined organic phases were dried (Na$_2$SO$_4$) and concentrated. The product was purified by flash chromatography (SiO$_2$; heptane/EtOAc, gradient 0-100%). Yield: 0.18 g (38%).

$^1$H NMR (400 MHz, chloroform-d) δ ppm 7.63-7.69 (m, 2 H), 7.55 (t, 1 H), 7.23-7.31 (m, 2 H), 6.78 (d, 1 H), 6.63 (d, 1 H), 4.46 (t, 2 H), 3.81 (s, 3 H), 3.09 (t, 2 H), 2.44 (s, 3 H). MS (ES+) m/z 308 (M+H)$^+$.

Example 47

7-(4-(2-(5-Fluoropyridin-2-yl)ethyl)piperazin-1-yl)-N,N-dimethylbenzofuran-2-carboxamide

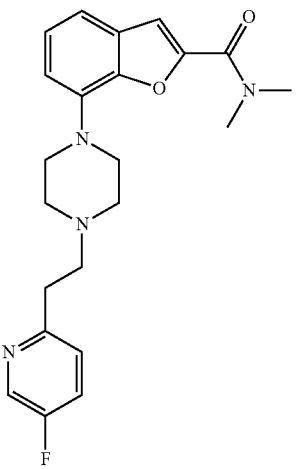 [SMILES: CN(C)C(=O)c1cc2cccc(N3CCN(CCc4ccc(F)cn4)CC3)c2o1]

The compound was prepared according to the procedure disclosed in Example 46 starting from N,N-dimethyl-7-(piperazin-1-yl)benzofuran-2-carboxamide (0.085 g, 0.31 mmol) (Example 39d) and 2-(5-fluoropyridin-2-yl)ethyl 4-methylbenzenesulfonate (0.092 g, 0.31 mmol). The product was purified by preparative HPLC to give the title compound. Yield: 0.049 g (39%).

¹H NMR (500 MHz, acetonitrile-d₃) δ ppm 8.38 (d, 1 H), 7.44 (td, 1 H), 7.32 (dd, 1 H), 7.22-7.26 (m, 2 H), 7.16-7.21 (m, 1 H), 6.86 (dd, 1 H), 3.24-3.35 (m, 7 H), 3.06 (br. s., 3 H), 2.76 (t, 2 H), 2.97 (t, 2 H), 2.67-2.72 (m, 4 H). MS (ES+) m/z 397 (M+H)⁺.

The 2-(5-fluoropyridin-2-yl)ethyl 4-methylbenzenesulfonate used as a starting material was prepared as follows:

Example 47a

Diethyl 2-(5-fluoropyridin-2-yl)malonate

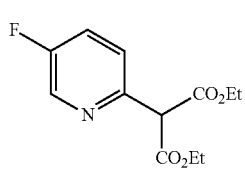

The compound was prepared according to the procedure disclosed in Example 46a starting from 2-bromo-5-fluoropyridine (0.54 g, 3.07 mmol). The reaction time was 3 days and the product purified by flash chromatography (SiO₂; heptane/EtOAc, gradient 0-20%) which gave the product. Yield: 0.43 g (55%).

¹H NMR (400 MHz, chloroform-d) δ ppm 8.43 (d, 1 H), 7.58 (dd, 1 H), 7.49 (dd, 1 H), 5.00 (s, 1 H), 4.20-4.31 (m, 4 H), 1.29 (t, 6 H). MS (ES+) m/z 256 (M+H)⁺.

Example 47b

Ethyl 2-(5-fluoropyridin-2-yl)acetate

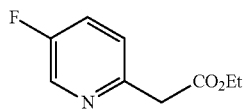

The compound was prepared according to the procedure disclosed in Example 46b starting from of diethyl 2-(5-fluoropyridin-2-yl)malonate (0.42 g, 1.65 mmol). Yield: 0.26 g (87%).

¹H NMR (400 MHz, chloroform-d) δ ppm 8.43 (d, 1 H), 7.39-7.47 (m, 1 H), 7.32-7.38 (m, 1 H), 4.20 (q, 2 H), 3.87 (s, 2 H), 1.28 (t, 3 H). MS (ES+) m/z 184 (M+H)⁺.

Example 47c 2-(5-Fluoropyridin-2-yl)ethanol

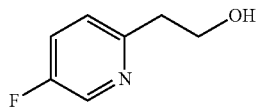

The compound was prepared according to the procedure disclosed in Example 46c starting from ethyl 2-(5-fluoropyridin-2-yl)acetate (0.26 g, 1.42 mmol). Yield: 0.17 g (82%).

¹H NMR (400 MHz, chloroform-d) δ ppm 8.39 (d, 1 H), 7.42 (td, 1 H), 7.22 (dd, 1 H), 4.03 (t, 2 H), 3.06 (t, 2 H). MS (ES+) m/z 142 (M+H)⁺.

Example 47d 2-(5-Fluoropyridin-2-yl)ethyl 4-methylbenzenesulfonate

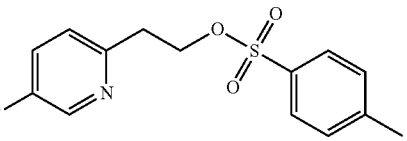

The compound was prepared according to the procedure disclosed in Example 46d starting from 2-(5-fluoropyridin-2-yl)ethanol (0.16 g, 1.13 mmol). The product was purified by flash chromatography (SiO₂; heptane/ethyl acetate, gradient 0-100%). Yield: 0.23 g (70%).

¹H NMR (400 MHz, chloroform-d) δ ppm 8.27 (d, 1 H), 7.65-7.71 (m, 2 H), 7.28-7.38 (m, 3 H), 7.18 (dd, 1 H), 4.42 (t, 2 H), 3.13 (t, 2 H), 2.45 (s, 3 H). MS (ES+) m/z 296 (M+H)⁺.

Example 48

7-(4-(2-(3-Methoxy-2-pyridyl)ethyl)piperazin-1-yl)-N,N-dimethylbenzofuran-2-carboxamide

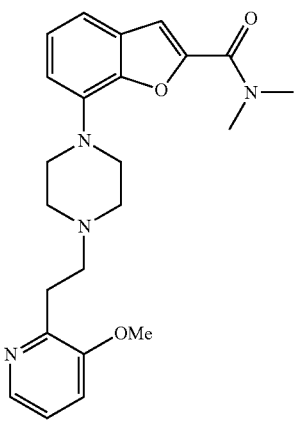 [SMILES: COc1cccnc1CCN1CCN(c2cccc3cc(C(=O)N(C)C)oc23)CC1]

The compound was prepared according to the procedure disclosed in Example 46 starting from N,N-dimethyl-7-(piperazin-1-yl)benzofuran-2-carboxamide (0.085 g, 0.31 mmol) (Example 39d) and 2-(3-methoxypyridin-2-yl)ethyl 4-methylbenzenesulfonate (0.092 g, 0.31 mmol). The product was purified by preparative HPLC to give the title compound.

Yield: 0.049 g (39%).

¹H NMR (500 MHz, acetonitrile-d₃) δ ppm 8.05 (dd, 1 H), 7.22-7.27 (m, 3 H), 7.14-7.21 (m, 2 H), 6.86 (dd, 1 H), 3.83 (s, 3 H), 3.21-3.37 (m, 7 H), 3.06 (br. s., 3 H), 2.93-3.02 (m, 2 H), 2.65-2.78 (m, 6 H). MS (ES+) m/z 397 (M+H)⁺.

The 2-(3-methoxypyridin-2-yl)ethyl 4-methylbenzenesulfonate used as a starting material was prepared as follows:

Example 48a

Diethyl 2-(3-Methoxypyridin-2-yl)malonate

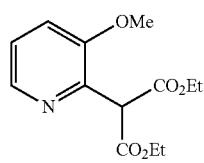 [SMILES: CCOC(=O)C(C(=O)OCC)c1ncccc1OC]

The compound was prepared according to the procedure disclosed in Example 46a starting from 2-bromo-3-methoxypyridine (1.06 g, 5.64 mmol). The reaction time was 3 days and the product purified by flash chromatography ($SiO_2$; heptane/EtOAc, gradient 0-20%) which gave the product. Yield: 1.0 g (68%).

$^1$H NMR (400 MHz, chloroform-d) δ ppm 8.18 (dd, 1 H), 7.20-7.25 (m, 1 H), 7.15-7.19 (m, 1 H), 5.11 (s, 1 H), 4.27 (q, 4 H), 3.83 (s, 3 H), 1.27 (t, 6 H). MS (ES+) m/z 268 (M+H)$^+$.

Example 48b

Ethyl 2-(3-methoxypyridin-2-yl)acetate

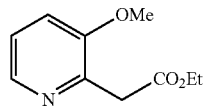 [SMILES: CCOC(=O)Cc1ncccc1OC]

The compound was prepared according to the procedure disclosed in Example 46b starting from of diethyl 2-(5-fluoropyridin-2-yl)malonate (1.0 g, 3.74 mmol). Yield: 0.63 g (87%).

$^1$H NMR (400 MHz, chloroform-d) δ ppm 8.15 (dd, 1 H), 7.18-7.22 (m, 1 H), 7.13-7.14 (m, 1 H), 4.18 (q, 2 H), 3.88 (s, 2 H), 3.84 (s, 3 H), 1.25 (t, 3 H). MS (ES+) m/z 196 (M+H)$^+$.

Example 48c 2-(3-Methoxypyridin-2-yl)ethanol

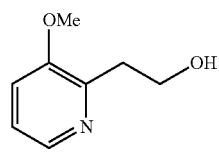 [SMILES: COc1cccnc1CCO]

The compound was prepared according to the procedure disclosed in Example 46c starting from ethyl 2-(3-methoxypyridin-2-yl)acetate (0.63 g, 3.23 mmol). Yield: 0.49 g (99%).

$^1$H NMR (400 MHz, chloroform-d) δ ppm 8.08 (dd, 1 H), 7.09-7.19 (m, 2 H), 4.05 (t, 2 H), 3.84 (s, 3 H), 3.02 (t, 2 H). MS (ES+) m/z 154 (M+H)$^+$.

Example 48d 2-(3-Methoxypyridin-2-yl)ethyl 4-methylbenzenesulfonate

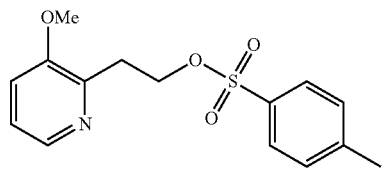 [SMILES: COc1cccnc1CCOS(=O)(=O)c1ccc(C)cc1]

The compound was prepared according to the procedure disclosed in Example 46d starting from 2-(3-methoxypyridin-2-yl)ethanol (0.49 g, 3.20 mmol). The product was purified by flash chromatography ($SiO_2$; heptane/EtOAc, gradient 0-100%). Yield: 0.62 g (63%).

$^1$H NMR (400 MHz, chloroform-d) δ ppm 8.03 (dd, 1 H), 7.74 (d, 2 H), 7.30 (d, 2 H), 7.12-7.16 (m, 1 H), 7.06-7.11 (m, 1 H), 4.45 (t, 2 H), 3.81 (s, 3 H), 3.21 (t, 2 H), 2.44 (s, 3 H). MS (ES+) m/z 308 (M+H)$^+$.

Example 49

1-(5-(2-(4-(2-(Azetidine-1-carbonyl)benzofuran-7-yl)piperazin-1-yl)ethyl)indolin-1-yl)ethanone

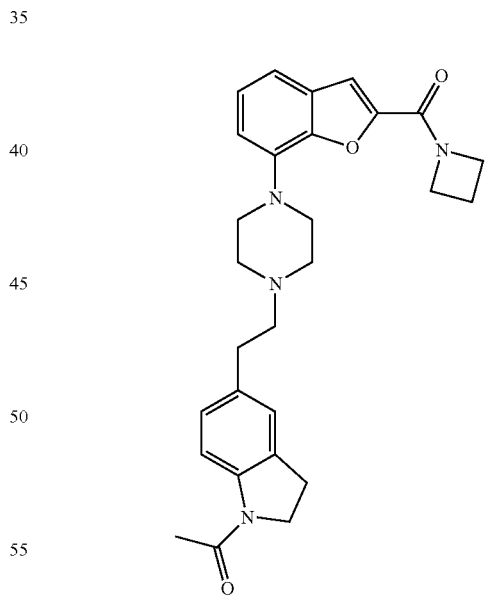

The reaction mixture of azetidin-1-yl(7-(piperazin-1-yl)benzofuran-2-yl)methanone (0.070 g, 0.25 mmol) (Example 45c), 1-(5-(2-bromoethyl)indolin-1-yl)ethanone (0.099 g, 0.37 mmol) and potassium carbonate (0.068 g, 0.49 mmol) in acetonitrile (1 mL) was heated by microwave irradiation at 120° C. for 15 min. The mixture was cooled and the solvent was removed in vacuo. The product was purified by flash chromatography ($SiO_2$; DCM/MeOH; gradient 0-5%) to give the title compound. Yield: 0.056 g (48%).

$^1$H NMR (500 MHz, acetonitrile-d$_3$) δ ppm 7.99 (d, 1 H), 7.31 (s, 1 H), 7.23-7.26 (m, 1 H), 7.19 (t, 1 H), 7.11 (s, 1 H), 7.03 (d, 1 H), 6.85-6.90 (m, 1 H), 4.63 (t, 2 H), 4.12 (t, 2 H), 4.02-4.08 (m, 2 H), 3.26-3.34 (m, 4 H), 3.14 (t, 2 H), 2.76 (t, 2 H), 2.65-2.72 (m, 4 H), 2.58-2.63 (m, 2 H), 2.38 (dt, 2 H), 2.13 (s, 3 H). MS (ES+) m/z 473 (M+H)$^+$.

The 1-(5-(2-bromoethyl)indolin-1-yl)ethanone used as a starting material was prepared as follows:

Example 49a 1-(1-Acetylindolin-5-yl)-2-bromo-ethanone

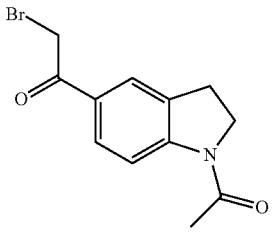 [SMILES: CC(=O)N1CCc2cc(C(=O)CBr)ccc21]

Bromoacetyl bromide (1.0 mL, 11.2 mmol) was slowly added to a suspension of aluminum chloride (3.7 g, 27.9 mmol) in dichloromethane (30 mL) and the reaction mixture was stirred for 20 min at rt. A solution of 1-acetylindoline (1.5 g, 9.3 mmol) in dichloromethane (10 mL) was slowly added and then the reaction mixture was heated at 55° C. for 1.5 h. The mixture was cooled and then quenched with cold water. The precipitate was filtered through a short pad of celite, washed with dichloromethane and water. The aqueous phase was extracted with dichloromethane. The combined organic extract was washed with brine, dried (Na$_2$SO$_4$), filtered and concentrated under reduced pressure to give the product. Yield: 1.9 g (73%).

$^1$H NMR (400 MHz, chloroform-d) δ ppm 8.27 (d, 1 H), 7.83-7.88 (m, 2 H), 4.42 (s, 2 H), 4.14 (t, 2 H), 3.27 (t, 2 H), 2.27 (s, 3 H).

Example 49b 1-(5-(2-Bromoethyl)indolin-1-yl)ethanone

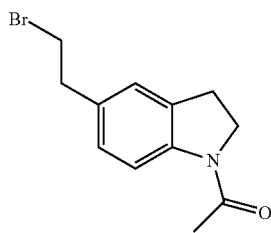

Triethylsilane (8.8 mL, 54.9 mmol) was added to a solution of 1-(1-acetylindolin-5-yl)-2-bromo-ethanone (1.9 g, 6.73 mmol) in trifluoroacetic acid (70 mL) at rt. The mixture was heated at 55° C. for 18 h, then cooled and concentrated under reduced pressure. The product was purified by flash chromatography (SiO$_2$; hexane/EtOAc; 75/25). Yield: 1.2 g (67%).

$^1$H NMR (400 MHz, chloroform-d) δ ppm 8.14 (d, 1 H), 7.01-7.05 (m, 2 H), 4.06 (t, 2 H), 3.53 (t, 2 H), 3.19 (t, 2 H), 3.11 (t, 2 H), 2.22 (s, 3 H).

Example 50

5-Fluoro-N,N-dimethyl-7-(4-(2-(pyridin-2-yl)ethyl)piperazin-1-yl)benzofuran-2-carboxamide

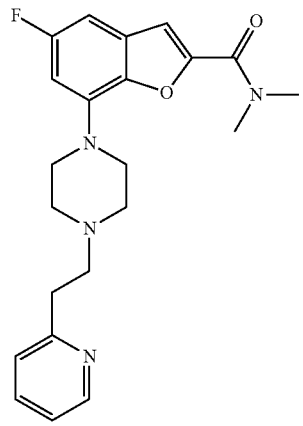 [SMILES: CN(C)C(=O)c1cc2cc(F)cc(N3CCN(CCc4ccccn4)CC3)c2o1]

A reaction mixture of 5-fluoro-N,N-dimethyl-7-(piperazin-1-yl)benzofuran-2-carboxamide (0.10 g, 0.35 mmol), 2-(2-bromoethyl)pyridine:HBr (0.132 g, 0.49 mmol) and triethylamine (0.12 mL, 0.88 mmol) was heated at 80° C. over night. The product was purified by preparative HPLC to give the title compound. Yield: 0.091 g (65%).

$^1$H NMR (500 MHz, acetonitrile-d$_3$) δ ppm 8.48 (ddd, 1 H), 7.65 (td, 1 H), 7.27 (d, 1 H), 7.20 (s, 1 H), 7.16 (ddd, 1 H), 6.89 (dd, 1 H), 6.62 (dd, 1 H), 3.30-3.37 (m, 4 H), 3.27 (br. s., 3 H), 3.05 (br. s., 3 H), 2.96 (t, 2 H), 2.74-2.82 (m, 2 H), 2.65-2.72 (m, 4 H). MS (ES+) m/z 397 (M+H)$^+$.

The 5-fluoro-N,N-dimethyl-7-(piperazin-1-yl)benzofuran-2-carboxamide used as a starting material was prepared as follows:

Example 50a

3-Bromo-5-fluoro-2-hydroxy-benzaldehyde

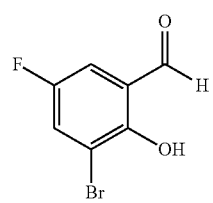 [SMILES: O=Cc1cc(F)cc(Br)c1O]

Hexamethylenetetramine (14.7 g, 105 mmol) was slowly added to a solution of 2-bromo-4-fluoro-phenol (10 g, 52.4 mmol) in trifluoroacetic acid (40 ml) at rt and heated to reflux for 18 h. The reaction mixture was cooled to rt and then water (60 ml) and sulfuric acid (30 ml, 50%) were added. The mixture was stirred for 3 h at rt and then extracted twice with ethyl acetate. The combined organic extracts were washed with 1N HCl, water, dried (Na$_2$SO$_4$), filtered and concentrated under reduced pressure to give 9.5 g (83%) of 3-bromo-5-fluoro-2-hydroxy-benzaldehyde.

$^1$H NMR (400 MHz, chloroform-d) δ ppm 9.82 (s, 1H), 7.55-7.62 (m, 1H), 7.21-7.32 (m, 1H).

Example 50b

7-Bromo-5-fluoro-benzofuran-2-carboxylic acid

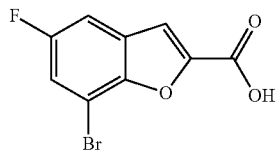 [SMILES: O=C(O)c1cc2cc(F)cc(Br)c2o1]

Methyl chloroacetate (7.6 mL, 86.8 mmol) was added to a mixture of 3-bromo-5-fluoro-2-hydroxy-benzaldehyde (9.5 g, 43.4 mmol), tetra-N-butyl-ammonium iodide (1.6 g, 4.34 mmol) and anhydrous potassium carbonate (24 g, 174 mmol). The reaction mixture was heated at 130° C. for 4 h, cooled to 0° C., diluted with tetrahydrofuran (100 mL) and then potassium hydroxide (17 g, 303 mmol) in water (100 mL). The mixture was stirred at rt for 18 h and then, concentrated under reduced pressure. The residue was acidified with HCl and extracted with ethyl acetate. The combined organic extracts were dried (Na$_2$SO$_4$), filtered and concentrated under reduced pressure. The crude compound was purified by flash chromatography (SiO$_2$; toluene/EtOAc, 40/1) to give 7.0 g (63%) of the product.

$^1$H NMR (400 MHz, methyl alcohol-d$_4$) δ ppm 7.66 (s, 1H), 7.47-7.54 (m, 2H).

Example 50c

Ethyl 7-bromo-5-fluoro-benzofuran-2-carboxylate

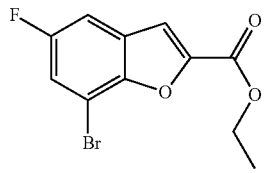 [SMILES: CCOC(=O)c1cc2cc(F)cc(Br)c2o1]

Ethyl iodide (4.6 ml, 57.2 mmol) was added to a mixture of 7-bromo-5-fluoro-benzofuran-2-carboxylic acid (3.7 g, 14.3 mmol) and sodium bicarbonate (4.8 g, 57.2 mmol) in anhydrous dimethylformamide (40 mL). The mixture was heated at 55° C. for 18 h, cooled to rt, quenched with water (20 mL) and extracted twice with ethyl acetate. The combined organic extracts were washed with brine, dried (Na$_2$SO$_4$), filtered and concentrated under reduced pressure. The crude compound was purified by flash chromatography (SiO$_2$; hexane/DCM; 4/1) to give 3.7 g (90%) of the product.

$^1$H NMR (400 MHz, chloroform-d) δ ppm 7.54 (s, 1H), 7.39-7.42 (m, 1H), 7.29-7.32 (m, 1H), 4.45 (q, 2H), 1.43 (t, 3H).

Example 50d

Ethyl-7-(4-Benzyl-piperazin-1-yl)-5-fluorobenzofuran-2-carboxylate

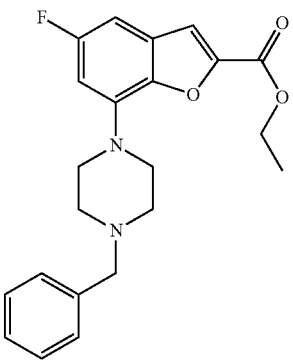 [SMILES: CCOC(=O)c1cc2cc(F)cc(N3CCN(Cc4ccccc4)CC3)c2o1]

Benzylpiperazine (1.3 mL, 8.4 mmol), BINAP (0.43 g, 0.69 mmol), Pd$_2$ dba$_3$ (0.32 g, 0.35 mmol), cesium carbonate (3.25 g, 9.76 mmol) were added to a degassed solution of 7-bromo-5-fluoro-benzofuran-2-carboxylic acid ethyl ester (2.0 g, 6.97 mmol) in toluene (50 mL). The mixture was heated at reflux over night. After cooling, the mixture was filtered through a pad of celite and washed with dichloromethane. The filtrate was concentrated under reduced pressure. The product was purified by flash chromatography (SiO$_2$; hexane/EtOAc, 7/3). Yield: 1.6 g (60%).

$^1$H NMR (400 MHz, methyl alcohol-d$_4$) δ ppm 7.51-7.63 (m, 6H), 7.03-7.08 (m, 1H), 6.79-6.84 (m, 1H), 4.47 (s, 2H), 4.41 (q, 2H), 3.21-3.70 (m, 8H), 1.40 (t, 3H).

Example 50e

Lithium 7-(4-benzylpiperazin-1-yl)-5-fluorobenzofuran-2-carboxylate

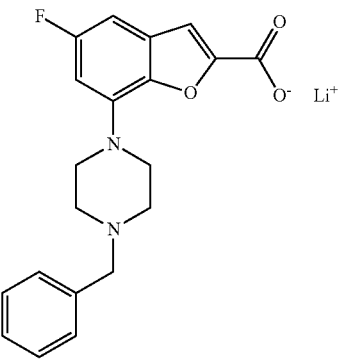 [SMILES: O=C([O-])c1cc2cc(F)cc(N3CCN(Cc4ccccc4)CC3)c2o1 ; [Li+]]

To a suspension of ethyl 7-(4-benzylpiperazin-1-yl)-5-fluorobenzofuran-2-carboxylate (1.0 g, 2.61 mmol) in tetrahydrofuran (16 mL) and water (1.8 mL) was added lithium hydroxide monohydrate (0.22 g, 5.24 mmol) and the reaction was heated at 100° C. for 45 min in a microwave oven. The reaction was heated for additional 40 min at 100° C. The precipitate formed was filtered off and the solution was evaporated. The product was dried over $P_2O_5$ in a vacuum desicator to give 0.86 g (90%) of the lithium salt as a solid. The crude was taken to the next step without further purification.

MS (ES+) m/z 355 (M+H)+ of the acid.

Example 50f 7-(4-Benzylpiperazin-1-yl)-5-fluoro-N,N-dimethyl-benzofuran-2-carboxamide

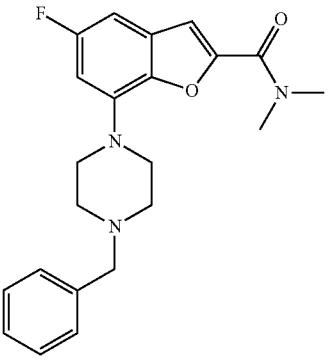 [SMILES: CN(C)C(=O)c1cc2cc(F)cc(N3CCN(Cc4ccccc4)CC3)c2o1]

Lithium 7-(4-benzylpiperazin-1-yl)-5-fluorobenzofuran-2-carboxylate (0.86 g, 2.38 mmol) was dissolved in dry dimethylformamide (10 mL), 2-succinimido-1,1,3,3-tetramethyluronium tetrafluoroborate (TSTU) (0.93 g, 3.10 mmol) was added followed by triethylamine (1.16 mL, 8.34 mmol). The reaction was stirred for 20 min then dimethylamine hydrochloride (0.78 g, 9.54 mmol) was added. The reaction was stirred at rt over night. The solvent was evaporated and water and dichloromethane were added. The layers were separated. The aqueous phase was extracted with dichloromethane (3×). The combined organic phases were washed with water (3×) and brine, dried ($Na_2SO_4$), filtered and evaporated. The crude was purified by flash chromatography ($SiO_2$; DCM/MeOH; 97/3) to give 0.62 g (68%) of the product.

$^1$H NMR (400 MHz, acetonitrile-$d_3$) δ ppm 7.34-7.41 (m, 4 H), 7.27-7.34 (m, 1 H), 7.23 (s, 1 H), 6.92 (dd, 1 H), 6.65 (dd, 1 H), 3.59 (s, 2 H), 3.34-3.40 (m, 4 H), 3.28 (br. s., 3 H), 3.07 (br. s., 3 H), 2.62-2.67 (m, 4 H). MS (ES+) m/z 382 (M+H)+.

Example 50g

5-Fluoro-N,N-dimethyl-7-(piperazin-1-yl)benzofuran-2-carboxamide

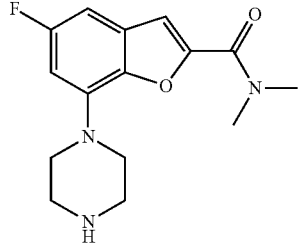 [SMILES: CN(C)C(=O)c1cc2cc(F)cc(N3CCNCC3)c2o1]

The compound was prepared according to the procedure disclosed in Example 39d starting from 7-(4-benzylpiperazin-1-yl)-5-fluoro-N,N-dimethylbenzofuran-2-carboxamide (0.60 g, 1.57 mmol). After removal of solvent, dichloromethane was added and the solution washed with saturated aqueous sodium bicarbonate. The organic layer was separated, dried ($Na_2SO_4$) and concentrated to give 0.21 g (47%) of the product.

$^1$H NMR (400 MHz, acetonitrile-$d_3$) δ ppm 7.20 (s, 1 H), 6.89 (dd, 1 H), 6.62 (dd, 1 H), 3.22-3.31 (m, 7 H), 2.94-2.99 (m, 4 H), 3.05 (br. s., 3 H). piperazine NH not seen. MS (ES+) m/z 292 (M+H)+.

Example 51

7-(4-(2-(1-Acetylindolin-5-yl)ethyl)piperazin-1-yl)-5-fluoro-N,N-dimethylbenzofuran-2-carboxamide

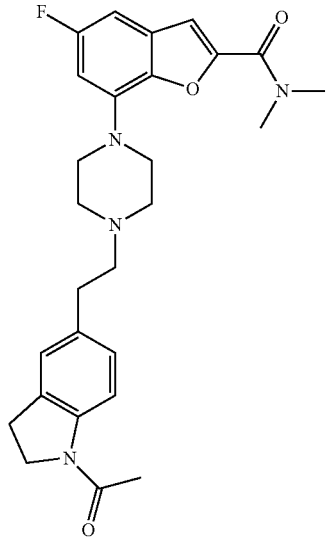 [SMILES: CC(=O)N1CCc2cc(CCN3CCN(c4cc(F)cc5cc(C(=O)N(C)C)oc45)CC3)ccc21]

The compound was prepared according to the procedure disclosed in Example 50 starting from 5-fluoro-N,N-dimethyl-7-(piperazin-1-yl)benzofuran-2-carboxamide (0.10 g, 0.35 mmol) (Example 50g) and 1-(5-(2-bromoethyl)indolin-1-yl)ethanone (0.13 g, 0.49 mmol) (Example 49b). The product was purified by preparative HPLC to give the title compound.

Yield: 0.080 g (47%).

$^1$H NMR (500 MHz, acetonitrile-$d_3$) δ ppm 8.02 (d, 1 H), 7.23 (s, 1 H), 7.13 (s, 1 H), 7.05 (d, 1 H), 6.92 (dd, 1 H), 6.66 (dd, 1 H), 4.08 (t, 2 H), 3.35-3.41 (m, 4 H), 3.30 (br. s., 3 H), 3.17 (t, 2 H), 3.08 (br. s., 3 H), 2.79 (t, 2 H), 2.67-2.73 (m, 4 H), 2.60-2.67 (m, 2 H), 2.17 (br. s., 3 H). MS m/z 479 (M+H)+.

Example 52

5-Methoxy-N,N-dimethyl-7-(4-(2-(pyridin-2-yl)ethyl)piperazin-1-yl)benzofuran-2-carboxamide

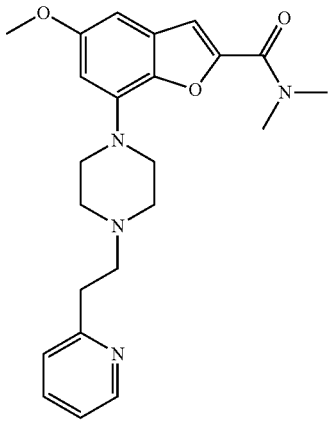

7-Bromo-5-methoxy-N,N-dimethylbenzofuran-2-carboxamide (0.20 g, 0.67 mmol), 1-(2-pyridin-2-yl-ethyl)piperazine (0.13 g, 0.67 mmol), Pd$_2$dba$_3$ (0.031 g, 0.030 mmol), 2-dicyclohexylphosphino-2',4',6'-tri-iso-propyl-1,1'-biphenyl (0.032 g, 0.070 mmol) and sodium t-butoxide (0.14 g, 1.41 mmol) were heated in toluene (1 mL) at 100° C. for 2 h. The mixture was allowed to cool. Ethyl acetate was added and the mixture was filtered through a pad of celite. The filtrate was washed with water and brine, dried over MgSO$_4$ and the solvent was removed by rotary evaporation. The crude product was purified by flash chromatography (SiO$_2$; DCM/MeOH; gradient 0-3%) to give the title compound. Yield: 0.14 g (52%).

$^1$H NMR (500 MHz, acetonitrile-d$_3$) δ ppm 8.46-8.50 (m, 1 H), 7.64 (td, 1 H), 7.25 (d, 1 H), 7.17 (s, 1 H), 7.15 (ddd, 1 H), 6.68 (d, 1 H), 6.42 (d, 1 H), 3.78 (s, 3 H), 3.20-3.35 (m, 7 H), 3.04 (br. s., 3 H), 2.95 (t, 2 H), 2.73-2.79 (m, 2 H), 2.64-2.70 (m, 4 H). MS (ES+) 409 (M+H)$^+$.

The 7-bromo-5-methoxy-N,N-dimethylbenzofuran-2-carboxamide used as a starting material was prepared as follows:

Example 52a

3-Bromo-2-hydroxy-5-methoxybenzaldehyde

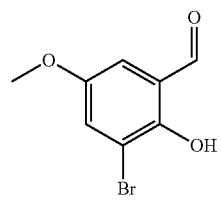

To 2-hydroxy-5-methoxybenzaldehyde (4.1 mL, 32.86 mmol) in acetic acid (150 mL) were added sodium acetate (4.0 g, 49.3 mmol) and bromine (2.2 mL, 42.7 mmol) and the mixture was stirred at rt for 2 h. Aqueous sodium thiosulfate was added and the mixture was concentrated by rotary evaporation. The solid was dissolved in dichloromethane and washed with water. The organic phase was separated, dried over MgSO$_4$, filtered and the solvent removed by rotary evaporation. The solid residue was recrystallized from ethanol to yield 3-bromo-2-hydroxy-5-methoxybenzaldehyde (4.55 g, 60%).

$^1$H NMR (500 MHz, chloroform-d) δ ppm 11.13 (s, 1 H), 9.83 (s, 1 H), 7.43 (d, 1 H), 7.04 (d, 1 H), 3.83 (s, 3 H). MS (ES−) 229, 231 (M−H)$^-$.

Example 52b

7-Bromo-5-methoxy-N,N-dimethylbenzofuran-2-carboxamide

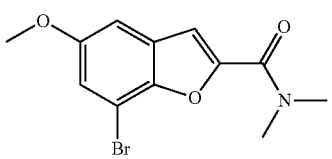

3-Bromo-2-hydroxy-5-methoxybenzaldehyde (1.5 g, 6.49 mmol), 2-chloro-N,N-dimethylacetamide (0.73 mL, 7.14 mmol) and potassium carbonate (1.8 g, 13.0 mmol) were heated to reflux in dimethylformamide (15 mL) for 2 h. The solvent was removed in vacuo and the residue was taken up in ethyl acetate and washed with water and brine. The organic phase was dried over MgSO$_4$, filtered and then concentrated by rotary evaporation. The crude product was purified by flash chromatography (SiO$_2$; heptane/EtOAc, gradient 0-100%).

Yield: 1.5 g (77%).

$^1$H NMR (500 MHz, chloroform-d) δ ppm 7.37 (s, 1 H), 7.20 (d, 1 H), 7.04 (d, 1 H), 3.85 (s, 3 H), 3.41 (br. s., 3 H), 3.16 (br. s., 3 H). MS (ES+) 298, 300 (M+H)$^+$.

Example 53

4-Bromo-N,N-dimethyl-7-(4-(2-(pyridin-2-yl)ethyl)piperazin-1-yl)benzofuran-2-carboxamide

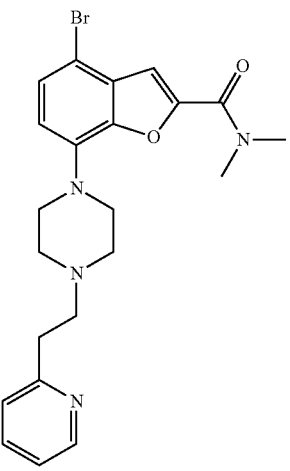 [SMILES: CN(C)C(=O)c1cc2c(Br)ccc(N3CCN(CCc4ccccn4)CC3)c2o1]

A reaction mixture of N,N-dimethyl-7-(4-(2-(pyridin-2-yl)ethyl)piperazin-1-yl)benzofuran-2-carboxamide (0.50 g, 1.32 mmol) (Example 11) and N-bromosuccinimide (0.12 mL, 1.45 mmol) in dichloromethane (10 mL) was stirred at rt for 1.5 h. The solvent was removed in vacuo. The product was purified by flash chromatography (SiO$_2$; DCM/MeOH; gradient 0-3%) to give the title compound. Yield: 0.55 g (91%).

$^1$H NMR (400 MHz, acetonitrile-d$_3$) δ ppm 8.46-8.51 (m, 1 H), 7.65 (td, 1 H), 7.35 (d, 1 H), 7.24-7.29 (m, 1 H), 7.18 (s, 1 H), 7.13-7.18 (m, 1 H), 6.78 (d, 1 H), 3.21-3.34 (m, 7 H), 3.06 (br. s., 3 H), 2.93-2.99 (m, 2 H), 2.75-2.82 (m, 2 H), 2.65-2.73 (m, 4 H). MS (ES+) m/z 457, 459 (M+H)$^+$.

All solvents used were of analytical grade and commercially available anhydrous solvents were routinely used for reactions. Starting materials used were available from commercial sources, or prepared according to literature procedures. Room temperature refers to about 20-25° C. Solvent mixture compositions are given as volume percentages or volume ratios.

Microwave heating was performed in a Creator, Initiator or Smith Synthesizer Single-mode microwave cavity producing continuous irradiation at 2450 MHz. It is understood that microwaves can be used for the heating of reaction mixtures.

General Methods

Thin layer chromatography (TLC) was performed on Merck TLC-plates (Silica gel 60 F254) and UV visualized the spots. Straight phase flash column chromatography purifications were performed on silica gel either manually or performed on a Combi Flash® Companion™ using RediSep™ normal-phase flash columns using the solvent system indicated.

NMR spectroscopy was performed on a Bruker DPX400 NMR spectrometer operating at 400 MHz for $^1$H, equipped with a 4-nucleus probe-head with Z-gradients. Alternatively, NMR spectroscopy was performed on a Bruker DRX400.NMR spectrometer operating at 400 MHz for 1H, equipped with a 2-nucleus probe-head with Z-gradients. Alternatively, NMR spectroscopy was performed on a Bruker 500 MHz Avance III NMR spectrometer, operating at 500 MHz for $^1$H, equipped with a 5 mm TCI cryogenically cooled probe-head with Z-gradients. Alternatively, NMR spectroscopy was performed on a Bruker DRX600 NMR spectrometer, operating at 600 MHz for $^1$H, equipped with a 5 mm TXI probe-head with Z-gradients. The following reference signals were used: the middle line of $CD_3CN$ δ 1.94; the middle line of $(CD_3)_2SO$ δ 2.50 ($^1$H), the middle line of $CD_3OD$ δ 3.31 ($^1$H); or $CDCl_3$ δ 7.26 ($^1$H) unless otherwise indicated. All experiments were performed at a sample temperature of 20-30° C. unless otherwise stated.

LC-MS analyses were performed on an LC-MS system consisting of a Waters Alliance 2795 HPLC, a Waters PDA 2996 diode array detector, a Sedex 75 ELS detector and a ZQ 2000 single quadrupole mass spectrometer. The mass spectrometer was equipped with an electrospray ion source (ES) operated in positive and negative ion mode. Separation was is performed on a Xbridge C18, 30×50 mm, 3.5 μm column or on a Gemini C18 3.0×50, 3 μm (Phenomenex) column run at a flow rate of 1 mL/min. Alternatively, LC-MS analyses were performed on an LC-MS consisting of a Waters sample manager 2777C, a Waters 1525μ binary pump, a Waters 1500 column oven, a Waters ZQ single quadrupole mass spectrometer, a Waters PDA2996 diode array detector and a Sedex 85 ELS detector. The mass spectrometer was equipped with an electrospray ion source (ES) operated in positive and negative ion mode. The column used was a Xbridge C18, 30×50 mm, 3.5 μm or a Gemini C18, 3.0 mm×50 mm, 3 μm, (Phenomenex) which was run at a flow rate of 1 mL/min. Typical mobile phase systems for LCMS consisted of Mobile phase A: 10 mM ammonium acetate (aq.) in 5% methanol and mobile phase B: methanol or Mobile phase A: 10 mM ammonium acetate (aq.) in 5% acetonitrile and mobile phase B: acetonitrile Linear gradients from 100% A to 100% B was typically applied.

Preparative HPLC was performed on a Waters Auto purification HPLC-UV system with a diode array detector using a Waters XTerra MS $C_8$ column (19×300 mm, 7 μm) or a XBridge® Prep C18 10 μm OBD™ (19×250 mm) and a linear gradient of mobile phase B was applied, flow rate: 20 mL/min. Mobile phase is either Mobile phase A: 0.1 M ammonium acetate (aq.) in water/acetonitrile (95:5) and mobile phase B: acetonitrile or mobile phase A: 0.1 M ammonium acetate (aq.) in water/methanol (95:5) and mobile phase B: methanol.

Preparative chromatography for library compounds was run on a Waters FractionLynx system with a Autosampler combined Automated Fraction Collector (Waters 2767), Gradient Pump (Waters 2525), Regeneration Pump (Waters 600), Make Up Pump (Waters 515), Waters Active Splitter, Column Switch (Waters CFO), PDA (Waters 2996) and Waters ZQ mass spectrometer. The column was a XBridge™ Prep C8 5 μm OBD™ 19×100 mm, with guard column; XTerra® Prep MS C8 10 μm 19×10 mm Cartridge. A gradient from 100% A (A: 95% 0.1 M $NH_4OAc$ in MilliQ water and 5% MeCN) to 100% B (B: 100% MeCN) was applied for LC-separation at flow rate 25 mL/minute. The PDA was scanned from 210-350 nm. The ZQ mass spectrometer was run with ES ionization in positive mode. The capillary voltage was 3 kV and the cone voltage was 30 V. Mixed triggering, UV and MS signal, determined the fraction collection.

Compounds have been named using CambridgeSoft MedChem ELN v2 or ACD/Name, version 10.0 or 10.6, software from Advanced Chemistry Development Inc. (ACD/Labs), Toronto ON Canada, www.acdlabs.com, or Lexichem, version 1.7, software from OpenEye.

Pharmaceutical Formulations

According to one aspect of the present invention there is provided a pharmaceutical formulation comprising the compound of formula (I) as a free base or a pharmaceutically acceptable salt thereof, in an essentially pure and isolated form, for use in the prevention and/or treatment of conditions associated with 5-HT1A and 5-HT1B receptors.

The formulation used in accordance with the present invention may be in a form suitable for oral administration, for example as a tablet, pill, syrup, powder, granule or capsule, for parenteral injection (including intravenous, subcutaneous, intramuscular, intravascular or infusion) as a solution, suspension or emulsion, for topical administration as an ointment, patch or cream, for rectal administration as a suppository and for local administration in a body cavity or in a bone cavity.

In general the above formulation may be prepared in a conventional manner using pharmaceutically carriers or diluents.

Suitable daily doses of the compound of formula (I) as a free base and pharmaceutically acceptable salts thereof in the treatment of a mammal, including human, are approximately 0.01 to 250 mg/kg bodyweight at per oral administration and about 0.001 to 250 mg/kg bodyweight at parenteral administration. The typical daily dose of the active ingredients varies within a wide range and will depend on various factors such as the relevant indication, the route of administration, the age, weight and sex of the patient and may be determined by a physician.

The compound of formula (I) as a free base or a pharmaceutically acceptable salt thereof, in an essentially pure and isolated form, may be used on its own but will usually be administered in the form of a pharmaceutical formulation in which the active ingredient is in association with pharmaceutically acceptable diluents, excipients and/or inert carrier known to a person skilled in the art. Dependent on the mode of administration, the pharmaceutical formulation may comprise from 0.05 to 99% w (percent by weight), for example from 0.10 to 50% w, of active ingredient, all percentages by weight being based on total composition.

A formulation of the invention can be in a unit dosage form such as a tablet or an injectable solution.

The invention further provides a process for the preparation of a pharmaceutical formulation of the invention which comprises mixing of the compound of formula (I) or a pharmaceutically acceptable salt thereof, a hereinbefore defined, with pharmaceutically acceptable diluents, excipients and/or inert carriers.

A suitable pharmaceutically acceptable salt of the compound of formula (I) useful in accordance to the invention is, for example, an acid-addition salt, which is sufficiently basic, for example an inorganic or organic acid. In addition a suitable pharmaceutically acceptable salt of the compounds of the invention, which is sufficiently acidic, is an alkali metal salt, an alkaline earth metal salt or a salt with an organic base, which affords a physiologically-acceptable cation.

The compounds of the invention will normally be administered orally, subcutaneously, intravenously, intraarterially, transdermally, intranasally, by inhalation, or by any other parenteral route, in the form of pharmaceutical preparations comprising the active ingredient either as a free base or a non-toxic organic or inorganic acid addition salt, in a pharmaceutically acceptable dosage form. Depending upon the disorder and patient to be treated, as well as the route of administration, the compositions may be administered at varying doses.

One embodiment relates to a pharmaceutical composition comprising as active ingredient a therapeutically effective amount of the compound of formula (I) as defined above, in association with one or more pharmaceutically acceptable diluents, excipients and/or inert carriers.

Another embodiment relates to said pharmaceutical composition according, for use in the treatment of cognitive disorders such as Alzheimer's Disease, Bipolar Disorder (BD) including acute mania, bipolar depression, bipolar maintenance; or Major Depressive Disorders (MDD) including depression, major depression and mood disorder (stabilization).

Suitable daily doses of the compounds of the invention in therapeutic treatment of humans are about 0.005 to 25.0 mg/kg body weight at oral administration and about 0.005 to 10.0 mg/kg body weight at parenteral administration. Example of ranges of daily doses of the compounds of the invention in therapeutic treatment of humans are about 0.005 to 10.0 mg/kg body weight at oral administration and about 0.005 to 5.0 mg/kg body weight at parenteral administration.

Medical Uses

It has been found that the compounds of formula (I) defined in the present invention, are well suited for binding to the 5-HT1A and 5-HT1B receptors and modulating the effects of serotonin and thereby also to increase levels of acetylcholine and/or glutamate. Accordingly, said compound of the present invention is expected to be useful in the prevention and/or treatment of conditions associated with disturbances in 5-HT signalling mediated by 5-HT1A and 5-HT1B receptors, i.e. the compounds may be used to produce an increased levels of acetylcholine, glutamate, serotonin in mammals, including human, in need of such prevention and/or treatment.

Thus, it is expected that compound of the invention is well suited for the prevention and/or treatment of conditions associated with serotonergic dysfunction mediated via the 5-HT1A and 5-HT1B receptors in the central and peripheral nervous system. In particular, the compound of the invention is expected to be suitable for prevention and/or treatment of conditions associated with cognitive disorder(s) or indications with deficit(s) in cognition such as: dementia; incl. pre-senile dementia (early onset Alzheimer's Disease); senile dementia (dementia of the Alzheimer's type); Alzheimer's Disease (AD); Familial Alzheimer's disease; Early Alzheimer's disease; mild to moderate dementia of the Alzheimer's type; delay of disease progression of Alzheimer's Disease; neurodegeneration associated with Alzheimer's disease, Mild Cognitive Impairment (MCI); Amnestic Mild Cognitive Impairment (aMCI); Age-associated Memory Impairment (AAMI); Lewy body dementia; vascular dementia (VD); HIV-dementia; AIDS dementia complex; AIDS—Neurological Complications; Frontotemporal dementia (FTD); Frontotemporal dementia Parkinson's Type (FTDP); dementia pugilistica; dementia due to infectious agents or metabolic disturbances; dementia of degenerative origin; dementia—Multi-Infarct; memory loss; cognition in Parkinson's Disease; cognition in multiple sclerosis; cognition deficits associated with chemotherapy; Cognitive Deficit in Schizophrenia (CDS); Schizoaffective disorders including schizophrenia; Age-Related Cognitive Decline (ARCD); Cognitive Impairment No Dementia (CIND); Cognitive Deficit arising from stroke or brain ischemia; Congenital and/or development disorders; progressive supranuclear palsy (PSP); amyotrophic lateral sclerosis (ALS); corticobasal degeneration(CBD); traumatic brain injury (TBI); postencephalitic parkinsonism; Pick's Disease; Niemann-Pick's Disease; Down's syndrome; Huntington's Disease; Creuztfeld-Jacob's disease; prion diseases; multiple sclerosis (MS); motor neuron diseases (MND); Parkinson's Disease (PD); β-amyloid angiopathy; cerebral amyloid angiopathy; Trinucleotide Repeat Disorders; Spinal Muscular Atrophy; Friedreich's Ataxia; Neuromyelitis Optica; Multiple System Atrophy; Transmissible Spongiform Encephalopathies; Attention Deficit Disorder (ADD); Attention Deficit Hyperactivity Disorder (ADHD); Bipolar Disorder (BD) including acute mania, bipolar depression, bipolar maintenance; Major Depressive Disorders (MDD) including depression, major depression, mood disorder (stabilization), dysthymia; agnosia; aphasia; apraxia; apathy.

One embodiment of the invention relates to the prevention and/or treatment of Alzheimer's Disease.

Other embodiments of the invention relate to the prevention and/or treatment of disorders selected from the group consisting of attention deficit disorder (ADD), attention deficit hyperactivity disorder (ADHD).

Other embodiments of the invention relate to the prevention and/or treatment of disorders selected from the group consisting of affective disorders or mood disorders, wherein the affective disorders or mood disorders are Bipolar Disorder including acute mania, bipolar depression, bipolar maintenance, major depressive disorders (MDD) including depression, major depression, seasonal affective disorder, mood disorder (stabilization), panic disorder with/without agoraphobia, social phobia, specific phobia, generalized anxiety disorder (GAD), posttraumatic stress disorder, personality disorders (disorders of impulse control, trichotellomania), obsessive compulsive disorders (OCD), pathological aggression, rage outburst, schizoaffective disorders including schizophrenia, and dysthymia.

Another embodiment of the compound of the invention is its use for treatment of conditions selected from the group consisting of pain, neuropathic pain, nociceptive pain, chronic pain, pain associated with cancer, pain associated with rheumatic disease and migraine.

Another embodiment of the compound of the invention is its use for treatment of conditions selected from the group consisting of urinary incontinence and over active bladder (OAB).

Another embodiment of the compound of the invention is its use for treatment of conditions selected from the group consisting of Functional Gastrointestinal Disorders such as Irritable bowel syndrome (IBS) and Functional Dyspepsia (FD) such as ulcer-like dyspepsia and dysmotility-like dyspepsia.

Furthermore, one embodiment of the compounds of the invention relates to the prevention and/or treatment of disorders are disorders in the vasospasm and growth control of tumors (e.g. lung carcinoma and prostate cancer).

Yet an embodiment of the compound of the invention is its use for treatment of conditions are selected from the group consisting of sexual disturbances, erection dysfunction, obesity, anorexia, bulimia, cachexia, premenstrual syndrome, abuses (e.g. alcoholism, tobacco abuse), autism, Tourette's syndrome, dyslexia, endocrine disorders (e.g. hyperprolactinaemia), stroke, dyskinesia, thermoregulation, sleep disorders (e.g. apnea, narcolepsy, hypersomnia) and hypertension.

The present invention relates also to the use of the compound of formula (I) as defined in the present invention in the manufacture of a medicament for the prevention and/or treatment of conditions associated with serotonergic dysfunction mediated via the 5-HT1A and 5-HT1B receptors.

The invention also provides for a method of treatment and/or prevention of conditions associated with serotonergic dysfunction mediated via the 5-HT1A and 5-HT1B receptors comprising administering to a mammal, including human in need of such treatment and/or prevention a therapeutically effective amount of the compound of formula (I) as defined in the present invention.

The dose required for the therapeutic or preventive treatment of a particular disease will necessarily be varied depending on the host treated, the route of administration and the severity of the illness being treated.

In the context of the present specification, the term "therapy" or "treatment" also includes "prevention" unless there are specific indications to the contrary. The terms "therapeutic" and "therapeutically" should be construed accordingly.

In the context of the present specification, the term "disorder" also includes "condition" unless there are specific indications to the contrary.

Another aspect of the invention is wherein a compound of formula (I) or a pharmaceutically acceptable salt thereof as defined herein, or a pharmaceutical composition or formulation comprising a combination comprising such a compound of formula (I) is administered, concurrently, simultaneously, sequentially, separately or adjunct with another pharmaceutically active compound or compounds selected from the following:

(i) antidepressants such as agomelatine, amitriptyline, amoxapine, bupropion, citalopram, clomipramine, desipramine, doxepin duloxetine, elzasonan, escitalopram, fluvoxamine, fluoxetine, gepirone, imipramine, ipsapirone, maprotiline, nortriptyline, nefazodone, paroxetine, phenelzine, protriptyline, ramelteon, reboxetine, robalzotan, sertraline, sibutramine, thionisoxetine, tranylcypromaine, trazodone, trimipramine, venlafaxine and equivalents and pharmaceutically active isomer(s) and metabolite(s) thereof (ii) atypical antipsychotics including for example quetiapine and pharmaceutically active isomer(s) and metabolite(s) thereof.

(iii) antipsychotics including for example amisulpride, aripiprazole, asenapine, benzisoxidil, bifeprunox, carbamazepine, clozapine, chlorpromazine, debenzapine, divalproex, duloxetine, eszopiclone, haloperidol, iloperidone, lamotrigine, loxapine, mesoridazine, olanzapine, paliperidone, perlapine, perphenazine, phenothiazine, phenylbutylpiperidine, pimozide, prochlorperazine, risperidone, sertindole, sulpiride, suproclone, suriclone, thioridazine, trifluoperazine, trimetozine, valproate, valproic acid, zopiclone, zotepine, ziprasidone and equivalents and pharmaceutically active isomer(s) and metabolite(s) thereof (iv) anxiolytics including for example alnespirone, azapirones, benzodiazepines, barbiturates such as adinazolam, alprazolam, balezepam, bentazepam, bromazepam, brotizolam, buspirone, clonazepam, clorazepate, chlordiazepoxide, cyprazepam, diazepam, diphenhydramine, estazolam, fenobam, flunitrazepam, flurazepam, fosazepam, lorazepam, lormetazepam, meprobamate, midazolam, nitrazepam, oxazepam, prazepam, quazepam, reclazepam, tracazolate, trepipam, temazepam, triazolam, uldazepam, zolazepam and equivalents and pharmaceutically active isomer(s) and metabolite(s) thereof.

(v) anticonvulsants including for example carbamazepine, clonazepam, ethosuximide, felbamate, fosphenyloin, gabapentin, lacosamide, lamotrogine, levetiracetam, oxcarbazepine, phenobarbital, phenyloin, pregabaline, rufinamide, topiramate, valproate, vigabatrine, zonisamide, and equivalents and pharmaceutically active isomer(s) and metabolite(s) thereof.

(vi) Alzheimer's therapies including for example donepezil, rivastigmine, galantamine, memantine, and equivalents and pharmaceutically active isomer(s) and metabolite(s) thereof (vii) Parkinson's therapies including for example levodopa, dopamine agonists such as apomorphine, bromocriptine, cabergoline, pramipexol, ropinirole, and rotigotine, MAO-B inhibitors such as selegeline and rasagiline, and other dopaminergics such as tolcapone and entacapone, A-2 inhibitors, dopamine reuptake inhibitors, NMDA antagonists, Nicotine agonists, and inhibitors of neuronal nitric oxide synthase and equivalents and pharmaceutically active isomer(s) and metabolite(s) thereof.

(viii) migraine therapies including for example almotriptan, amantadine, bromocriptine, butalbital, cabergoline, dichloralphenazone, dihydroergotamine, eletriptan, frovatriptan, lisuride, naratriptan, pergolide, pizotiphen, pramipexole, rizatriptan, ropinirole, sumatriptan, zolmitriptan, zomitriptan, and equivalents and pharmaceutically active isomer(s) and metabolite(s) thereof (ix) stroke therapies including for example thrombolytic therapy with eg activase and desmoteplase, abciximab, citicoline, clopidogrel, eptifibatide, minocycline, and equivalents and pharmaceutically active isomer(s) and metabolite(s) thereof.

(x) urinary incontinence therapies including for example darafenacin, falvoxate, oxybutynin, propiverine, robalzotan, solifenacin, tolterodine and equivalents and pharmaceutically active isomer(s) and metabolite(s) thereof.

(xi) neuropathic pain therapies including lidocain, capsaicin, and anticonvulsants such as gabapentin, pregabalin, and antidepressants such as duloxetine, venlafaxine, amitriptyline, klomipramine, and equivalents and pharmaceutically active isomer(s) and metabolite(s) thereof.

(xii) nociceptive pain therapies including paracetamol, NSAIDS and coxibs, such as celecoxib, etoricoxib, lumiracoxib, valdecoxib, parecoxib, diclofenac, loxoprofen, naproxen, ketoprofen, ibuprofen, nabumeton, meloxicam, piroxicam and opioids such as morphine, oxycodone, buprenorfin, tramadol and equivalents and pharmaceutically active isomer(s) and metabolite(s) thereof.

(xiii) insomnia therapies including for example agomelatine, allobarbital, alonimid, amobarbital, benzoctamine, butabarbital, capuride, chloral, cloperidone, clorethate, dexclamol, ethchlorvynol, etomidate, glutethimide, halazepam, hydroxyzine, mecloqualone, melatonin, mephobarbital, methaqualone, midaflur, nisobamate, pentobarbital, phenobarbital, propofol, ramelteon, roletamide, triclofos, secobarbital, zaleplon, zolpidem and equivalents and pharmaceutically active isomer(s) and metabolite(s) thereof.

(xiv) mood stabilizers including for example carbamazepine, divalproex, gabapentin, lamotrigine, lithium, olanzapine, quetiapine, valproate, valproic acid, verapamil, and equivalents and pharmaceutically active isomer(s) and metabolite(s) thereof. Such combination products employ the compound of this invention within the dosage range described herein and the other pharmaceutically active compound or compounds within approved dosage ranges and/or the dosage described in the publication references.

In one embodiment of the invention the combination comprises the group of compounds (a) and (b) as defined below:
(a) a first therapeutic agent, which is a (a) 5-HT1A and 5-HT1B receptors modulator and (b) a second therapeutic agent, which is latrepiridine.
(a) a first therapeutic agent, which is (a) N,N-Dimethyl-7-(4-(2-(pyridin-2-yl)ethyl)piperazin-1-yl)benzofuran-2-carboxamide and (b) a second therapeutic agent, which is latrepiridine.
(a) a first therapeutic agent, which is a (a) 5-HT1A and 5-HT1B receptors modulator and (b) a second therapeutic agent, which is an acetylcholineesterase inhibitor.
(a) a first therapeutic agent, which is (a) N,N-Dimethyl-7-(4-(2-(pyridin-2-yl)ethyl)piperazin-1-yl)benzofuran-2-carboxamide and (b) a second therapeutic agent, which is donepezil;
(a) a first therapeutic agent, which is (a) N,N-Dimethyl-7-(4-(2-(pyridin-2-yl)ethyl)piperazin-1-yl)benzofuran-2-carboxamide and (b) a second therapeutic agent, which is memantine;
(a) a first therapeutic agent, which is (a) N,N-Dimethyl-7-(4-(2-(pyridin-2-yl)ethyl)piperazin-1-yl)benzofuran-2-carboxamide and (b) a second therapeutic agent, which is rivastigmine;
(a) a first therapeutic agent, which is (a) N,N-Dimethyl-7-(4-(2-(pyridin-2-yl)ethyl)piperazin-1-yl)benzofuran-2-carboxamide and (b) a second therapeutic agent, which is galantamine.

Biological Tests

Assays that were used to measure affinity of the compounds of the present invention for 5-HT1A and 5-HT1B receptors are described in J. Recept Signal Transduct. Res. 22:483-495 (2002) and Naunyn-Schmiedeberg's Arch Pharmacol. 356:328-334 (1997) and incorporated by reference herein. These assays were be used with some modifications:

For the binding assay stably transfected chinese hamster ovary (CHO) cell lines expressing 5-HT1A receptors or 5-HT1B receptors were harvested by centrifugation at 300×g for 10 min and resuspended in 10 mM Tris-HCl, 5 mM EDTA at pH 7.4. The cells were pooled, recentrifuged and resuspended before homogenisation using a Dounce homogeniser ("type B"). Cell membranes were centrifuged at 48 000×g for 10 min and then resuspended in harvesting buffer using an Ultra-Turrax T8 (IKA Labortechnik, Germany), aliquots were stored frozen in −70° C.

Frozen membrane preparations were thawed, homogenized with an Ultra-Turrax and mixed with SPA beads (YSI coated WGA, GE Healthcare/Amersham, Buckinghamshire, UK) in assay buffer containing 50 mM Tris-Base, 4 mM $MgCl_2$, 4 mM $CaCl_2$ (only 5-$HT_{1B}$), 1 mM EDTA, and adjusted to pH 7.4 with HCl. The beads/membrane solution, final concentration 100 pM receptors for 5-$HT_{1A}$, 300 pM receptors for 5-HT1B and 0.5 mg SPA beads/well, was pre-incubated in room temperature with stirring for 30-60 min. Test compounds were evaluated in competition binding assays using [$^3$H]-8-OH-DPAT (GE Healthcare/Amersham, Buckinghamshire, UK) for the 5-HT1A receptor and [$^3$H]-GR125743 (GE Healthcare/Amersham, Buckinghamshire, UK) for the 5-HT1B receptor at a concentration of 0.15-0.2 nM for both radioligands. Five (log interval, 10 µM to 1 nM, final concentration) or ten serial dilutions (½-log interval, 10 µM to 0.32 nM, final concentration) of compounds were prepared in DMSO from 10 mM stock solutions. The binding assays were performed in 384-well plates in a final volume of 90 µL/well with the following additions: 9 µL binding buffer; 1 µL compound/DMSO/nonspecific; 20 µL radioligand; and 60 µL beads/membrane mixture. Non-specific binding was defined by using 10 µM WAY100635 for 5-$HT_{1A}$ and 10 µM Methiothepin for 5-HT1B. The assay plates were incubated for 4 hours where after the plates are counted in a Wallac 1450 Microbeta Trilux counter (PerkinElmer LifeScience, US) or similar. Data from the experiments were analyzed using a four parameter logistic equation as follows: Y=Bottom+(Top-Bottom)/1+10$^{(LogEC50-X)nH}$. The $K_d$ values used in the calculation of the $K_i$ values were determined in saturation binding studies, and were 0.56 nM for [$^3$H]-8-OH-DPAT and 0.87 nM for [$^3$H]-GR125743. The obtained data is shown in Table 1.

References

Jerning E., Rosqvist S., Mohell N. (2002) NAD-299 antagonises 5-HT-stimulated and Spiperone-inhibited [$^{35}$S]GTPγS binding in cloned 5-$HT_{1A}$ receptors. J Recept Signal Transduct Res 22:483-495.

Doménech T., Beleta J., Palacios J. M. (1997) Characterization of human serotonin 1D and 1B receptors using [$^3$H]-GR-125743, a novel radiolabelled serotonin 5HT1D/1B receptor antagonist. Naunyn-Schmiedeberg's Arch Pharmacol 356:328-334.

TABLE 1

| Example nr | 5HT1A Mean Ki (nM) | 5HT1B Mean Ki (nM) |
|---|---|---|
| 1 | 1.3 | 19 |
| 2 | 1.3 | 1.1 |
| 3 | 0.14 | 0.52 |
| 4 | 0.2 | 1.8 |
| 5 | 2.2 | 37 |
| 6 | 6.4 | 82 |
| 7 | 0.59 | 9 |
| 8 | 0.29 | 0.28 |
| 9 | 0.44 | 1.8 |
| 10 | 0.38 | 0.89 |
| 11 | 0.16 | 2.1 |
| 12 | 0.11 | 0.88 |
| 13 | 0.55 | 6.5 |
| 14 | 3.3 | 42 |
| 15 | 1.4 | 16 |
| 16 | 0.78 | 4.4 |
| 17 | 2 | 3.3 |
| 18 | 1.3 | 0.7 |
| 19 | 0.99 | 10 |
| 20 | 1.1 | 7.6 |
| 21 | 2.6 | 63 |
| 22 | 0.91 | 9.1 |
| 23 | 4.2 | 1.4 |
| 24 | 0.42 | 0.56 |
| 25 | 2.9 | 31 |
| 26 | 0.91 | 2.3 |
| 27 | 2.3 | 35 |
| 28 | 0.85 | 1 |
| 29 | 2 | 19 |
| 30 | 1.1 | 17 |
| 31 | 1.5 | 50 |
| 32 | 12 | 280 |
| 33 | 2.1 | 44 |
| 34 | 3.8 | 38 |
| 35 | 2 | 34 |
| 36 | 1.9 | 0.46 |
| 37 | 0.23 | 3.5 |
| 38 | 0.064 | 1.6 |
| 39 | 0.32 | 66 |
| 40 | 0.14 | 1.3 |
| 41 | 1.3 | 73 |
| 42 | 0.64 | 7 |
| 43 | 0.33 | 2 |
| 44 | 3.7 | 20 |
| 45 | 0.34 | 2.4 |
| 46 | 1.3 | 1.4 |
| 47 | 0.22 | 19 |
| 48 | 0.16 | 7.7 |

TABLE 1-continued

| Example nr | 5HT1A Mean Ki (nM) | 5HT1B Mean Ki (nM) |
|---|---|---|
| 49 | 0.16 | 14 |
| 50 | 0.43 | 8.2 |
| 51 | 0.23 | 5 |
| 52 | 2.8 | 140 |
| 53 | 0.35 | 11 |

The following abbreviations have been used
aq aqueous
eq equivalents
BINAP 2,2'-bis(diphenylphosphino)-1,1'-binaphtalene
CDI 1-1'-carbonyldiimidazole
DABAL-Me$_3$ Bis(trimethylaluminum)-1,4-diazabicyclo[2.2.2]octane adduct
dba dibenzylideneacetone
DCC 1,3-dicyclohexylcarbodiimide
DCM dichloromethane
DIPEA N,N-diisopropylethylamine
DMAP N,N-dimethyl-4-aminopyridine
DMA N,N-dimethylacetamide
DMF N,N-dimethylformamide
DMSO dimethylsulfoxide
EtOH ethanol
EtOAc ethyl acetate
MeOH methanol
MeCN acetonitrile
THF tetrahydrofuran
HATU O-(7-azabenzotriazol-1-yl)-N,N,N',N'-tetramethyluronium hexafluorophosphate
HBTU O-benzotriazol-1-yl-N,N,N',N'-tetra-methyluronium hexafluorophosphate
HOBt 1-Hydroxybenzotriazole hydrate
MIDA N-methyliminodiacetic acid
TBTU O-benzotriazolyl tetramethylisouronium tetrafluoroborate
TSTU 2-succinimido-1,1,3,3-tetramethyluronium tetrafluoroborate
X-phos 2-dicyclohexylphosphino-2',4',6'-triisopropylbiphenyl
CI chemical ionization
ELS evaporative light scattering
ES electro-spray
HPLC high performance liquid chromatography
LC liquid chromatography
MS mass spectroscopy
NMR nuclear magnetic resonance
PDA photodiode array detector
TLC thin layer chromatography
UPLC ultra performance
UV ultra violet
XRDP X-Ray Powder Diffraction
Cu Kα Cupper Kalpha radiation
δ chemical shift in parts per million (ppm) downfield from the standard
s singlet
d doublet
t triplet
q quartet
m multiplet
dd doublet of doublet
dt doublet of triplet
td triplet of doublet
br broadened

The invention claimed is:

1. A compound of formula (I),

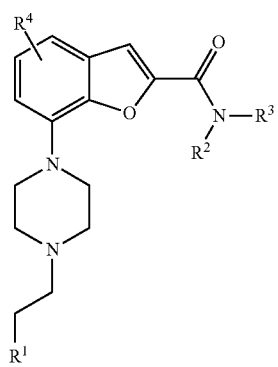

wherein $R^1$ is pyridinyl or indolinyl, wherein said pyridinyl or indolinyl is optionally substituted with one or more substituents selected from the group consisting of $C_{1-4}$alkyl, halogen, $CF_3$, CN, $C_{1-4}$alkoxy, —C(O)$C_{1-4}$alkyl, —N$C_{1-4}$alkylC(O)$C_{1-4}$alkyl, —NHC(O)$C_{1-4}$alkyl, —C(O)HN($C_{1-4}$alkyl) and —C(O)N($C_{1-4}$alkyl)$_2$;

$R^2$ is $C_{1-4}$alkyl, heterocyclyl, —$C_{1-4}$alkyl-phenyl, —$C_{1-4}$alkylheteroaryl, carbocyclyl, —$C_{1-4}$alkylheterocyclyl, -heterocyclyl-heteroaryl, -phenyl-heterocyclyl, -carbocyclyl-heteroaryl, -heterocyclyl-phenyl, wherein in said groups the heterocyclyl, phenyl, heteroaryl or carbocyclyl moiety may be optionally substituted with one or more substituents selected from the group consisting of halogen, $C_{1-4}$alkoxy, —C(O)$C_{1-4}$alkyl, —$C_{0-4}$alkylSO$_2$$C_{1-4}$alkyl, cyano, hydroxy, and —$C_{1-4}$alkyl;

$R^3$ is hydrogen or $C_{1-4}$alkyl, or $R^2$ and $R^3$ may together with the nitrogen atom, form a saturated ring system containing 4, 5 or 6 ring forming atoms selected from carbon or nitrogen and wherein said ring system is optionally substituted with one or more substituent selected from halogen, $C_{1-4}$alkyl and $C_{1-4}$alkoxy, —O-heteroaryl;

$R^4$ is hydrogen, halogen, methyl or methoxy;

wherein heteroaryl is a monocyclic aromatic heterocycle containing 1 or 2 heteroatoms that are each independently nitrogen, sulphur, or oxygen; or benzodioxolyl; and heterocyclyl is a saturated monocyclic ring containing 3 to 7 atoms of which 1 or 2 ring atoms are each independently nitrogen, sulphur, or oxygen;

or a pharmaceutically acceptable salt thereof.

2. The compound according to claim 1, wherein $R^1$ is indolinyl.

3. The compound according to claim 1, wherein $R^1$ is pyridinyl.

4. The compound according to claim 1, wherein $R^2$ is —$C_{1-4}$alkylheteroaryl and wherein said heteroaryl is pyridinyl, pyrimidinyl, imidazolyl, pyrazolyl or benzodioxolyl.

5. The compound according to claim 1, wherein $R^2$ and $R^3$ are $C_{1-4}$alkyl.

6. The compound of formula (I),

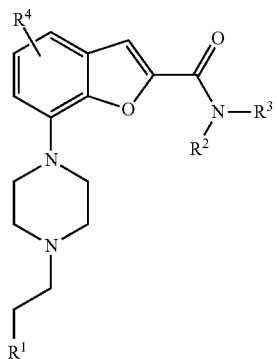

wherein
R¹ is pyridine-2-yl;
R² is $C_{1-4}$alkyl, heterocyclyl, —$C_{1-4}$alkyl-phenyl, —$C_{1-4}$alkylheteroaryl, carbocyclyl, —$C_{1-4}$alkylheterocyclyl, -heterocyclyl-heteroaryl, -phenyl-heterocyclyl, -carbocyclyl-heteroaryl, heterocyclyl-phenyl, or -heterocyclyl-O-heteroaryl, wherein said groups the heterocyclyl, phenyl, heteroaryl or carbocyclyl moiety may be optionally substituted with one or more substituents selected from the group consisting of halogen, $C_{1-4}$alkoxy, —C(O)$C_{1-4}$alkyl, —$C_{0-4}$alkylSO₂$C_{1-4}$alkyl, cyano, hydroxy, and $C_{1-4}$alkyl;
R³ is hydrogen or $C_{1-4}$alkyl, or
R² and R³ may together with the nitrogen atom, form a saturated ring system containing 4 or 5 or 6 ring forming atoms selected from carbon or nitrogen;
R⁴ is hydrogen,
wherein
heteroaryl is a monocyclic aromatic heterocycle containing 1 or 2 heteroatoms that are each independently nitrogen, sulphur, or oxygen; or benzodioxolyl; and
heterocyclyl is a saturated monocyclic ring containing 3 to 7 atoms of which 1 or 2 ring atoms are each independently nitrogen, sulphur, or oxygen;
or a pharmaceutically acceptable salt thereof.

7. The compound of formula (I) according to claim 1, wherein
R¹ is pyridine-2-yl;
R² and R³ are $C_{1-4}$alkyl;
R⁴ is hydrogen, or a pharmaceutically acceptable salt thereof.

8. The compound according to claim 1, which is
7-(4-(2-(Pyridin-2-yl)ethyl)piperazin-1-yl)-N-(pyridin-2-ylmethyl)benzofuran-2-carboxamide;
N-(4-Morpholinophenyl)-7-(4-(2-(pyridin-2-yl)ethyl)piperazin-1-yl)benzofuran-2-carboxamide;
N-(1-Phenylpiperidin-4-yl)-7-(4-(2-(pyridin-2-yl)ethyl) piperazin-1-yl)benzofuran-2-carboxamide;
N-(4-(Methylsulfonyl)benzyl)-7-(4-(2-(pyridin-2-yl) ethyl)piperazin-1-yl)benzofuran-2-carboxamide;
N-((1 -Methyl-1H-imidazol-4-yl)methyl)-7-(4-(2-(pyridin-2-yl)ethyl)piperazin-1 -yl)benzofuran-2-carboxamide;
N-(1 -Acetylpiperidin-4-yl)-7-(4-(2-(pyridin-2-yl)ethyl) piperazin-1-yl)benzofuran-2-carboxamide;
N-(1-(Pyridin-2-yl)ethyl)-7-(4-(2-(pyridin-2-yl)ethyl) piperazin-1-yl)benzofuran-2-carboxamide;
N-(1-(3-Chloropyridin-2-yl)piperidin-4-yl)-7-(4-(2-(pyridin-2-yl)ethyl)piperazin-1-yl)benzofuran-2-carboxamide;
N-(4-Cyanobenzyl)-7-(4-(2-(pyridin-2-yl)ethyl)piperazin-1-yl)benzofuran-2-carboxamide;
N-(Benzo [d][1,3]dioxol5-ylmethyl)-7-(4-(2-(pyridin-2-yl)ethyl)piperazin-1-yl)benzofuran-2-carboxamide;
N-Methyl-7-(4-(2-(pyridin-2-yl)ethyl)piperazin-1-yl) benzofuran-2-carboxamide;
N-Cyclopropyl-7-(4-(2-(pyridin-2-yl)ethyl)piperazin-1-yl)benzofuran-2-carboxamide;
N-(3,3-Difluorocyclobutyl)-7-(4-(2-(pyridin-2-yl)ethyl) piperazin-1-yl)benzofuran-2-carboxamide;
Azetidin-1-yl(7-(4-(2-(pyridin-2-yl)ethyl)piperazin-1-yl) benzofuran-2-yl)methanone;
(7-(4-(2-(Pyridin-2-yl)ethyl)piperazin-1-yl)benzofuran-2-yl)(pyrrolidin-1-yl)methanone;
N-(4-(Methylsulfonylmethyl)benzyl)-7-(4-(2-(pyridin-2-yl)ethyl)piperazin-1-yl)benzofuran-2-carboxamide;
N-(3-Methoxyphenethyl)-7-(4-(2-(pyridin-2-yl)ethyl) piperazin-1-yl)benzofuran-2-carboxamide;
N-Methyl-N-(3-(methylsulfonyl)benzyl)-7-(4-(2-(pyridin-2-yl)ethyl)piperazin-1-yl)benzofuran-2-carboxamide;
N-((6-Cyanopyridin-3-yl)methyl)-7-(4-(2-(pyridin-2-yl) ethyl)piperazin-1-yl)benzofuran-2-carboxamide;
N-Methyl-7-(4-(2-(pyridin-2-yl)ethyl)piperazin-1-yl)-N-(pyridin-3-ylmethyl)benzofuran-2-carboxamide;
N-(3 -Cyanobenzyl)-7-(4-(2-(pyridin-2-yl)ethyl)piperazin- 1 -yl)benzofuran-2-carboxamide;
(7-(4-(2-(Pyridin-2-yl)ethyl)piperazin- 1-yl)benzofuran-2-yl)(4-(thiazol-2-yl)piperazin-11-yl)methanone;
N-(1-(3-Methoxypyridin-2-yl)piperidin-4-yl)-7-(4-(2-(pyridin-2-yl)ethyl)piperazin-1-yl)benzofuran-2-carboxamide;
N-Methyl-7-(4-(2-(pyridin-2-yl)ethyl)piperazin- 1 yl)-N-(pyridin-2-ylmethyl)benzofuran-2-carboxamide;
N-(3 -Methoxybenzyl)-7-(4-(2-(pyridin-2-yl)ethyl)piperazin- 1 -yl)benzofuran-2-carboxamide;
N-(1 -(Pyridin-2-yl)cyclopropyl)-7-(4-(2-(pyridin-2-yl) ethyl)piperazin-1 -yl)benzofuran-2-carboxamide;
N-(4-Methoxybenzyl)-7-(4-(2-(pyridin-2-yl)ethyl)piperazin- 1-yl)benzofuran-2-carboxamide;
N-(2-(4-Methylpyrimidin-2-yl)ethyl)-7-(4-(2-(pyridin-2-yl)ethyl)piperazin- 1-yl)benzofuran-2-carboxamide;
N-(2-(1-Methyl-1H-imidazol-4-yl)ethyl)-7-(4-(2-(pyridin-2-yl)ethyl)piperazin-1-yl)benzofuran-2-carboxamide;
7-(4-(2-(Pyridin-2-yl)ethyl)piperazin- 1-yl)-N-((tetrahydro-2H-pyran-4-yl)methyl)benzofuran-2-carboxamide;
N-(1-(1-Methyl-1H-pyrazol-5-yl)ethyl)-7-(4-(2-(pyridin-2-yl)ethyl)piperazin-1-yl)benzofuran-2-carboxamide;
N-(1-(6-Methylpyridin-3-yl)ethyl)-7-(4-(2-(pyridin-2-yl) ethyl)piperazin-1-yl)benzofuran-2-carboxamide;
N-((2-Methylpyrimidin-5-yl)methyl)-7-(4-(2-(pyridin-2-yl)ethyl)piperazin-1-yl)benzofuran-2-carboxamide;
7-(4-(2-(Pyridin-2-yl)ethyl)piperazin-1-yl)-N-(pyridin-3-ylmethyl)benzofuran-2-carboxamide;
(7-(4-(2-(Pyridin-2-yl)ethyl)piperazin-1-yl)benzofuran-2-yl)(3-(pyridin-3-yloxy)azetidin-1-yl)methanone;
N-(3-Hydroxybenzyl)-7-(4-(2-(pyridin-2-yl)ethyl)piperazin-1-yl)benzofuran-2-carboxamide;
7-(4-(2-(4-Methoxypyridin-2-yl)ethyl)piperazin-1-yl)—N,N-dimethylbenzofuran-2-carboxamide;
N,N-dimethyl-7-(4-(2-(5-methylpyridin-2-yl)ethyl)piperazin-1-yl)benzofuran-2-carboxamide;

7-(4-(2-(4-Cyanopyridin-2-yl)ethyl)piperazin-1-yl)—N,N-dimethylbenzofuran-2-carboxamide;
N,N-Dimethyl-7-(4-(2-(6-(trifluoromethyl)pyridin-2-yl)ethyl)piperazin-1-yl)benzofuran-2-carboxamide;
7-(4-(2-(5-Acetylpyridin-2-yl)ethyl)piperazin-1-yl)-N,N-dimethylbenzofuran-2-carboxamide;
7-(4-(2-(5-Acetamidopyridin-2-yl)ethyl)piperazin-1-yl)-N,N-dimethylbenzofuran-2-carboxamide;
Azetidin-1-yl(7-(4-(2-(6-methoxypyridin-2-yl)ethyl)piperazin-1-yl)benzofuran-2-yl)methanone;
7-(4-(2-(6-Methoxypyridin-2-yl)ethyl)piperazin-1-yl)-N,N-dimethylbenzofuran-2-carboxamide;
7-(4-(2-(5-Fluoropyridin-2-yl)ethyl)piperazin-1-yl)-N,N-dimethylbenzofuran-2-carboxamide;
7-(4-(2-(3-Methoxy-2-pyridyl)ethyl)piperazin-1-yl)-N,N-dimethylbenzofuran-2-carboxamide;
1-(5-(2-(4-(2-(Azetidine-1-carbonyl)benzofuran-7-yl)piperazin-1-yl)ethyl)indolin-1-yl)ethanone;
5-Fluoro-N,N-dimethyl-7-(4-(2-pyridin-2-yl)piperazin-1-yl)benzofuran-2-carboxamide;
7-(4-(2-(1-Acetylindolin-5-yl)ethyl)piperazin-1-yl)-5-fluoro-N,N-dimethylbenzofuran-2-carboxamide;
5-Methoxy-N,N-dimethyl-7-(4-(2-(pyridin-2-yl)ethyl)piperazin-1-yl)benzofuran-2-carboxamide and
4-Bromo-N,N-dimethyl-7-(4-(2-(pyridin-2-yl)ethyl)piperazin-1-yl)benzofuran-2-carboxamide; or a pharmaceutically acceptable salt thereof.

9. A pharmaceutical composition comprising as active ingredient a therapeutically effective amount of a compound of formula (I) according to claim 1 in association with a pharmaceutically acceptable excipient, carrier or diluent.

10. A method of treating bipolar depression or Major Depressive Disorders (MDD) comprising administering to a patient in need of such a treatment, a therapeutically effective amount of a compound of formula (I) or a pharmaceutically acceptable salt thereof as defined in claim 1.

11. A method of treating depression or major depression comprising administering to a patient in need of such a treatment a therapeutically effective amount of a compound of formula (I) or a pharmaceutically acceptable salt thereof as defined in claim 1.

* * * * *